(12) United States Patent
Karandikar et al.

(10) Patent No.: US 8,900,624 B2
(45) Date of Patent: Dec. 2, 2014

(54) ANTIMICROBIAL SILVER COMPOSITIONS

(75) Inventors: Bhalchandra M. Karandikar, Tigard, OR (US); Bruce L. Gibbins, Lake Oswego, OR (US); Ken A. Cornell, Meridian, ID (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 1198 days.

(21) Appl. No.: 11/194,951

(22) Filed: Aug. 1, 2005

(65) Prior Publication Data

US 2007/0003603 A1    Jan. 4, 2007

Related U.S. Application Data

(60) Provisional application No. 60/592,687, filed on Jul. 30, 2004.

(51) Int. Cl.

| | | |
|---|---|---|
| *A61K 33/38* | (2006.01) | |
| *A61K 9/70* | (2006.01) | |
| *A61L 15/18* | (2006.01) | |
| *D06M 16/00* | (2006.01) | |
| *D06M 11/83* | (2006.01) | |
| *D06M 23/08* | (2006.01) | |
| *A61L 15/46* | (2006.01) | |
| *A61L 29/16* | (2006.01) | |
| *A01N 59/16* | (2006.01) | |

(52) U.S. Cl.
CPC .................. *A01N 59/16* (2013.01); *A61L 15/18* (2013.01); *A61L 2300/624* (2013.01); *D06M 16/00* (2013.01); *A61L 2300/404* (2013.01); *D06M 11/83* (2013.01); *D06M 23/08* (2013.01); *A61L 15/46* (2013.01); *A61L 2400/12* (2013.01); *A61L 29/16* (2013.01); *A61L 2300/104* (2013.01); *A61K 33/38* (2013.01); *Y10S 977/906* (2013.01)
USPC ............................ 424/443; 424/618; 977/906

(58) Field of Classification Search
CPC ....... A01N 59/16; A01N 25/22; B82Y 30/00; Y10S 977/773; A61K 33/38; A61L 15/18; A61L 2300/104; A61L 2400/12; D06M 11/83
See application file for complete search history.

(56) References Cited

U.S. PATENT DOCUMENTS

| | | |
|---|---|---|
| 2,396,515 A | 3/1946 | Werner Kreidl et al. |
| 3,092,552 A | 6/1963 | Romans |

(Continued)

FOREIGN PATENT DOCUMENTS

| | | |
|---|---|---|
| EP | 0072251 A2 | 2/1983 |
| EP | 0297769 A1 | 1/1989 |

(Continued)

OTHER PUBLICATIONS

Sudhir Kapoor, "Preparation, Characterization, and Surface Modification of Silver Particles" Langmuir 1998, 14, 1021-1025.*

(Continued)

*Primary Examiner* — Kortney L Klinkel
(74) *Attorney, Agent, or Firm* — Dority & Manning, P.A.

(57) ABSTRACT

The present invention comprises methods and compositions for antimicrobial silver compositions comprising silver nanoparticles. The present invention further comprises compositions for preparing silver nanoparticles comprising at least one stabilizing agent, one or more silver compounds, at least one reducing agent and a solvent. In one aspect, the stabilizing agent comprises a surfactant or a polymer. The polymer may comprise polymers such as polyacrylamides, polyurethanes, and polyamides. In one aspect, the silver compound comprises a salt comprising a silver cation and an anion. The anion may comprise saccharinate derivatives, long chain fatty acids, and alkyl dicarboxylates. The methods of the present invention comprise treating devices with the silver nanoparticle compositions, including, but not limited to, such devices as woven wound care materials, catheters, patient care devices, and collagen matrices. The present invention further comprises treatment of humans and animals wacr6ith the antimicrobial devices described herein.

8 Claims, 9 Drawing Sheets

(56) References Cited

U.S. PATENT DOCUMENTS

| | | | |
|---|---|---|---|
| 3,152,094 A | 10/1964 | Erner et al. |
| 3,152,904 A | 10/1964 | Sorensen et al. |
| 3,157,524 A | 11/1964 | Artandi |
| 3,485,658 A | 12/1969 | Iler |
| 3,511,764 A | 5/1970 | Marans et al. |
| 3,624,835 A | 11/1971 | Wyatt |
| 3,645,835 A | 2/1972 | Hodgson |
| 3,647,439 A | 3/1972 | Bass |
| 3,846,236 A | 11/1974 | Updike et al. |
| 3,933,507 A | 1/1976 | Von Konig et al. |
| 3,969,498 A | 7/1976 | Catania et al. |
| 3,996,141 A | 12/1976 | Updike |
| 4,113,658 A | 9/1978 | Geus |
| 4,130,517 A | 12/1978 | Lundberg et al. |
| 4,136,177 A | 1/1979 | Lin et al. |
| 4,136,178 A | 1/1979 | Lin et al. |
| 4,260,677 A | 4/1981 | Winslow et al. |
| 4,306,551 A | 12/1981 | Hymes et al. |
| 4,310,509 A | 1/1982 | Berglund et al. |
| 4,320,201 A | 3/1982 | Berg et al. |
| 4,328,799 A | 5/1982 | LoPiano |
| 4,340,043 A | 7/1982 | Seymour |
| 4,364,929 A | 12/1982 | Sasmor et al. |
| 4,393,048 A | 7/1983 | Mason, Jr. et al. |
| 4,474,571 A | 10/1984 | Lasley |
| 4,483,688 A | 11/1984 | Akiyama |
| 4,529,623 A | 7/1985 | Maggs |
| 4,604,384 A | 8/1986 | Smith et al. |
| 4,608,041 A | 8/1986 | Nielsen |
| 4,612,337 A | 9/1986 | Fox, Jr. et al. |
| 4,624,656 A | 11/1986 | Clark et al. |
| 4,686,211 A | 8/1987 | Hara et al. |
| 4,708,821 A | 11/1987 | Shimokawa et al. |
| 4,721,724 A | 1/1988 | Stettendorf et al. |
| 4,747,847 A | 5/1988 | Magruder et al. |
| 4,782,819 A | 11/1988 | Adair |
| 4,801,291 A | 1/1989 | Loori |
| 4,902,503 A | 2/1990 | Umemura et al. |
| 4,915,694 A | 4/1990 | Yamamoto et al. |
| 4,969,881 A | 11/1990 | Viesturs |
| 5,023,082 A | 6/1991 | Friedman et al. |
| 5,049,139 A | 9/1991 | Gilchrist |
| 5,076,265 A | 12/1991 | Wokalek |
| 5,086,620 A | 2/1992 | Spears |
| 5,091,171 A | 2/1992 | Yu et al. |
| 5,100,668 A | 3/1992 | Edelman et al. |
| 5,128,326 A | 7/1992 | Balazs et al. |
| 5,149,524 A | 9/1992 | Sherba et al. |
| 5,151,271 A | 9/1992 | Otsuka et al. |
| 5,158,772 A | 10/1992 | Davis |
| 5,175,229 A | 12/1992 | Braatz et al. |
| 5,181,914 A | 1/1993 | Zook |
| 5,196,190 A | 3/1993 | Nangia et al. |
| 5,236,421 A | 8/1993 | Becher |
| 5,270,358 A | 12/1993 | Asmus |
| 5,342,528 A | 8/1994 | Adachi et al. |
| 5,354,862 A | 10/1994 | Hsu |
| 5,407,685 A | 4/1995 | Malchesky et al. |
| 5,429,591 A | 7/1995 | Yamamoto et al. |
| 5,432,077 A | 7/1995 | Farrah |
| 5,447,492 A | 9/1995 | Cartmell et al. |
| 5,453,401 A | 9/1995 | Grivna et al. |
| 5,464,610 A | 11/1995 | Hayes, Jr. et al. |
| 5,470,585 A | 11/1995 | Gilchrist |
| 5,503,840 A | 4/1996 | Jacobson et al. |
| 5,508,038 A | 4/1996 | Wang et al. |
| 5,508,417 A | 4/1996 | Osei-Gyimah et al. |
| 5,516,502 A | 5/1996 | Dickerson |
| 5,527,534 A | 6/1996 | Myhling |
| 5,567,495 A | 10/1996 | Modak et al. |
| 5,569,207 A | 10/1996 | Gisselberg et al. |
| 5,593,683 A | 1/1997 | Viegas et al. |
| 5,599,296 A | 2/1997 | Spears |
| 5,603,946 A | 2/1997 | Constantine |
| 5,614,568 A | 3/1997 | Mawatari et al. |
| 5,660,854 A | 8/1997 | Haynes et al. |
| 5,681,579 A | 10/1997 | Freeman |
| 5,683,713 A | 11/1997 | Blank et al. |
| 5,693,624 A | 12/1997 | Hardy et al. |
| 5,695,777 A | 12/1997 | Donovan et al. |
| 5,709,870 A | 1/1998 | Yoshimura et al. |
| 5,725,491 A | 3/1998 | Tipton et al. |
| 5,735,251 A | 4/1998 | Hyodo et al. |
| 5,736,582 A | 4/1998 | Devillez |
| 5,744,151 A | 4/1998 | Capelli |
| 5,753,251 A | 5/1998 | Burrell et al. |
| 5,792,090 A | 8/1998 | Ladin |
| 5,804,213 A | 9/1998 | Rolf |
| 5,820,918 A | 10/1998 | Ronan et al. |
| 5,830,496 A | 11/1998 | Freeman |
| 5,833,665 A | 11/1998 | Bootman et al. |
| 5,840,283 A | 11/1998 | Sorenson et al. |
| 5,853,742 A | 12/1998 | Bartolone et al. |
| 5,855,570 A | 1/1999 | Scherson et al. |
| 5,863,548 A | 1/1999 | Elder |
| 5,863,864 A | 1/1999 | Plath et al. |
| 5,869,073 A | 2/1999 | Sawan et al. |
| 5,908,693 A | 6/1999 | Delgado et al. |
| 5,927,317 A | 7/1999 | Hsia |
| 5,928,174 A | 7/1999 | Gibbins |
| 5,951,458 A | 9/1999 | Hastings et al. |
| 5,961,996 A | 10/1999 | Garson et al. |
| 5,965,204 A | 10/1999 | Sodervall et al. |
| 5,972,317 A | 10/1999 | Sorenson et al. |
| 5,993,790 A | 11/1999 | Strauss |
| 6,000,403 A | 12/1999 | Cantwell |
| 6,011,194 A | 1/2000 | Buglino et al. |
| 6,042,845 A | 3/2000 | Sun et al. |
| 6,051,614 A | 4/2000 | Hirai et al. |
| 6,099,805 A | 8/2000 | Hartlove |
| 6,103,868 A * | 8/2000 | Heath et al. ............... 528/482 |
| 6,110,447 A | 8/2000 | Ramin et al. |
| 6,113,287 A | 9/2000 | Merz et al. |
| 6,143,794 A | 11/2000 | Chaudhuri et al. |
| 6,159,977 A | 12/2000 | Reeves |
| 6,187,290 B1 | 2/2001 | Gilchrist et al. |
| 6,191,339 B1 | 2/2001 | Gueret |
| 6,201,164 B1 | 3/2001 | Wulff et al. |
| 6,214,360 B1 | 4/2001 | Richter et al. |
| 6,224,622 B1 | 5/2001 | Kotzev |
| 6,231,840 B1 | 5/2001 | Buck |
| 6,235,964 B1 | 5/2001 | Kadash et al. |
| 6,248,342 B1 | 6/2001 | Trogolo et al. |
| 6,264,927 B1 | 7/2001 | Monahan |
| 6,270,811 B1 | 8/2001 | Fregonese |
| 6,316,084 B1 | 11/2001 | Claus et al. |
| 6,326,524 B1 | 12/2001 | Fattman et al. |
| 6,355,858 B1 | 3/2002 | Gibbins |
| 6,468,989 B1 | 10/2002 | Chang et al. |
| 6,471,982 B1 | 10/2002 | Lydon et al. |
| 6,530,895 B1 | 3/2003 | Keirn |
| 6,605,751 B1 * | 8/2003 | Gibbins et al. ............... 602/41 |
| 6,669,981 B2 | 12/2003 | Parsons et al. |
| 6,716,895 B1 | 4/2004 | Terry |
| 6,897,349 B2 | 5/2005 | Gibbins et al. |
| 6,921,529 B2 | 7/2005 | Maley |
| 7,129,389 B1 | 10/2006 | Watson |
| 7,160,553 B2 | 1/2007 | Gibbins et al. |
| 7,166,330 B2 | 1/2007 | Takahashi et al. |
| 7,189,410 B1 | 3/2007 | Drohan et al. |
| 7,576,255 B2 | 8/2009 | Gibbins et al. |
| 2001/0026810 A1 | 10/2001 | McGhee et al. |
| 2001/0041188 A1 | 11/2001 | Gibbins et al. |
| 2002/0001604 A1 | 1/2002 | Shigeru et al. |
| 2002/0042587 A1 | 4/2002 | Murdock |
| 2002/0073891 A1 | 6/2002 | Parsons et al. |
| 2002/0082340 A1 | 6/2002 | Hanke et al. |
| 2003/0041188 A1 | 2/2003 | Han et al. |
| 2003/0083610 A1 | 5/2003 | McGrath et al. |
| 2003/0093057 A1 | 5/2003 | Zhang et al. |
| 2003/0186955 A1 | 10/2003 | Vange et al. |
| 2004/0010215 A1 | 1/2004 | Gibbins et al. |
| 2004/0082925 A1 | 4/2004 | Patel |
| 2004/0096410 A1 | 5/2004 | Maley et al. |

(56) References Cited

U.S. PATENT DOCUMENTS

| | | |
|---|---|---|
| 2004/0108462 A1 | 6/2004 | Besesty et al. |
| 2004/0127025 A1 | 7/2004 | Crocker et al. |
| 2004/0147618 A1 | 7/2004 | Lee et al. |
| 2004/0170545 A1 | 9/2004 | Emanuel |
| 2004/0173056 A1 | 9/2004 | McNally et al. |
| 2004/0180093 A1 | 9/2004 | Burton et al. |
| 2004/0253536 A1 | 12/2004 | Park et al. |
| 2004/0254532 A1 | 12/2004 | Mehier |
| 2005/0008861 A1 | 1/2005 | Yadav et al. |
| 2005/0029121 A1 | 2/2005 | Monzyk et al. |
| 2005/0186135 A1 | 8/2005 | Howes |
| 2005/0265894 A1 | 12/2005 | Monzyk et al. |
| 2006/0276740 A1 | 12/2006 | Bagley |
| 2007/0003603 A1 | 1/2007 | Karandikar et al. |
| 2007/0207335 A1 | 9/2007 | Karandikar et al. |
| 2007/0254044 A1 | 11/2007 | Karandikar et al. |
| 2007/0293800 A1 | 12/2007 | McMaken et al. |
| 2010/0034882 A1 | 2/2010 | Gibbins et al. |

FOREIGN PATENT DOCUMENTS

| | | |
|---|---|---|
| EP | 0489206 A1 | 6/1992 |
| EP | 0500387 | 8/1992 |
| EP | 0707793 A1 | 4/1996 |
| EP | 0709101 A2 | 5/1996 |
| EP | 1245239 A1 | 10/2002 |
| EP | 1388561 A2 | 2/2004 |
| GB | 863875 A | 3/1961 |
| GB | 1471013 A | 4/1977 |
| GB | 1554002 A | 10/1979 |
| GB | 2024012 A | 1/1980 |
| GB | 2134791 A | 8/1984 |
| JP | 05-271718 A | 10/1993 |
| JP | 6248549 A | 9/1994 |
| JP | 7097767 A | 4/1995 |
| JP | 11302119 A | 11/1999 |
| JP | 2003529630 A | 10/2003 |
| JP | 2004137615 A | 5/2004 |
| JP | 2004161632 A | 6/2004 |
| WO | WO-84/01721 A1 | 5/1984 |
| WO | WO-88/06894 A1 | 9/1988 |
| WO | WO-90/03810 A1 | 4/1990 |
| WO | WO-96/11572 A1 | 4/1996 |
| WO | WO-98/06260 A1 | 2/1998 |
| WO | WO-98/20719 A1 | 5/1998 |
| WO | WO-99/15101 A2 | 4/1999 |
| WO | WO-99/25395 A2 | 5/1999 |
| WO | WO-00/09173 A1 | 2/2000 |
| WO | WO-00/15202 A2 | 3/2000 |
| WO | WO-01/11955 A2 | 2/2001 |
| WO | WO-01/24839 A1 | 4/2001 |
| WO | WO-01/49258 A2 | 7/2001 |
| WO | WO-0226039 A1 | 4/2002 |
| WO | WO-0243743 A1 | 6/2002 |
| WO | WO-02/061403 A1 | 8/2002 |
| WO | WO-02/076518 A1 | 10/2002 |
| WO | WO-03/002089 A1 | 1/2003 |
| WO | WO-03/080231 A1 | 10/2003 |
| WO | WO-2004/001880 A1 | 12/2003 |
| WO | WO-2004/010952 A2 | 2/2004 |
| WO | WO-2004/028255 A1 | 4/2004 |
| WO | WO-2004/056404 A2 | 7/2004 |
| WO | WO-2006/015317 A2 | 2/2006 |
| WO | WO-2006/034249 A2 | 3/2006 |
| WO | WO-2007/095058 A2 | 8/2007 |
| WO | WO-2007/127236 A2 | 11/2007 |
| WO | WO-2008/131070 A1 | 10/2008 |

OTHER PUBLICATIONS

Search Report for PCT patent application No. PCT/US2005/027261, dated Apr. 28, 2006.
Liz-Marzán et al., "Reduction and Stabilization of Silver Nanoparticles in Ethanol by Nonionic Surfactants," *Langmuir*, vol. 12, 1996, pp. 3585-3589.
Pastoriza-Santos et al., "Reduction of silver nanoparticles in DMF. Formation of monolayers and stable colloids," *Pure Appl. Chem.*, vol. 72, Nos. 1-2, 2000, pp. 83-90.
Article—Wagner et al, "Characterization of Silver Anthranilate, a Promising Antibacterial Agent," *Acta Farm. Bonaerense*, vol. 21, No. 1, 2002, pp. 27-30.
Acticoat RTM, Silver Coated Dressing Marketing Materials. The Westaim Corporation, 1988.
Bharathi, Subramanian et al., "Sol-Gel-Derived Nanocrystalline Gold-Silicate Composite Biosensor," Analytical Communications, 1998, 35: 29-31.
Chase, Grafton D., Pharmaceutical Science by Remington, 14th Edition., Mack Publishing Co., Rheology, Newtonian Flow-Plastic Flow-Pseudoplastic Flow-Dilatant Flow-Methods for Measuring Viscosity-Polymer Solutions-Thixotrophy-Pharmaceutical Applications, 1970, 359-371.
ConvaTec Corp. Aquacel Ag Product Info from website. [internet citation] Retrieved Dec. 9, 2002 from http://www.convatec.com/en_US/company/pr/index.html.
Cooper, Rose, "A Review of the Evidence for the use of Topical Antimicrobial Agents in Wound Care," World Wide Wounds, 2004, 1-15.
Deitch, E. et al., "Silver-Nylon: a New Antimicrobial Agent". Antimicrobial Agents and Chemotherapy, 1983, 23(3):356-359.
Deitch, E., et al., Abstract, "Silver-impregnated nylon cloth dressing: in vitro and in vivo evaluation of antimicrobial activity," J. Trauma, 1987, pp. 301-304, vol. 27, No. 3.
FDA Approval Letter to begin OxyGenesis marketing. Sep. 19, 2008.
Feng et al, "Study of the initiation mechanism of the vinyl polymerization with the system persulfate/N,N,N',N'-tetramethylethylenediamine," Makromol. Chem. 1988, 189: 77-83.
Fox, Jr., Charles L., "Silver Sulfadiazine—A New Topical", Arch. Surg., vol. 96, pp. 184-188, 1968.
Gibbins et al., AcryDerm Absorbent Oxygen Dressing Point of Use Evaluation: Summary of Results. DRAFT. Jul. 17, 2009.
Gibbins, B. and Hopman, L., "A Comparison of a New Anti-Microbial Polyacrylate Absorbent Wound Dressing Containing Silver with the Silver-containing Anti-microbial Film Dressings", Presentation at Clinical Symposium on Wound Care, Oct 2, 1999.
Gibbins, Bruce, "The Antimicrobial Benefits of Silver and the Relevance of Microlattice Technology," Ostomy Wound Manage. Feb. 2003; Suppl:4-7.
Hackh's Chemical Dictionary, 4th Edition, McGraw Hill Book Co., New York, 1969; pg. 451.
Handbook of Common Polymers, "Polyvinyl Alcohol Including Insolubilised Fibres," Scott & Roff, Jr., W.J., The Chemical Company, 1971, pp. 72-197.
Jia et al., "Effect of locally released oxygen on wound healing," Presented at 18th Annual Meeting of the Wound Healing Society, San Diego, CA. Apr. 2008.
Junhui He et al, "Facile in situ synthesis of noble metal nanoparticles in porous cellulose fibers," Chemistry of Materials, 2003, 15(23): 4401-4406.
Mackeen, P., et al., "Silver-Coated Nylon Fiber as an Antibacterial Agent," Antimicrobial Agents and Chemotherapy, 1987, 31(1): 93-99.
Milk Composition & Synthesis Resourse Library, Milk Composition-Minerals [retrieved on Dec. 5, 2010], retrieved from the internet: <URL:http://ciasses.ansci.illinois.edu/ansc438/milkcompsynth/milkcomp_minerals.html>.
OxyGenesis Dissolved Oxygen Dressings: Case Review, AcryMed, Inc., Jan. 23, 2010.
Pepe, R.C, Wenninger, J.A., & McEwen, G.N., eds., Int'l Cosmetic Ingredient Dictionary & Handbook, 9th ed., 2002, vol. 2. pp. 177.
Price, William R. et al., "Silver Nitrate Burn Dressing, Treatment of Seventy Burned Persons," American Journal of Surgery, 1966, 112:674-680.
Ratner, Buddy D. et al., ACS Symposium Series, No. 31, The American Chemical Society, Synthetic Hydrogels for Biomedical Applications, pp. 1-36.
Rifai et al., "Facile in Situ Silver Nanoparticle Formation in Insulating Porous Polymer Matrices," Chemistry of Materials 2006; 18(1): 21-25.

(56) References Cited

OTHER PUBLICATIONS

Roe, David F., Gibbins, Bruce L., and Ladizinsky, Daniel A., "Topical Dissolved Oxygen Penetrates Skin: Model and Method," J Surg Res. 2010, 159(1):e29-e36.
Schacht, Etienne H., Hydrogel Drug Delivery Systems, Institute of Organic Chemistry, State University Gent, 1984, pp. 259-278.
Sheehan et al, "Anti-bacterial Silver Coatings on Orthopaedic Metals—An In Vitro and Animal Study," Journal of Bone and Joint Surgery. 2003, 85-B(SUPP_II):141.
Silver, Simon, "Bacterial Silver Resistance: Molecular Biology and Uses and Misuses of Silver Compounds," FEMS Microbiology Reviews, 2003, pp. 341-353.
Topical Delivery Methods, undated reference, retrieved from file on May 11, 2011.
Wang et al., "Directing oleate stabilized nanosized silver colloids into organic phases", Langmuir: The ACS Journal of Surfaces and Colloids. 1998; 14:602-610.
Communication regarding the expiration of opposition period issued on Feb. 10, 2006 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Decision to grant a European Pat. issued on Feb. 24, 2005 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Approval of request for amendments/corrections issued on Feb. 15, 2005 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Reply to communication from the Examining Division filed on Dec. 22, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Result of Consultation by telephone/in person (with time limit) issued on Nov. 9, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Request for correction/amendment of the text proposed for grant filed on Oct. 26, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication about intention to grant a European Pat. issued on Jun. 18, 2004 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Reply to communication from the Examining Division filed on Aug. 20, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division issued on May 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Reply to communication from the Examining Division filed on Feb. 5, 2003 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division issued on Aug. 1, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Reply to communication from the Examining Division filed on May 20, 2002 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
Communication from the Examining Division issued Jul. 31, 2001 for European Pat. App. No. 98961733.7 which claims priority to PCT/US98/024272 filed on Nov. 13, 1998, published May 27, 1999 as WO 99/027680 (Applicant—Acrymed; Inventors: B.L. Gibbins).
PCT Intl. Search Report issued on Jun. 23, 1999 for PCT/US98/24272, filed on Nov. 13, 1998, published May 27, 1999 as WO 99/027680 (Applicant—Acrymed; Inventors: B.L. Gibbins).
PCT Intl. Preliminary exam report issued on Aug. 8, 2001 for PCT/US98/24272, filed on Nov. 13, 1998, published May 27, 1999 as WO 99/027680 (Applicant—Acrymed; Inventors: B.L. Gibbins).
PCT Written opinion issued on Feb. 18, 2000 for PCT/US98/24272, filed on Nov. 13, 1998, published May 27, 1999 as WO 99/027680 (Applicant—Acrymed; Inventors: B.L. Gibbins).
Issue Notification issued on Jul. 14, 1999 for U.S. Appl. No. 08/971,074, filed on Nov. 14, 1997 (Inventor—B.L. Gibbins).
Notice of Allowance issued on Feb. 25, 1999 for U.S. Appl. No. 08/971,074, filed on Nov. 14, 1997 (Inventor—B.L. Gibbins).
Examiner Interview Summary/Amendment issued on Dec. 11, 1998 for U.S. Appl. No. 08/971,074, filed on Nov. 14, 1997 (Inventor—B.L. Gibbins).
Response after Non-Final Action filed on Nov. 18, 1998 for U.S. Appl. No. 08/971,074, filed on Nov. 14, 1997 (Inventor—B.L. Gibbins).
Non-Final Rejection issued on Aug. 19, 1998 for U.S. Appl. No. 08/971,074, filed on Nov. 14, 1997 (Inventor—B.L. Gibbins).
Response to Election / Restriction filed on Jul. 14, 1998 for U.S. Appl. No. 08/971,074, filed on Nov. 14, 1997 (Inventor—B.L. Gibbins).
Restriction Requirement issued on May 21, 1998 for U.S. Appl. No. 08/971,074, filed on Nov. 14, 1997 (Inventor—B.L. Gibbins).
Issue Notification issued on Mar. 12, 2002 for U.S. Appl. No. 09/191,223, filed on Nov. 13, 1998 (Inventor—B.L. Gibbins).
Notice of Allowance issued on Sep. 25, 2001 for U.S. Appl. No. 09/191,223, filed on Nov. 13, 1998 (Inventor—B.L. Gibbins).
Notice of Allowance issued on Oct. 3, 2000 for U.S. Appl. No. 09/191,223, filed on Nov. 13, 1998 (Inventor—B.L. Gibbins).
Response after Non-Final Action filed on Aug. 11, 2000 for U.S. Appl. No. 09/191,223, filed on Nov. 13, 1998 (Inventor—B.L. Gibbins).
Non-Final Rejection issued on Apr. 11, 2000 for U.S. Appl. No. 09/191,223, filed on Nov. 13, 1998 (Inventor—B.L. Gibbins).
Response to Election / Restriction filed on Mar. 21, 2000 for U.S. Appl. No. 09/191,223, filed on Nov. 13, 1998 (Inventor—B.L. Gibbins).
Restriction Requirement issued on Feb. 22, 2000 for U.S. Appl. No. 09/191,223, filed on Nov. 13, 1998 (Inventor—B.L. Gibbins).
Communication regarding the expiry of opposition period issued on Sep. 2, 2009 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Decision to grant a European Pat. issued on Oct. 2, 2008 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Communication about intention to grant a European Pat. issued on Apr. 10, 2008 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Reply to communication from the Examining Division filed on Feb. 26, 2008 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Communication from the Examining Division issued on Oct. 18, 2007 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Reply to communication from the Examining Division filed on Dec. 28, 2006 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).

(56) References Cited

OTHER PUBLICATIONS

Communication from the Examining Division issued on Sep. 1, 2006 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Reply to communication from the Examining Division filed on Mar. 21, 2005 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Communication from the Examining Division issued on Sep. 20, 2004 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Reply to communication from the Examining Division filed on Feb. 27, 2003 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
Communication from the Examining Division issued on Aug. 21, 2002 for EP App. No. 970522.9, which claims priority to Intl. Pat. App. No. PCT/US00/26890, filed 9/29/200, published on Apr. 12, 2001 as WO 01/024839 (Applicant—Acrymed, Inc.).
PCT Intl. Search Report issued on Feb. 5, 2001 for PCT/US00/26890, filed on Sep. 29, 2000, published Apr. 12, 2001 as WO 01/24839 (Applicant—Acrymed; Inventors: Gibbins).
PCT Written Opinion issued on Jul. 23, 2001 for PCT/US00/26890, filed on Sep. 29, 2000, published Apr. 12, 2001 as WO 01/24839 (Applicant—Acrymed; Inventors: Gibbins).
PCT Intl. Preliminary Examination Report issued on Oct. 17, 2001 for PCT/US00/26890, filed on Sep. 29, 2000, published Apr. 12, 2001 as WO 01/24839 (Applicant—Acrymed; Inventors: Gibbins).
Notice of Allowance issued on Apr. 15, 2003 for U.S. Appl. No. 09/675,892, filed on Sep. 29, 2000 (Inventor—B.L. Gibbins).
Amendment/Response After Non-Final Rejection filed on Mar. 21, 2003 for U.S. Appl. No. 09/675,892, filed on Sep. 29, 2000 (Inventor—B.L. Gibbins).
Non-Final Rejection issued on Nov. 21, 2002 for U.S. Appl. No. 09/675,892, filed on Sep. 29, 2000 (Inventor—B.L. Gibbins).
Amendment After Final filed on Oct. 30, 2002 for U.S. Appl. No. 09/675,892, filed on Sep. 29, 2000 (Inventor—B.L. Gibbins).
Final Rejection issued on Jul. 31, 2002 for U.S. Appl. No. 09/675,892, filed on Sep. 29, 2000 (Inventor—B.L. Gibbins).
Amendment/Response After Non-Final Rejection filed on Apr. 18, 2002 for U.S. Appl. No. 09/675,892, filed on Sep. 29, 2000 (Inventor—B.L. Gibbins).
Non-Final Rejection issued on Jan. 18, 2002 for U.S. Appl. No. 09/675,892, filed on Sep. 29, 2000 (Inventor—B.L. Gibbins).
Notice of Allowance issued on Mar. 7, 2005 for U.S. Appl. No. 10/441,275, filed on May 19, 2003 (Inventor—B.L. Gibbins).
Notice of Allowance/Examiner Interview Summary Record issued on Jul. 2, 2004 for U.S. Appl. No. 10/441,275, filed on May 19, 2003 (Inventor—B.L. Gibbins).
Examiner Interview Summary Record (PTOL—413) issued May 26, 2004 for U.S. Appl. No. 10/441,275, filed on May 19, 2003 (Inventor—B.L. Gibbins).
Supplemental Preliminary Amendment filed on Mar. 25, 2004 for U.S. Appl. No. 10/441,275, filed on May 19, 2003 (Inventor—B.L. Gibbins).
Preliminary Amendment filed on Dec. 2, 2003 for U.S. Appl. No. 10/441,275, filed on May 19, 2003 (Inventor—B.L. Gibbins).
Issue Notification issued on Jul. 29, 2009 for U.S. Appl. No. 10/978,556, filed on Nov. 1, 2004 (Inventor—B.L. Gibbins).
Notice of Allowance issued on Apr. 16, 2009 for U.S. Appl. No. 10/978,556, filed on Nov. 1, 2004 (Inventor—B.L. Gibbins).
Terminal Disclaimer/Amendment After Final Rejection filed on Apr. 6, 2009 for U.S. Appl. No. 10/978,556, filed on Nov. 1, 2004 (Inventor—B.L. Gibbins).
Final Rejection issued on Nov. 6, 2008 for U.S. Appl. No. 10/978,556, filed on Nov. 1, 2004 (Inventor—B.L. Gibbins).
Amendment/Response After Non-Final Rejection filed on Aug. 1, 2008 for U.S. Appl. No. 10/978,556, filed on Nov. 1, 2004 (Inventor—B.L. Gibbins).
Non-Final Rejection issued on Apr. 1, 2008 for U.S. Appl. No. 10/978,556, filed on Nov. 1, 2004 (Inventor—B.L. Gibbins).
Amendment Submitted/Entered with CPA/RCE filed on Oct. 31, 2007 for U.S. Appl. No. 10/978,556, filed on Nov. 1, 2004 (Inventor—B.L. Gibbins).
Advisory Action (PTOL—303) issued on Oct. 3, 2007 for U.S. Appl. No. 10/978,556, filed on Nov. 1, 2004 (Inventor—B.L. Gibbins).
Amendment After Final Rejection filed on Sep. 13, 2007 for U.S. Appl. No. 10/978,556, filed on Nov. 1, 2004 (Inventor—B.L. Gibbins).
Final Rejection issued on Jul. 13, 2007 for U.S. Appl. No. 10/978,556, filed on Nov. 1, 2004 (Inventor—B.L. Gibbins).
Amendment/Response After Non-Final Rejection filed on Apr. 24, 2007 for U.S. Appl. No. 10/978,556, filed on Nov. 1, 2004 (Inventor—B.L. Gibbins).
Non-Final Rejection issued on Jan. 24, 2007 for U.S. Appl. No. 10/978,556, filed on Nov. 1, 2004 (Inventor—B.L. Gibbins).
Response to Election / Restriction filed on Nov. 13, 2006 for U.S. Appl. No. 10/978,556, filed on Nov. 1, 2004 (Inventor—B.L. Gibbins).
Requirement for Restriction/Election issued on Oct. 11, 2006 for U.S. Appl. No. 10/978,556, filed on Nov. 1, 2004 (Inventor—B.L. Gibbins).
Preliminary Amendment filed on Feb. 15, 2005 for U.S. Appl. No. 10/978,556, filed on Nov. 1, 2004 (Inventor—B.L. Gibbins).
Reexamination Certificate Issued on Jun. 16, 2009 for Inter Partes Reexam No. 95/000,042 of U.S. Pat. 6,605,751 granted Aug. 12, 2003 (Gibbins et al.).
Notice of Intent to Issue a Reexam Certificate issued on Mar. 25, 2009 for Inter Partes Reexam No. 95/000,042 of U.S. Pat. 6,605,751 granted Aug. 12, 2003 (Gibbins et al.).
Right of Appeal Notice issued on Dec. 9, 2008 for Inter Partes Reexam No. 95/000,042 of U.S. Pat. 6,605,751 granted Aug. 12, 2003 (Gibbins et al.).
Action Closing Prosecution (nonfinal) issued on Aug. 19, 2008 for Inter Partes Reexam No. 95/000,042 of U.S. Pat. 6,605,751 granted Aug. 12, 2003 (Gibbins et al.).
Response after non-final action-owner filed on Oct. 8, 2004 for Inter Partes Reexam No. 95/000,042 of U.S. Pat. 6,605,751 granted Aug. 12, 2003 (Gibbins et al.).
Reexam Ordered and Non-Final Action issued on Aug. 4, 2004 for Inter Partes Reexam No. 95/000,042 of U.S. Pat. 6,605,751 granted Aug. 12, 2003 (Gibbins et al.).
Ex Parte Reexam request filed on May 13, 2004 for Inter Partes Reexam No. 95/000,042 of U.S. Pat. 6,605,751 granted Aug. 12, 2003 (Gibbins et al.).
Communication regarding the expiry of opposition period issued on Apr. 4, 2007 for EP App. No. 990393.1, which claims priority to PCT/US00/35560, filed on Dec. 29, 2000, published Jul. 12, 2001 as WO 01/49258 (Applicant—Acrymed).
Decision to grant a European Pat. issued on Apr. 21, 2006 for EP App. No. 990393.1, which claims priority to PCT/US00/35560, filed on Dec. 29, 2000, published Jul. 12, 2001 as WO 01/49258 (Applicant—Acrymed).
Reply to communication about intention to grant filed on Mar. 28, 2006 for EP App. No. 990393.1, which claims priority to PCT/US00/35560, filed on Dec. 29, 2000, published Jul. 12, 2001 as WO 01/49258 (Applicant—Acrymed).
Communication about intention to grant a European Pat. filed on Nov. 28, 2005 for EP App. No. 990393.1, which claims priority to PCT/US00/35560, filed on Dec. 29, 2000, published Jul. 12, 2001 as WO 01/49258 (Applican—Acrymed).
Reply to communication from the Examining Division filed on Aug. 30, 2005 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Feb. 22, 2005 for EP App. No. 990393.1, which claims priority to PCT/US00/35560, filed on Dec. 29, 2000, published Jul. 12, 2001 as WO 01/49258 (Applicant—Acrymed).

(56) References Cited

OTHER PUBLICATIONS

Reply to communication from the Examining Division filed on Apr. 1, 2004 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Feb. 13, 2004 for EP App. No. 990393.1, which claims priority to PCT/US00/35560, filed on Dec. 29, 2000, published Jul. 12, 2001 as WO 01/49258 (Applicant—Acrymed).
Reply to communication from the Examining Division filed on Jul. 24, 2003 for EP App. No. 990393.1, which claims priority to PCT/US00/35560, filed on Dec. 29, 2000, published Jul. 12, 2001 as WO 01/49258 (Applicant—Acrymed).
Communication from the Examining Division issued on Jan. 23, 2003 for EP App. No. 990393.1, which claims priority to PCT/US00/35560, filed on Dec. 29, 2000, published Jul. 12, 2001 as WO 01/49258 (Applicant—Acrymed).
Amendments before examination filed on Oct. 18, 2002 for EP App. No. 990393.1, which claims priority to PCT/US00/35560, filed on Dec. 29, 2000, published Jul. 12, 2001 as WO 01/49258 (Applicant—Acrymed).
Amendments before examination filed on Jul. 19, 2002 for EP App. No. 990393.1, which claims priority to PCT/US00/35560, filed on Dec. 29, 2000, published Jul. 12, 2001 as WO 01/49258 (Applicant—Acrymed).
PCT Intl. Search Report issued on Jul. 12, 2001 for PCT/US00/35560, filed on Dec. 29, 2000, published Jul. 12, 2001 as WO 01/49258 (Applicant—Acrymed; Inventors: Gibbins).
PCT Intl. Preliminary Examination Report issued on Apr. 2, 2002 for PCT/US00/35560, filed on Dec. 29, 2000, published Jul. 12, 2001 as WO 01/49258 (Applicant—Acrymed; Inventors: Gibbins).
Non-Final Rejection mailed on Feb. 15, 2011 for U.S. Appl. No. 09/752,939, filed on Dec 29, 2000 (Inventor—Gibbins).
Amendment Submitted/Entered with CPA/RCE filed on Jan. 18, 2011 for U.S. Appl. No. 09/752,939, filed on Dec. 29, 2000 (Inventor—Gibbins).
Notice of Appeal filed on Jun. 17, 2010 for U.S. Appl. No. 09/752,939, filed on Dec. 29, 2000 (Inventor—Gibbins).
Final Rejection issued on Feb. 25, 2010 for U.S. Appl. No. 09/752,939, filed on Dec. 29, 2000 (Inventor—Gibbins).
Amendment/Response After Non-Final Action filed on Dec. 3, 2009 for U.S. Appl. No. 09/752,939, filed on Dec. 29, 2000 (Inventor—Gibbins).
Non-Final Rejection issued on Jun. 4, 2009 for U.S. Appl. No. 09/752,939, filed on Dec. 29, 2000 (Inventor—Gibbins).
Amendment Submitted/Entered with CPA/RCE filed on Mar. 16, 2009 for U.S. Appl. No. 09/752,939, filed on Dec. 29, 2000 (Inventor—Gibbins).
Final Rejection issued on Sep. 18, 2008 for U.S. Appl. No. 09/752,939, filed on Dec. 29, 2000 (Inventor—Gibbins).
Amendment/Response After Non-Final Action filed on Apr. 28, 2008 for U.S. Appl. No. 09/752,939, filed on Dec. 29, 2000 (Inventor—Gibbins).
Non-Final Rejection issued on Dec. 28, 2007 for U.S. Appl. No. 09/752,939, filed on Dec. 29, 2000 (Inventor—Gibbins).
Amendment Submitted/Entered with CPA/RCE filed on Oct. 9, 2007 for U.S. Appl. No. 09/752,939, filed on Dec. 29, 2000 (Inventor—Gibbins).
Advisory Action (PTOL—303) issued on Sep. 4, 2007 for U.S. Appl. No. 09/752,939, filed on Dec. 29, 2000 (Inventor—Gibbins).
Amendment After Final Rejection filed on Aug. 6, 2007 for U.S. Appl. No. 09/752,939, filed on Dec. 29, 2000 (Inventor—Gibbins).
Final Rejection issued on Jun. 6, 2007 for U.S. Appl. No. 09/752,939, filed on Dec. 29, 2000 (Inventor—Gibbins).
Supplemental Response/Amendment filed on Apr. 3, 2007 for U.S. Appl. No. 09/752,939, filed on Dec. 29, 2000 (Inventor—Gibbins).
Amendment/Response After Non-Final Action filed on Feb. 14, 2007 for U.S. Appl. No. 09/752,939, filed on Dec. 29, 2000 (Inventor—Gibbins).
Examiner Interview Summary Record (PTOL—413) issued on Jan. 17, 2007 for U.S. Appl. No. 09/752,939, filed on Dec. 29, 2000 (Inventor—Gibbins).
Non-Final Rejection issued on Sep. 14, 2006 for U.S. Appl. No. 09/752,939, filed on Dec. 29, 2000 (Inventor—Gibbins).
Amendment Submitted/Entered with CPA/RCE filed on Aug. 7, 2006 for U.S. Appl. No. 09/752,939, filed on Dec. 29, 2000 (Inventor—Gibbins).
Amendment initialed by Examiner/Advisory Action (PTOL—303) issued on May 18, 2006 for U.S. Appl. No. 09/752,939, filed on Dec. 29, 2000 (Inventor—Gibbins).
Amendment After Final Rejection filed on May 8, 2006 for U.S. Appl. No. 09/752,939, filed on Dec. 29, 2000 (Inventor—Gibbins).
Final Rejection issued on Mar. 7, 2006 for U.S. Appl. No. 09/752,939, filed on Dec. 29, 2000 (Inventor—Gibbins).
Amendment/Response After Non-Final Action filed on Dec. 1, 2005 for U.S. Appl. No. 09/752,939, filed on Dec. 29, 2000 (Inventor—Gibbins).
Non-Final Rejection issued on Aug. 2, 2005 for U.S. Appl. No. 09/752,939, filed on Dec. 29, 2000 (Inventor—Gibbins).
Amendment Submitted/Entered with CPA/RCE filed on Jun. 15, 2005 for U.S. Appl. No. 09/752,939, filed on Dec. 29, 2000 (Inventor—Gibbins).
Advisory Action (PTOL—303) issued on Jun. 8, 2005 for U.S. Appl. No. 09/752,939, filed on Dec. 29, 2000 (Inventor—Gibbins).
Amendment After Final Rejection filed on Mar. 30, 2005 for U.S. Appl. No. 09/752,939, filed on Dec. 29, 2000 (Inventor—Gibbins).
Final Rejection issued on Dec. 16, 2004 for U.S. Appl. No. 09/752,939, filed on Dec. 29, 2000 (Inventor—Gibbins).
Amendment/Response After Non-Final Action filed on Sep. 16, 2004 for U.S. Appl. No. 09/752,939, filed on Dec. 29, 2000 (Inventor—Gibbins).
Non-Final Rejection issued on May 17, 2004 for U.S. Appl. No. 09/752,939, filed on Dec. 29, 2000 (Inventor—Gibbins).
Decision to Withdraw from Issue issued on Apr. 26, 2004 for U.S. Appl. No. 09/752,939, filed on Dec. 29, 2000 (Inventor—Gibbins).
Notice of Allowance issued on Jan. 23, 2003 for U.S. Appl. No. 09/752,939, filed on Dec. 29, 2000 (Inventor—Gibbins).
Amendment Submitted/Entered with CPA/RCE filed on Nov. 15, 2002 for U.S. Appl. No. 09/752,939, filed on Dec. 29, 2000 (Inventor—Gibbins).
Advisory Action (PTOL—303) issued on Nov. 19, 2002 for U.S. Appl. No. 09/752,939, filed on Dec. 29, 2000 (Inventor—Gibbins).
Amendment After Final Rejection filed on Oct. 15, 2002 for U.S. Appl. No. 09/752,939, filed on Dec. 29, 2000 (Inventor—Gibbins).
Final Rejection issued on Jul. 15, 2002 for U.S. Appl. No. 09/752,939, filed on Dec. 29, 2000, (Inventor—Gibbins).
Amendment/Response After Non-Final Action filed on Apr. 18, 2002 for U.S. Appl. No. 09/752,939, filed on Dec. 29, 2000 (Inventor—Gibbins).
Examiner Interview Summary Record (PTOL—413) issued on Apr. 11, 2002 for U.S. Appl. No. 09/752,939, filed on Dec. 29, 2000 (Inventor—Gibbins).
Non-Final Rejection issued on Dec. 18, 2001 for for U.S. Appl. No. 09/752,939, filed on Dec. 29, 2000 (Inventor—Gibbins).
Issue Notification issued on Dec. 20, 2006 for U.S. Appl. No. 10/441,141, filed on May 19, 2003 (Inventor—Gibbins).
Notice of Allowance/Examiner Interview Summary Record (PTOL—413) issued on Jul. 25, 2006 for U.S. Appl. No. 10/441,141, filed on May 19, 2003 (Inventor—Gibbins).
Amendment After Final Rejection filed on Jul. 5, 2006 for U.S. Appl. No. 10/441,141, filed on May 19, 2003 (Inventor—Gibbins).
Examiner Interview Summary Record (PTOL—413) issued on Jun. 28, 2006 for U.S. Appl. No. 10/441,141, filed on May 19, 2003 (Inventor—Gibbins).
Final Rejection issued on May 4, 2006 for U.S. Appl. No. 10/441,141, filed on May 19, 2003 (Inventor—Gibbins).
Amendment/Response After Non-Final Action filed on Feb. 14, 2006 for U.S. Appl. No. 10/441,141, filed on May 19, 2003 (Inventor—Gibbins).
Non-Final Rejection issued on Nov. 15, 2005 for U.S. Appl. No. 10/441,141, filed on May 19, 2003 (Inventor—Gibbins).

(56) References Cited

OTHER PUBLICATIONS

Preliminary Amendment filed on Apr. 12, 2003 for U.S. Appl. No. 10/441,141, filed on May 19, 2003 (Inventor—Gibbins).
Notification of Grant issued Feb. 5, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fifth Office Action filed on Jan. 7, 2010 for Chinese Pat. App. No. 03820077.5, which claims priority to PCT/US03/023851 filed Jul. 29, 2003, published Feb. 5, 2004 as WO 04/010952 (Applicant—Acrymed, Inc.) + claims in English.
Fifth Office Action issued on Oct. 23, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to fourth Office Action filed on Sep. 11, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.)—English translation only.
Fourth Office Action issued on Apr. 17, 2009 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to third Office Action filed on Aug. 27, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.) claims in English.
Third Office Action issued on Jun. 13, 2008 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to Second Office Action filed on Dec. 25, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.
Second Office Action issed for Aug. 10, 2007 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Response to first Office Action filed on Sep. 1, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.)—no translation available.
First Office Action issued on Apr. 21, 2006 for Chinese Pat. App. No. 03820077.5, which claims priority to PCT/US03/023851 filed Jul. 29, 2003, published Feb. 5, 2004 as WO 04/010952 (Applicant—Acrymed, Inc.).
Decision to Grant pursuant to Article 97(2) EPC issued on Dec. 2, 2010 for EP App. No. 3772113.1, which claims priority to PCT/US03/023851 filed Jul. 29, 2003, published Feb. 5, 2004 as WO 04/010952 (Applicant—Acrymed, Inc.).
Communication under Rule 71(3) EPC issued on Jun. 4, 2010 for EP App. No. 3772113.1, which claims priority to PCT/US03/023851 filed Jul. 29, 2003, published Feb. 5, 2004 as WO 04/010952 (Applicant—Acrymed, Inc.).
Letter during examination procedure after communication from the Examining Division filed on Jan. 19, 2010 for EP App. No. 3772113.1, which claims priority to PCT/US03/023851 filed Jul. 29, 2003, published Feb. 5, 2004 as WO 04/010952 (Applicant—Acrymed, Inc.).
Reply to communication from the Examining Division filed on Jan. 13, 2010 for EP App. No. 3772113.1, which claims priority to PCT/US03/023851 filed Jul. 29, 2003, published Feb. 5, 2004 as WO 04/010952 (Applicant—Acrymed, Inc.).
Communication from the Examining Division issued on Jul. 3, 2009 for EP App. No. 3772113.1, which claims priority to PCT/US03/023851 filed Jul. 29, 2003, published Feb. 5, 2004 as WO 04/010952 (Applicant—Acrymed, Inc.).
Reply to communication from the Examining Division filed on Jul. 15, 2008 for EP App. No. 3772113.1, which claims priority to PCT/US03/023851 filed Jul. 29, 2003, published Feb. 5, 2004 as WO 04/010952 (Applicant—Acrymed, Inc.).
Communication from the Examining Division issued on Jan. 10, 2008 for EP App. No. 3772113.1, which claims priority to PCT/US03/023851 filed Jul. 29, 2003, published Feb. 5, 2004 as WO 04/010952 (Applicant—Acrymed, Inc.).
Supplementary European search report issued on Dec. 14, 2006 for EP App. No. 3772113.1, which claims priority to PCT/US03/023851 filed Jul. 29, 2003, published Feb. 5, 2004 as WO 04/010952 (Applicant—Acrymed, Inc.).
Preliminary Amendment filed on Apr. 12, 2005 for EP App. No. 3772113.1, which claims priority to PCT/US03/023851 filed Jul. 29, 2003, published Feb. 5, 2004 as WO 04/010952 (Applicant—Acrymed, Inc.).
PCT Intl. Search Report issued on Aug. 27, 2004 for Intl. App. No. PCT/US03/023851 filed Jul. 29, 2003, published Feb. 5, 2004 as WO 04/010952 (Applicant—AcryMed, Inc.).
Issue Notification issued on Jul. 6, 2005 for U.S. Appl. No. 10/207,936, filed on Jul. 29, 2002 (Inventor—Maley, J. C.).
Amendment/Response—After Non-Final Rejection filed on Apr. 25, 2005 for U.S. Appl. No. 10/207,936, filed on Jul. 29, 2002 (Inventor—Maley, J. C.).
Office Communication issued on Mar. 30, 2005 for U.S. Appl. No. 10/207,936, filed on Jul. 29, 2002 (Inventor—Maley, J. C.).
Notice of Allowance and Fees Due (PTOL—85) with Examiner Interview Summary Record (PTOL—413) issued Feb. 16, 2005 for U.S. Appl. No. 10/207,936, filed on Jul. 29, 2002 (Inventor—Maley, J. C.).
Supplemental Amendment after Final Rejection issued on Jan. 28, 2005 for U.S. Appl. No. 10/207,936, filed on Jul. 29, 2002 (Inventor—Maley, J. C.).
Amendment After Final Rejection filed on Jan. 12, 2005 for U.S. Appl. No. 10/207,936, filed on Jul. 29, 2002 (Inventor—Maley, J. C.).
Final Rejection issued on Nov. 23, 2004 for U.S. Appl. No. 10/207,936, filed on Jul. 29, 2002 (Inventor—Maley, J. C.).
Response After Non-Final Rejection filed on Jul. 29, 2004 for U.S. Appl. No. 10/207,936, filed on Jul. 29, 2002 (Inventor—Maley, J. C.).
Non-Final Rejection issued on Apr. 29, 2004 for U.S. Appl. No. 10/207,936, filed on Jul. 29, 2002 (Inventor—Maley, J. C.).
Response After Non-Final Rejection filed on Jan. 22, 2004 for U.S. Appl. No. 10/207,936, filed on Jul. 29, 2002 (Inventor—Maley, J. C.).
Non-Final Rejection issued on Oct. 22, 2003 for U.S. Appl. No. 10/207,936, filed on Jul. 29, 2002 (Inventor—Maley, J. C.).
Response After Non-Compliant Amendment filed on Jun. 2, 2010 for U.S. Appl. No. 10/630,627, filed Jul. 29, 2003 (Inventor—Maley, J.C.).
Amendment Submitted/Entered with CPA/RCE filed on Apr. 27, 2010 for U.S. Appl. No. 10/630,627, filed Jul. 29, 2003 (Inventor—Maley, J.C.).
Final Rejection issued on Dec. 3, 2009 for U.S. Appl. No. 10/630,627, filed Jul. 29, 2003 (Inventor—Maley, J.C.).
Response After Non-Final Rejection filed on Jul. 20, 2009 for U.S. Appl. No. 10/630,627, filed Jul. 29, 2003 (Inventor—Maley, J.C.).
Non-Final Rejection issued on Feb. 19, 2009 for U.S. Appl. No. 10/630,627, filed Jul. 29, 2003 (Inventor—Maley, J.C.).
Amendment Submitted/Entered with CPA/RCE filed on Nov. 26, 2008 for U.S. Appl. No. 10/630,627, filed Jul. 29, 2003 (Inventor—Maley, J.C.).
Final Rejection issued on Jun. 26, 2008 for U.S. Appl. No. 10/630,627, filed Jul. 29, 2003 (Inventor—Maley, J.C.).
Response After Non-Final Rejection filed on Feb. 7, 2008 for U.S. Appl. No. 10/630,627, filed Jul. 29, 2003 (Inventor—Maley, J.C.).
Non-Final Rejection issued on Sep. 7, 2007 for U.S. Appl. No. 10/630,627, filed Jul. 29, 2003 (Inventor—Maley, J.C.).
Amendment Submitted/Entered with CPA/RCE filed on Jun. 22, 2007 for U.S. Appl. No. 10/630,627, filed Jul. 29, 2003 (Inventor—Maley, J.C.).
Advisory Action (PTOL—303) issued on May 17, 2007 for U.S. Appl. No. 10/630,627, filed Jul. 29, 2003 (Inventor—Maley, J.C.).
Amendment After Final Rejection filed on Apr. 23, 2007 for U.S. Appl. No. 10/630,627, filed Jul. 29, 2003 (Inventor—Maley, J.C.).
Final Rejection issued on Feb. 23, 2007 for U.S. Appl. No. 10/630,627, filed Jul. 29, 2003 (Inventor—Maley, J.C.).

(56) References Cited

OTHER PUBLICATIONS

Response After Non-Final Rejection filed on Nov. 21, 2006 for U.S. Appl. No. 10/630,627, filed Jul. 29, 2003 (Inventor—Maley, J.C.).
Non-Final Rejection issued on Aug. 24, 2006 for U.S. Appl. No. 10/630,627, filed Jul. 29, 2003 (Inventor—Maley, J.C.).
Response to Election / Restriction Filed on Jun. 23, 2006 for U.S. Appl. No. 10/630,627, filed Jul. 29, 2003 (Inventor—Maley, J.C.).
Restriction/Election Requirement issued on May 23, 2006 for U.S. Appl. No. 10/630,627, filed Jul. 29, 2003 (Inventor—Maley, J.C.).
Response to First Office Action filed on Jul. 9, 2009 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.)—Proposed Claims in English.
First Office Action issued on Dec. 26, 2008 for Chinese Pat. App. No. 200580028750.9, which claims priority to Intl. App. No. PCT/US/05/027260 filed Aug. 1, 2005, published Feb. 9, 2006 as WO 06/015317 (Applicant—Acrymed, Inc.).
Amended claims filed on Feb. 26, 2007 for EP App. No. 05778379.7, which claims priority to Intl. App. No. PCT/US05/027260 filed Aug. 1, 2005, published Feb. 9, 2006 as WO 06/015317 (Applicant—Acrymed, Inc.).
Response to Examiners Report filed on Jun. 29, 2011 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Examiners Report issued on Jun. 29, 2010 for Indian Pat. App 735/KOLNP/2007, which claims priority to Intl. Pat. App. No. PCT/US05/027260, filed on Aug. 1, 2005, published on Mar. 9, 2006 as WO 06/015317 (Applicant—Acrymed, Inc.).
Intl. Preliminary Report on Patentability issued on Jan. 30, 2007 for Intl. App. No. PCT/US05/027260 filed Aug. 1, 2005, published Feb. 9, 2006 as WO 06/015317 (Applicant—Acrymed, Inc.).
Intl. Search Report with Written Opinion issued on Apr. 28, 2006 for Intl. App. No. PCT/US05/027260 filed Aug. 1, 2005, published Feb. 9, 2006 as WO 06/015317 (Applicant—Acrymed, Inc.).
Protest Documents from 3rd Party filed on Apr. 3, 2009 for U.S. Appl. No. 11/572,899, filed May 13, 2008 (Inventor—Karandikar et al.).
Preliminary Amendment filed on Jan. 29, 2007 for U.S. Appl. No. 11/572,899, filed May 13, 2008 (Inventor—Karandikar et al.).
Intl. Preliminary Report on Patentability issued on Jan. 30, 2007 for Intl. App. No. PCT/US05/027261 filed Aug. 1, 2005, published Mar. 9, 2006 as WO 06/026026 (Applicant—Acrymed, Inc.).
Intl. Search Report with Written Opinion issued on Apr. 28, 2006 for Intl. App. No. PCT/US05/027261 filed Aug. 1, 2005, published Mar. 9, 2006 as WO 06/026026 (Applicant—Acrymed, Inc.).
Notice of Acceptance issued on Jan. 24, 2011 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Response to Examiners Report filed on Dec. 13, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Examiner's First Report issued on Feb. 19, 2010 for AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
AU Divisional App. No. 2011202034 filed on May 3, 2011 from AU Pat. App. No. 2005280443, which claims priority to Intl. Pat. App. No. PCT/US05/027261, filed on Aug. 1, 2005, published on Mar. 9, 2006 as WO 06/02026 (Applicant—Acrymed, Inc.).
Second Office Action (Text Portion) issued on Jun. 7, 2011 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Office Action filed on Jul. 9, 2009 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
First Office Action issued on Dec. 26, 2008 for Chinese Pat. App. No. 200580028877.0, which claims priority to Intl. Pat. App. No. PCT/US05/027261, filed on Aug. 1, 2005, published on Mar. 9, 2006 as WO 06/02026 (Applicant—Acrymed, Inc.).
Response to Examiner's Report filed on Jun. 30, 2011 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.)—proposed amendments only.
Examiner's Report issued on Jul. 2, 2010 for Indian Pat. App 397/KOLNP/2007, which claims priority to Intl. Pat. App. No. PCT/US05/027261, filed on Aug. 1, 2005, published on Mar. 9, 2006 as WO 06/02026 (Applicant—Acrymed, Inc.).
Official Action issued on Mar. 1, 2011 for JP App. No. 2007-523881, which claims priority to Intl. Pat. App. No. PCT/US05/027261, filed on Aug. 1, 2005, published on Mar. 9, 2006 as WO 06/02026 (Applicant—Acrymed, Inc.)—translation included.
Notice of Acceptance issued on Apr. 26, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Apr. 21, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Feb. 2, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response to Examination Report filed on Jan. 20, 2011 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Further Examination Report issued on Jul. 8, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Response and Amended Pages filed on Jun. 28, 2010 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examination Report issued on Apr. 24, 2009 for New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
NZ Divisional App. No. 592438 filed on Apr. 21, 2011 from New Zealand Pat. App. No. 552928, which claims priority to Intl. Pat. App. No. PCT/US05/027261, filed on Aug. 1, 2005, published on Mar. 9, 2006 as WO 06/02026 (Applicant—Acrymed, Inc.).
Examiner's first report issued on Oct. 18, 2010 for Australian Pat. App. No. 2007215443, which claims priority to PCT/US07/03390, filed Feb. 8, 2007, published on Aug. 23, 2007 as WO 07/095058 (Applicant—Acrymed, Inc.).
Response to Second Office Action filed on Jun. 7, 2011 for Chinese Pat. App. No. 200780012684.5, which claims priority to PCT/US07/003390 filed on Feb. 8, 2007 (Applicant—AcryMed, Inc.)—No Translation.
Second Office Action issued Mar. 23, 2011 for Chinese Pat. App. No. 200780012684.5, which claims priority to PCT/US07/003390 filed on Feb. 8, 2007 (Applicant—AcryMed, Inc.).
Response to First Office Action filed on Feb. 28, 2011 for Chinese Pat. App. No. 200780012684.5, which claims priority to PCT/US07/003390 filed on Feb. 8, 2007 (Applicant—AcryMed, Inc.)—Proposed amended claims in English.
First Office Action issued Oct. 13, 2010 for Chinese Pat. App. No. 200780012684.5, which claims priority to PCT/US07/003390 filed on Feb. 8, 2007 (Applicant—AcryMed, Inc.).
Claim amendments filed on Sep. 4, 2008 for EP App. No. 07750244.1, which claims priority to PCT/US07/03390, filed Feb. 8, 2007, published on Aug. 23, 2007 as WO 07/095058 (Applicant—Acrymed, Inc.).

(56) References Cited

OTHER PUBLICATIONS

PCT Preliminary Report on Patentability issued on Aug. 12, 2008 for Intl. Pat. App. No. PCT/US07/03390, filed Feb. 8, 2007, published on Aug. 23, 2007 as WO 07/095058 (Applicant—Acrymed, Inc.).
PCT Intl. Search Report with Written Opinion issued on Dec. 21, 2007 for Intl. Pat. App. No. PCT/US07/03390, filed Feb. 8, 2007, published on Aug. 23, 2007 as WO 07/095058 (Applicant—Acrymed, Inc.).
Amendment Entered with CPA/RCE filed on Apr. 22, 2011 for U.S. Appl. No. 11/704,167, filed Feb. 8, 2007 (Inventors—Karandikar et al.).
Final Rejection issued on Dec. 22, 2010 for U.S. Appl. No. 11/704,167, filed Feb. 8, 2007 (Inventors—Karandikar et al.).
Response after Non-Final Action mailed Oct. 28, 2010 for U.S. Appl. No. 11/704,167, filed Feb. 8, 2007 (Inventors—Karandikar et al.).
Non-Final Rejection issued on May 28, 2010 for U.S. Appl. No. 11/704,167, filed Feb. 8, 2007 (Inventors—Karandikar et al.).
Response to Election / Restriction filed on Apr. 30, 2010 for U.S. Appl. No. 11/704,167, filed Feb. 8, 2007 (Inventors—Karandikar et al.).
Restriction/Election Requirement issued on Mar. 30, 2010 for U.S. Appl. No. 11/704,167, filed Feb. 8, 2007 (Inventors—Karandikar et al.).
Preliminary Amendments filed on Nov. 24, 2008 for EP 07755996.1 which claims priority to PCT/US07/009997, filed on Apr. 25, 2007, published on Nov. 8, 2007 as WO 07/127236 (Applicant—Acrymed, Inc.).
Intl. Search Report w/ Written Opinion issued on Aug. 25, 2008 for Intl. Pat. App. No. PCT/US07/009997, filed on Apr. 25, 2007, published on Nov. 8, 2007 as WO 07/127236 (Applicant—Acrymed, Inc.).
Intl. Preliminary Report on Patentability issued on Oct. 28, 2008 for Intl. Pat. App. No. PCT/US07/009997, filed on Apr. 25, 2007, published on Nov. 8, 2007 as WO 07/127236 (Applicant—Acrymed, Inc.).
Final Rejection issued on Jun. 23, 2011 for U.S. Appl. No. 11/789,701, filed Apr. 25, 2007 (Inventors—McMaken et al.).
Response after Non-Final Rejection filed on Apr. 5, 2011 for U.S. Appl. No. 11/789,701, filed Apr. 25, 2007 (Inventors—McMaken et al.).
Non-Final Rejection issued on Oct. 5, 2010 for U.S. Appl. No. 11/789,701, filed Apr. 25, 2007 (Inventors—McMaken et al.).
Amendment Entered with CPA/RCE filed on Mar. 31, 2010 for U.S. Appl. No. 11/789,701, filed Apr. 25, 2007 (Inventors—McMaken et al.).
Final Rejection issued on Oct. 5, 2009 for U.S. Appl. No. 11/789,701, filed Apr. 25, 2007 (Inventors—McMaken et al.).
Response After Non-Final Rejection filed Jun. 8, 2009 for U.S. Appl. No. 11/789,701, filed Apr. 25, 2007 (Inventors—McMaken et al.).
Non-Final Rejection issued on Jan. 26, 2009 for U.S. Appl. No. 11/789,701 filed Apr. 25, 2007 (Inventors—McMaken et al.).
Response to Election / Restriction filed on Dec. 15, 2008 for U.S. Appl. No. 11/789,701, filed Apr. 25, 2007 (Inventors—McMaken et al.).
Requirement for Restriction/Election issued on Nov. 14, 2008 for U.S. Appl. No. 11/789,701, filed Apr. 25, 2007 (Inventors—McMaken et al.).
Intl. Preliminary Report on Patentability issued on May 24, 2011 for Intl. Pat. App. No. PCT/US09/065764, filed on Nov. 24, 2009, published on May 27, 2010 as WO 10/060094 (Applicant—Kimberly-Clark, Worldwide Inc.).
Intl. Search Report with Written Opinion issued on Apr. 28, 2010 for Intl. Pat. App. No. PCT/US09/065764, filed on Nov. 24, 2009, published on May 27, 2010 as WO 10/060094 (Applicant—Kimberly-Clark, Worldwide Inc.).
Reply to Communication from Examining Division filed on Jun. 16, 2011 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division issued on Feb. 8, 2011 for EP App. No. 05797894.2, which claims priority to PCT/US05/033600, filed Sep. 19, 2005, published on Mar. 30, 2006 as WO 06/034249 (Applicant—Acrymed, Inc.).
Reply to Communication from Examining Division filed on Jun. 23, 2009 for EP App. No. 05797894.2, which claims priority to PCT/US05/033600, filed Sep. 19, 2005, published on Mar. 30, 2006 as WO 06/034249 (Applicant—Acrymed, Inc.).
Communication from Examining Division issued on Dec. 17, 2008 for EP App. No. 05797894.2, which claims priority to PCT/US05/033600, filed Sep. 19, 2005, published on Mar. 30, 2006 as WO 06/034249 (Applicant—Acrymed, Inc.).
Supplemental European Search Report and Opinion issued on Oct. 21, 2008 for EP App. No. 05797894.2, which claims priority to PCT/US05/033600, filed Sep. 19, 2005, published on Mar. 30, 2006 as WO 06/034249 (Applicant—Acrymed, Inc.).
Amendments before examination filed on Apr. 18, 2007 for EP App. No. 05797894.2, which claims priority to PCT/US05/033600, filed Sep. 19, 2005, published on Mar. 30, 2006 as WO 06/034249 (Applicant—Acrymed, Inc.).
Intl. Preliminary Report on Patentability issued on May 1, 2007 for Intl. Pat. App. No. PCT/US05/033600, filed Sep. 19, 2005, published Mar. 30, 2006 as WO 06/034249 (Applicant—Acrymed, Inc.).
Intl. Search Report with Written Opinion issued on Apr. 18, 2007 for Intl. Pat. App. No. PCT/US05/033600, filed on Sep. 19, 2005, published on Mar. 30, 2006 as WO 06/034249 (Applicant—Acrymed, Inc.).
Final Rejection issued on Jun. 13, 2011 for U.S. Appl. No. 11/663,236, filed Mar. 19, 2007 (Karandikar et al.).
Response after Non-Final Action filed on Apr. 12, 2011 for U.S. Appl. No. 11/663,236, filed Mar. 19, 2007 (Karandikar et al.).
Non-Final Rejection issued on Dec. 13, 2010 for U.S. Appl. No. 11/663,236, filed Mar. 19, 2007 (Karandikar et al.).
Response to Restriction/Election Requirement filed on Sep. 23, 2010 for U.S. Appl. No. 11/663,236, filed Mar. 19, 2007 (Karandikar et al.).
Restriction/Election Requirement issued on Jun. 23, 2010 for U.S. Appl. No. 11/663,236, filed Mar. 19, 2007 (Karandikar et al.).
Preliminary Amendment filed on Mar. 19, 2007 for U.S. Appl. No. 11/663,236, filed Mar. 19, 2007 (Karandikar et al.).
Third Office Action issued Jul. 7, 2011 for Chinese Pat. App. No. 200780012684.5, which claims priority to PCT/US07/003390 filed on Feb. 8, 2007 (Applicant—AcryMed, Inc.).
Non-Final Rejection issued on Jun. 28, 2011 for U.S. Appl. No. 10/630,627, filed Jul. 29, 2003 (Inventor—Maley, J.C.).
Grier, N., "Silver and Its Compounds," Disinfection, Sterilization, and Preservation, 3rd Edition. Seymour S. Block, ed., Lea & Febiger, Philadelphia, 1983; Chapter 18, pp. 375-389.
Russel A. and Hugo, W., "Antimicrobial Activity and Action of Silver," Progress in Medicinal Chemistry, vol. 31, G-.P. Ellis & D.K. Luscombe, ed., Elsevier Science B.V., 1994; pp. 351-370.
Notice of Allowance issued on May 12, 2011 for U.S. Appl. No. 12/510,651, filed on Jul. 28, 2009 (Inventor—Gibbins).
Amendment/Response After Non-Final Reject/Terminal Disclaimer filed on Apr. 4, 2011 for U.S. Appl. No. 12/510,651, filed on Jul. 28, 2009 (Inventor—Gibbins).
Non-Final Rejection issued on Jan. 5, 2011 for U.S. Appl. No. 12/510,651, filed on Jul. 28, 2009 (Inventor—Gibbins).
Preliminary Amendment filed on Oct. 28, 2009 for U.S. Appl. No. 12/510,651, filed on Jul. 28, 2009 (Inventor —Gibbins).
Response to Restriction Requirement filed on Aug. 9, 2011 for U.S. Appl. No. 11/572,899, filed May 13, 2008 (Inventor—Karandikar et al.).
Restriction requirement issued on Jun. 28, 2011 for U.S. Appl. No. 11/572,899, filed May 13, 2008 (Inventor—Karandikar et al.).
Supplemental European Search Report issued May 23, 2011 for EP App. No. 07750244.1, which claims priority to PCT/US07/03390, filed Feb. 8, 2007, published on Aug. 23, 2007 as WO 07/095058 (Applicant—Acrymed, Inc.).
Non-Final Rejection issued on Jun. 30, 2011 for U.S. Appl. No. 11/704,167, filed Feb. 8, 2007 (Inventors—Karandikar et al.).

(56) References Cited

OTHER PUBLICATIONS

Amendment/Response After Non-Final Action filed on Aug. 9, 2011 for U.S. Appl. No. 09/752,939, filed on Dec. 29, 2000 (Inventor—Gibbins).

Non-Final Rejection issued on Aug. 17, 2011 for U.S. Appl. No. 12/510,651, filed on Jul. 28, 2009 (Inventor—Gibbins).

Response after Non-Final Rejection filed on Aug. 26, 2011 for U.S. Appl. No. 12/510,651, filed on Jul. 28, 2009 (Inventor—Gibbins).

* cited by examiner

ANTIMICROBIAL SILVER COMPOSITIONS

RELATED APPLICATIONS

The present application claims the priority of U.S. Provisional Patent Application Ser. No. 60/592,687, filed Jul. 30, 2004, which is herein incorporated in its entirety.

FIELD OF THE INVENTION

The invention relates to antimicrobial compositions comprising silver nanoparticles, their preparation, the application of the compositions to surfaces and methods of preparing the devices.

BACKGROUND OF THE INVENTION

Silver derives its broad spectrum antimicrobial activity from the ability of silver ions to bind irreversibly to a variety of nucleophilic groups commonly available in cells of bacteria, viruses, yeast, fungi and protozoa. Binding to cellular components disrupts the normal reproduction and growth cycle resulting in death of the cell. Capitalizing on its potent activity, silver and its compounds have been incorporated over the past several decades in a variety of wound care products such as dressings, hydrogels, hydrocolloids, creams, gels, lotions, catheters, sutures, and bandages.

The preferred form of silver in antimicrobial products has been its compounds or salts as the metallic form of the element itself lacks therapeutically effective oligodynamic action. The compounds or salts upon contact with an aqueous medium ionize to yield silver ions that become available for antimicrobial action. The majority of silver compounds are also photosensitive or heat sensitive making their utilization in stable commercial products challenging. Alternatively, silver metal has been deposited as thin films on antimicrobial catheters and wound dressings by a vacuum sputter process or by electroplating to form an antimicrobial surface. The mechanism of silver metal containing products is thought to involve silver oxide that forms on its surface. After coming in contact with fluids, silver oxide which is weakly soluble in water, releases therapeutically effective amount of silver ions. Because the deposited silver has a small surface area, it releases relatively few ions and therefore can provide only limited antimicrobial activity and effective long term sustained release can be quite difficult. Sustained release activity is required for long term care of patients undergoing procedures such as catheterization and pain management. To some extent, this difficulty can be overcome by increasing the silver loading in the product but this approach leads to an increased risk of cytotoxicity to the mammalian cells and often causes staining of areas contacting the product. Additionally, the manufacture of such devices is also expensive as it involves vacuum sputtering, an operation that requires specialized equipment.

One solution to improving silver ion release from silver metal bearing surfaces without increasing loading is to increase the surface area of available silver on a per unit mass basis. Such an approach would permit very large increase in surface area as the particles sizes approach nanometer range. Recently, several inventors have claimed the production of silver in the form of dry nanoparticles where sizes approach the order of nanometers. The silver nanoparticles allow for very large surfaces per unit mass as surface area per unit volume (or mass) is inversely proportional to its diameter. The large surface area allows for surface oxide layers that in turn improve the silver ion release upon contact with water. Unfortunately, it is known that very fine pure metal particles as powders in dry state are potential fire hazard if exposed to air. Air exposure ignites the particles due to very rapid oxidation reactions that are highly exothermic.

Other processes for silver particles have been based on thermal evaporation of pure metal under vacuum. The processes are energy intensive, require expensive equipment, demand high maintenance and the particles produced require some form of passivation of surfaces to reduce fire and explosion risk. Additional steps such as passivation increase costs and may adversely affect the antimicrobial activity possibly requiring greater amount of silver loading to achieve the minimum inhibitory levels. The dry processes suffer from exposure hazard to the manufacturing personnel as very little is known about the effects of silver nanoparticles in different environments. Further, the silver nanoparticles produced in dry form are present as agglomerates that require re-dispersion, which is an energy intensive process and seldom completely effective.

In summary, neither the dry processes nor wet methods used in known processes offer a simple, inexpensive and non-hazardous method for providing silver nanoparticle compositions that are used to easily render a variety of surfaces antimicrobial.

Therefore, there is a need for antimicrobial compositions comprising silver nanoparticles that can be made by methods that are scalable to high volume manufacturing and utilize chemicals that are relatively non-hazardous. Furthermore the utility of antimicrobial nanoparticles is increased if they are in a form that can be incorporated into compositions or applied directly to surfaces regardless of the shape and contours of devices. Such a form would be in a fluid that is easily dispensed or used as an immersion bath for the devices. Further, such antimicrobial compositions render surfaces treated with them to possess antimicrobial action, including difficult to reach surfaces, such as those of medical devices and do not waste any silver.

SUMMARY OF THE INVENTION

The present invention comprises antimicrobial compositions comprising stabilized silver nanoparticles that are formed in a fluid environment and includes methods of making and using these compositions. A composition of silver nanoparticles of the present invention is generally in the range of 0.1 to 100 nm with approximately 50 nm being the largest proportion of a distribution of nanoparticles.

The compositions of the present invention also can be made with aqueous or non-aqueous solvents. The non-aqueous compositions of the present invention possess good shelf life and can be utilized in rendering moisture sensitive articles antimicrobial. Non-aqueous compositions may be based on solvents that have a range of boiling points from room temperature to above 300° C. for some thermal transfer fluids. It is generally recognized that it is difficult to produce silver nanoparticles in a non-aqueous medium, especially at high concentrations. Non-aqueous silver nanoparticle compositions may be made by extracting the nanoparticles from aqueous compositions into a non-aqueous phase. As used herein, non-aqueous means organic media that are generally immiscible with water over large composition ranges as are generally understood by those skilled in the art. The amount of silver content in non-aqueous compositions can be adjusted by choosing the desired amount of silver in the preparation of the aqueous composition, followed by extraction of the aqueous composition.

It is thought that the effectiveness of the antimicrobial application on devices is dependent upon the amount and form of the silver associated with the device. Different amounts of silver loading on surfaces of devices can be achieved, for example, by successive multiple treatments or continued immersion of the treated object in a single composition until the desired loading amount is reached. In general, the compositions are not viscous which allows for ease in coating many preformed articles uniformly and thus rendering them antimicrobial. Often the techniques such as thermal evaporation or plasma deposition processes are unsuitable to achieve uniform deposition of silver inside of thin bore tubes with large aspect (length to diameter) ratio because of the inherent concentration gradients. The compositions of the present invention do not face such difficult as the nanoparticle compositions can penetrate and deposit silver due to their low viscosities and low surface tensions.

Medical devices which may be made antimicrobial using the methods and compositions herein include, but are not limited to, catheters (venous, urinary, Foley or pain management or variations thereof), stents, abdominal plugs, feeding tubes, cotton gauzes, fibrous wound dressings (sheet and rope made of alginates, CMC or mixtures thereof, crosslinked or non-crosslinked cellulose), foam materials, collagen or protein matrices, hemostatic materials, adhesive films, contact lenses, lens cases, bandages, sutures, hernia meshes, mesh based wound coverings, ostomy and other wound products, hydrogels, creams, lotions, gels (water based or oil based), emulsions, liposomes, microspheres, ointments, adhesives, porous inorganic supports such as titania and those described in U.S. Pat. No. 4,906,466, chitosan or chitin powders, metal based orthopedic implants, metal screws and plates, synthetic fabrics, nylon fabrics or its blends with other fabric making materials (silk, rayon, wool, polyester, acrylic, acetate), and fabrics impregnated with silver nanoparticles are contemplated by the present invention. Other devices, including dental and veterinary products and non-medical devices, made of silicone, polyurethanes, polyamides, acrylates, ceramics and other thermoplastic materials may be treated with the nanoparticles compositions of present invention.

Various coating compositions for different polymeric or metal surfaces that can be prepared from liquid compositions are also contemplated by the present invention. Such coating compositions can be hardened by solvent loss or cured by thermal or radiation exposure. Another aspect of the present invention comprise compositions comprising the compositions taught herein and other active agents and antimicrobial agents such as glasses and zeolites similar to those disclosed in U.S. Pat. No. 5,049,139 and U.S. Pat. No. 6,248,342 and incorporated by reference in their entirety.

Different methods are taught to treat the devices with the compositions of the present invention. A method comprises making compositions, contacting the composition and the device surfaces for a sufficient period of time and rinsing the device of the excess of the composition and drying the device. Several modifications of the disclosed method are possible without departing from the scope of the invention.

Devices may also be treated with non-aqueous silver compositions. Often the devices comprising alginates or CMC either as fibers or foam fibers and are not suitable for treatment using aqueous compositions as they become unusable after contact with water. Instead such devices can be conveniently treated with non-aqueous silver compositions by dipping method or spraying the compositions on the substrates. After removal of the solvent by evaporation under normal conditions or by vacuum, the surfaces of the devices carry a deposition of silver nanoparticles and become antimicrobial. Non-aqueous compositions can also be used to treat medical devices made from other polymers so long as the non-aqueous solvent is a non-solvent for that polymer or does not diffuse into the device to cause gelling, swelling or damage that renders them unsuitable for their intended use.

Medical or cosmetic amorphous formulations in the form of creams, lotions, ointments, gels, shampoos, conditioners, moisturizers, or antiperspirants can be readily prepared by blending in the antimicrobial silver compositions. Preparations such as the creams, lotions, gels, shampoos, conditioners and emulsions, antiperspirants are known to those ordinarily skilled in the art.

Silver nanoparticles may be formed in situ on a surface, such as the surface of a medical device. For instance, a method comprises providing a suspension comprising finely dispersed particles of a silver compound in which the device is immersed and the treating the composition with a reducing agent for a specified period of time or until all of the silver compound is reduced to silver nanoparticles that are predominantly mono-disperse so that they can firmly attach to the surface of the device. An aspect of the devices rendered antimicrobial by the methods herein is that the antimicrobial activity is not adversely affected during sterilization by common processes such as steam sterilization, ETO, electron beam and gamma radiation.

The nanoparticle compositions of the present invention can be used in other compositions where an antimicrobial environment is desired or where a reduction in microbial growth, or a reduction in odor would be useful. For example, the silver nanoparticles compositions may be added to paints, cosmetics, on wound dressings to control of odor from wound exudates, in dental compositions, in products used in bowel or vascular surgery, oral hygiene products, bathroom products, textile products, coatings, natural or synthetic polymers adhesives, paint products, polymer films, paper, leather, rubber and plastic articles. Unfinished and finished articles such as yarn or bolts of cloth may also be rendered antimicrobial.

Other applications for silver nanoparticle comprising compositions of the present invention contemplated are in the catalysis of oxidation of olefins, in catalytic reduction of hydrogen peroxide, as polishing slurries, dissipation of static charge from surfaces, increasing thermal conductivity of liquids, increasing electrical conductivity, in the preparation of radio frequency or similar radiation shields, and in analytical chemistry for surface enhanced Raman spectroscopy.

The compositions of the present invention are made by relatively straightforward methods, are water or solvent based, possess long shelf life (nearly a year) and can be made in large volumes and thus, the production process is scalable. The components of the compositions are relatively non-hazardous and can be washed off from treated surfaces to leave behind the antimicrobial silver nanoparticles. The compositions may be optically clear, non-viscous and may be stored for long periods of time at room temperature, require no special storage conditions, are resistant to discoloration when exposed to light, are thermally stable, fairly stable to acids and bases, and withstand thermal cycling and conventional centrifugation.

The compositions of the present invention, in either aqueous or non-aqueous formulations, may comprise varying amounts of silver, referred to herein as silver loading. Different amounts of silver content in the compositions can be achieved by determining the amount of silver compound used during the formation of the composition. Silver content of the compositions can be adjusted by a variety of methods. One can initially select the desired amount of the silver compound or dilute the composition having a known amount of silver nanoparticles. The diluent added may comprise water and may or may not comprise other ingredients such as surfactant or other miscible solvents. The silver content may be increased by concentrating the compositions by removal of solvent by means known to those ordinarily skilled in the art. In fact one can remove most of the solvent from the compositions, and re-dilute to regenerate the composition to the original volume without causing the silver nanoparticles to agglomerate.

The compositions of the present invention may comprise silver nanoparticles and other silver compounds. The silver compounds from which the silver nanoparticles of the present invention are made may comprise any type of anion, including inorganic or organic anions. Such anions may be organic, and include, but are not limited to those taught in a co-pending application, filed concurrently herewith, entitled, Antimicrobial Devices and Compositions, such as imidic organic anions, saccharine and saccharinates.

The nanoparticles of the present invention are made by combining a solvent, which may be water or a mixture of water and known miscible organic solvents, generally less than 35% v/v alcohol, a stabilizer which may be a polymer and/or a surfactant, a silver compound and a reducing agent. A surfactant capable of preventing agglomeration of the particles, such as a anionic, non-ionic or amphoteric surfactant, may be used, but those from polysorbate family are preferred. Known water miscible organic solvents include lower straight chain ($C_1$-$C_6$) or branched alcohols, acetone, tetrahydrofuran, formamide, dimethyl formamide, acetamide and other similar solvents. The reducing agent, which is thought to trigger the nanoparticle formation in solution, includes monomeric or polymeric organic chemical compounds comprising one or more electron donating groups with substituted or non-substituted nitrogen atoms, including but not limited to, triethanolamine and N,N,N',N' tetramethyl ethylene diamine (TEMED).

The aqueous silver nanoparticle compositions may be stabilized with a polymer. The polymer may be a homopolymer or copolymer and may be synthetic or natural and is usually water-soluble. Stabilizing action is achieved by steric hindrance due to the presence of polymer chains in such a way that the particle agglomeration and growth is suppressed. In polymer stabilized compositions generally the surfactant may or may not be used. Polymers possessing some polarity and water solubility are generally suitable for use in the compositions of the present invention. Non-limiting examples of polymers are those comprising amide or substituted amides, primary, secondary or tertiary nitrogen, and urethane moiety in the main chain or side chains.

In general, an example of a method for making a composition of the present invention comprises mixing one of a surfactant or a stabilizing polymer with a silver compound that is a compound such as a salt that can ionize to a silver cation and an anion in solution, tetramethyl ethylene diamine (TEMED) and water. This mixture is heated to initiate the silver nanoparticle formation, which is indicated by a yellow color and a measurement of a characteristic absorption peak in the UV/VIS spectrum. The silver nanoparticles may form at any temperature, from sub zero to room temperature to very high temperatures. It will be recognized that a balance between temperature and time can be used to control the silver nanoparticle formation process. Heating the mixture can generally be used to accelerate the rate of nanoparticle formation.

Treated surfaces take on an amber coloration that increases in intensity as more silver nanoparticles deposit. An aspect of the present invention comprises a method for creating a more whitened surface appearance for treated surfaces by applying to silver nanoparticle treated surface a hydrogen peroxide solution, washing off the solution, and drying the surface.

Antimicrobial silver compositions have utility not only in imparting an antimicrobial property to medical devices but can also reduce the odor causing bacteria, in items, including, but not limited to, hosiery products such as panty hose, socks, undergarments, swim wear products, outfits for hunters and trekkers, ski wear products, athletic wear products for a variety of sports, for disinfection purposes, it can be used in household or consumer products such as bathroom or kitchen products, filters for humidifiers, shower curtains, cutting boards, sink sponges, bath sponges, and pumice stones. Compositions of the present invention can be also be used to treat a foam or porous matrix that can be added to un-potable water to disinfect it. In the construction industry, for the control of mold and mildew in homes the wooden structures during construction may be sprayed with the antimicrobial silver compositions of the present invention.

The present invention also contemplates antimicrobial radioactive silver (for example $^{110m}Ag^+$) compositions and their methods of preparation and their use in articles that may be used as tracers. The antimicrobial silver compositions of the present invention can also be the starting material for producing dry silver nano-silver powders suitable for material science and metallurgical applications.

DETAILED DESCRIPTION OF THE INVENTION

The present invention comprises compositions comprising silver nanoparticles and methods for making and using such compositions. The compositions comprising silver nanoparticles may comprise aqueous solutions or non-aqueous solutions. The nanoparticles of the compositions are generally uniform in size, generally spherical, and can be preformed or made in situ. Methods for using the compositions include, but are not limited to providing antimicrobial characteristics to surfaces, compositions and materials, providing odor control to compositions and materials, and for use in manufacturing and other applications. An aspect of the invention is to provide medical devices that are antimicrobial for an extended period of time and to provide methods for coating or treating medical devices and materials to render them antimicrobial, and to provide a range of amounts of silver to surfaces.

The compositions of the present invention are made from chemicals that are relatively non-hazardous. Their handling and safety risk is well documented. The use of TEMED is quite well accepted in the preparation of polyacryamide gels in electrophoresis. With proper precaution, its handling and use is considered safe by trained professionals. The compositions comprising silver nanoparticles of the present invention are water based and prepared by a wet process. Unlike the thermal evaporation and other vacuum based processes that produce dry silver nano-powders, the wet process produces silver nanoparticles but the nanoparticles stay in solution. Even in the spent compositions (those after use in the antimicrobial treatment of medical and non-medical devices) the silver nanoparticles are not a dust hazard like the dry powders. Dry powders are a potential health risk and at present their risk of exposure is not very well understood.

A composition of the present invention comprises silver nanoparticles with an average size ≥50 nm in diameter that are generally spherical and having relatively narrow particle size distribution. Although most particles are spherical other types of shapes can also form and be present in the compositions of the present invention.

Figure 1:
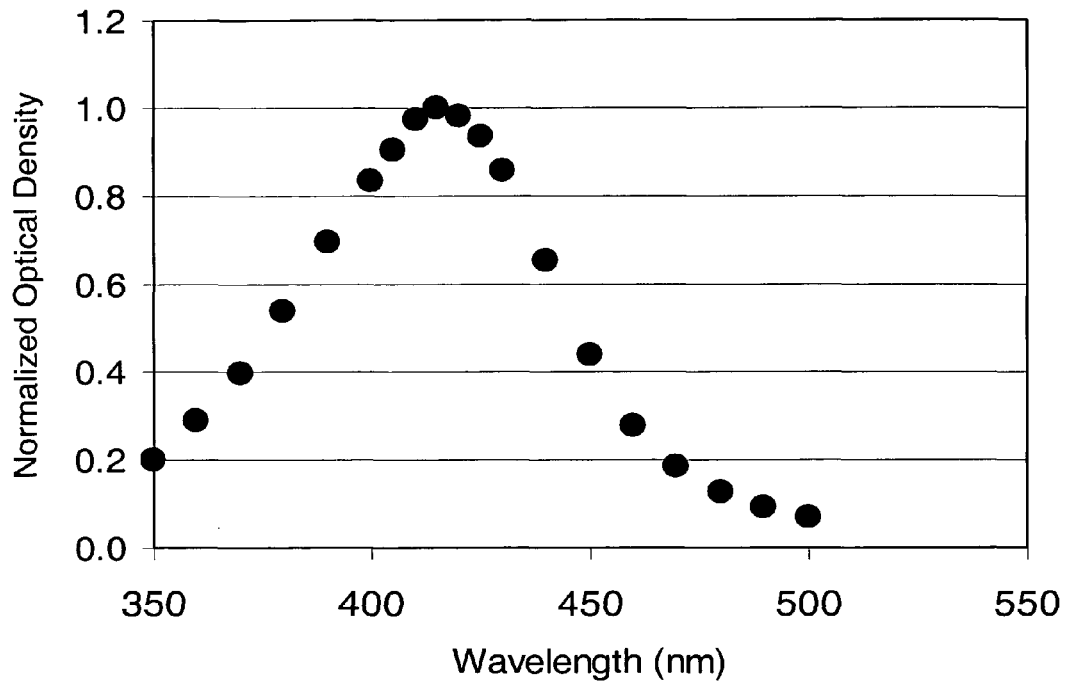
FIG. 1 shows a representative spectrogram obtained by UV-Visible spectroscopic analysis of an aqueous antimicrobial silver nanoparticle composition in accordance with the present invention.

Upon nanoparticle formation, the silver nanoparticles impart a characteristic yellow to yellow amber color depending on the concentration of nanoparticles present. When examined by UV-VIS spectroscopy the compositions yield a characteristic spectrum (FIG. 1) having a wavelength maximum around 420-425 nm. According to the physics of nanoparticles, the color is due to the plasmon resonance band associated with spherical silver nanoparticles having size of 5 to 10 nm. Even after increasing the starting concentration of silver, the peak value of 420-425 nm remains unchanged. This suggests that the average particle size obtained in the compositions is relatively independent of the starting concentration of the silver nanoparticles. With an increase in nanoparticle size the absorption peaks tend to red shift to a higher wavelength. The type of stabilizing agent used may also affect the wavelength maximum and the average particle size and the distribution. In the case of a composition stabilized by polyacrylamide, the wavelength maximum at 445 nm suggests that average nanoparticles size is somewhat larger than the composition stabilized by Polysorbate 20. The compositions of the present invention show only a single peak under UV-VIS spectroscopy.

Using the formula below, on a unit mass basis, one can calculate the available surface area of an example of silver nanoparticles of the present invention $$\text{Surface Area} = 6/[\text{density} \times \text{particle dia}]$$

The available surface area per unit gram for a 15 nm diameter particles is 3.81e5 per $cm^2$/gm. The surface area for other nanoparticles of the present invention can easily be determined.

Non-aqueous compositions are contemplated by the present invention. By non-aqueous it is meant that the solvent component of the composition is non-aqueous, as in organic solvents, those that are not miscible with water such as chlorinated alkanes, esters of carboxylic acids (ethyl acetate, butyl acetate), esters of ethylene glycol, propylene glycol, toluene, xylene, lower alkenes, and this list is not exhaustive, generally, non-polar in nature, though small amounts of water may be present. Even when solvents are immiscible with water they will have some finite solubility in water and similarly water will have a finite solubility in the organic solvent. Generally, dissolved water in an organic solvent will be less than 5% v/v. The non-aqueous solvents may be neat or may be binary or multi-component mixtures. For example, a solvent may be pure chloroform or it may be a mixture of chloroform and ethyl acetate (a binary mixture) or it can be a mixture of chloroform, ethyl acetate and toluene (ternary or multi-component mixture). Further, a solvent may be polar (aprotic or protic) or non-polar. They are useful in applications where aqueous silver compositions cannot be used. Non-aqueous compositions may be based on solvents that have a range of boiling points from room temperature to above 300° C. for some thermal transfer fluids.

Figure 2:
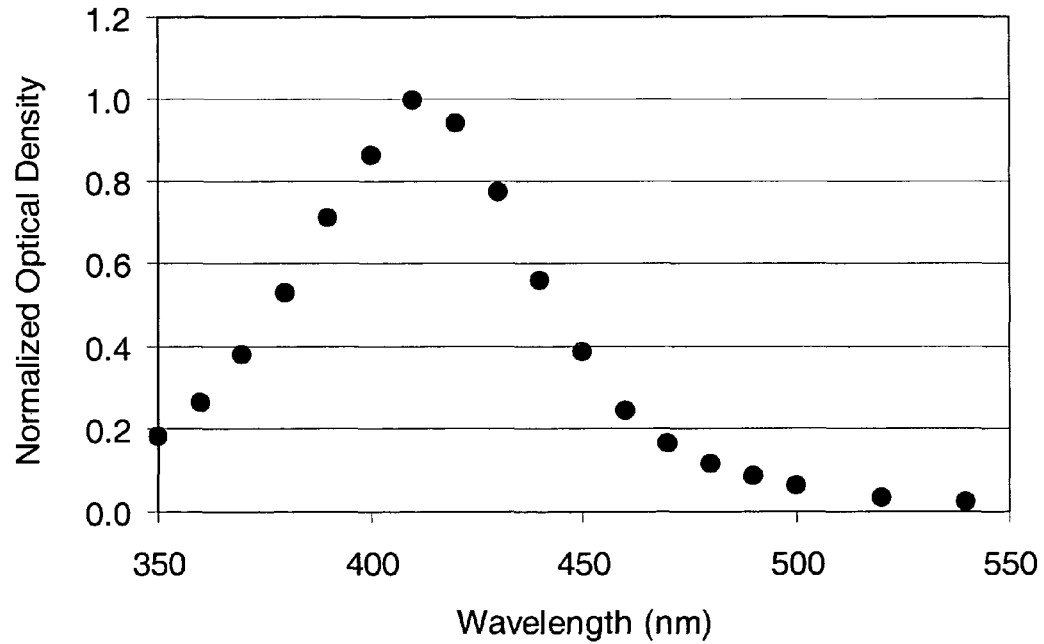
FIG. 2 shows a representative spectrogram obtained by UV-Visible spectroscopic analysis of a non-aqueous antimicrobial silver nanoparticle composition in accordance with the present invention, wherein the solvent comprises chloroform.

An example of a non-aqueous composition comprises chloroform as solvent. FIG. 2 shows the UV-VIS spectrum of such a composition with a maximum peak ~430-435 nm, a slight red shift in spectrum in comparison to an aqueous composition occurs. In all other respects, the spectrum is identical to that for an aqueous composition. The small red shift of the absorption peak (<5 nm) have previously been reported in published literature (Wang et. al., Langmuir, Vol. 14, pp 602 (1998)). However it is not attributed to an increase average size of silver nanoparticles but more likely a result of changes in polarity of the solvent that may shift the plasmon resonance band to the right. Further a spontaneous change in particle size is also not possible simply as a result of the extraction operation to draw silver nanoparticles from aqueous phase into the non-aqueous phase.

Figure 3:
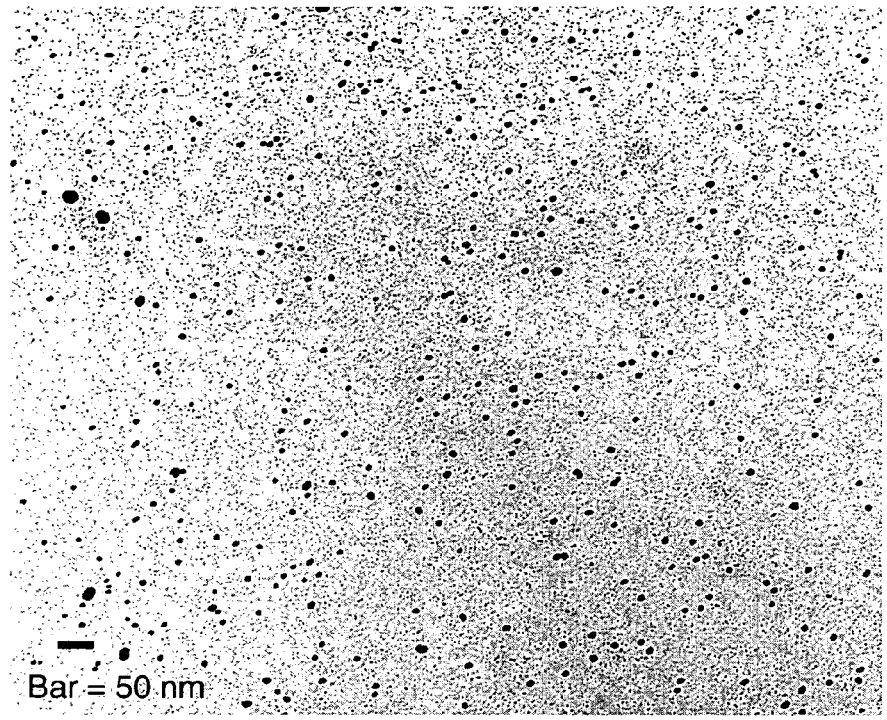
FIG. 3 shows a representative transmission electron micrograph of an aqueous antimicrobial silver nanoparticle composition in accordance with the present invention.
Figure 4:
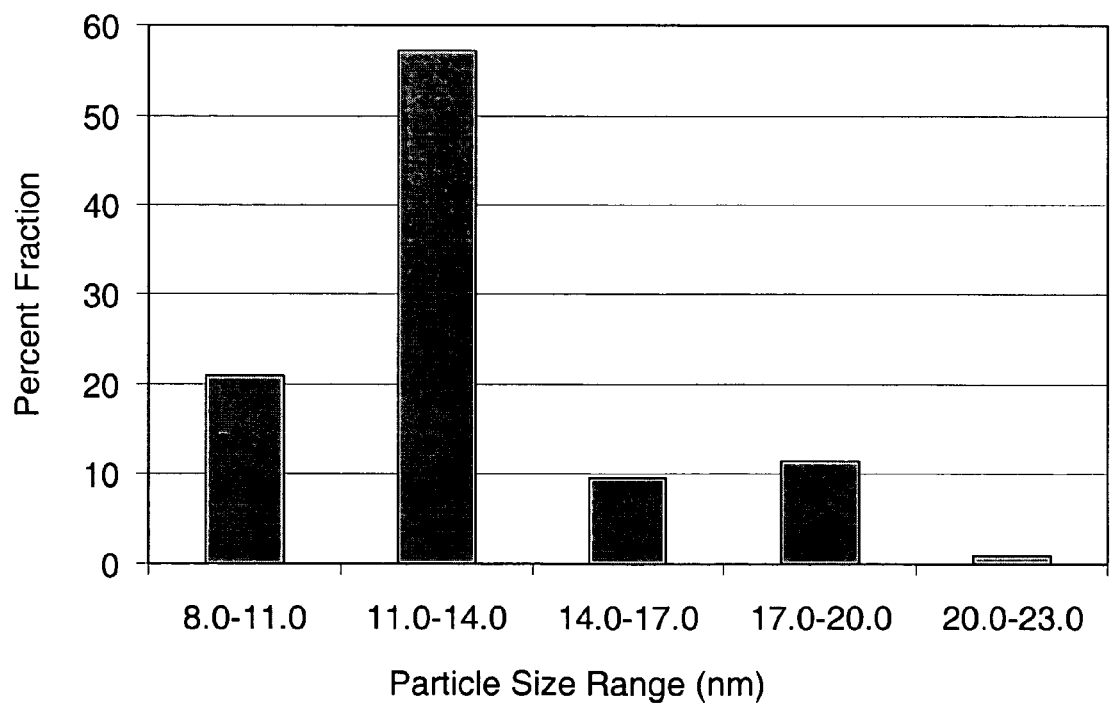
FIG. 4 shows the particle size distribution of an aqueous antimicrobial silver nanoparticle composition in accordance with the present invention.
Figure 5:
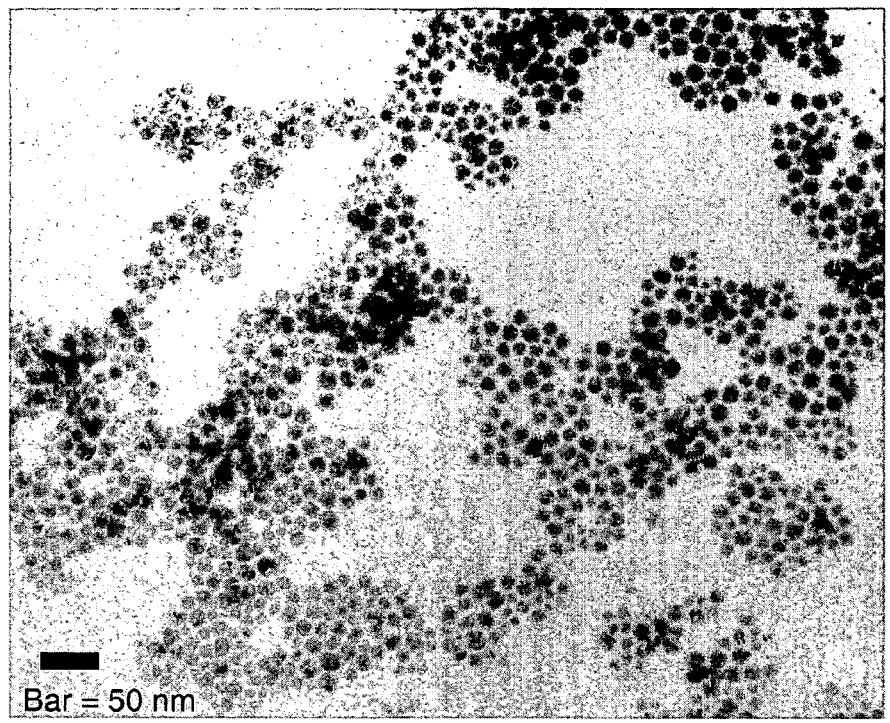
FIG. 5 shows a representative transmission electron micrograph of a non-aqueous antimicrobial silver nanoparticle composition in accordance with the present invention, wherein the solvent comprises chloroform.
Figure 6:
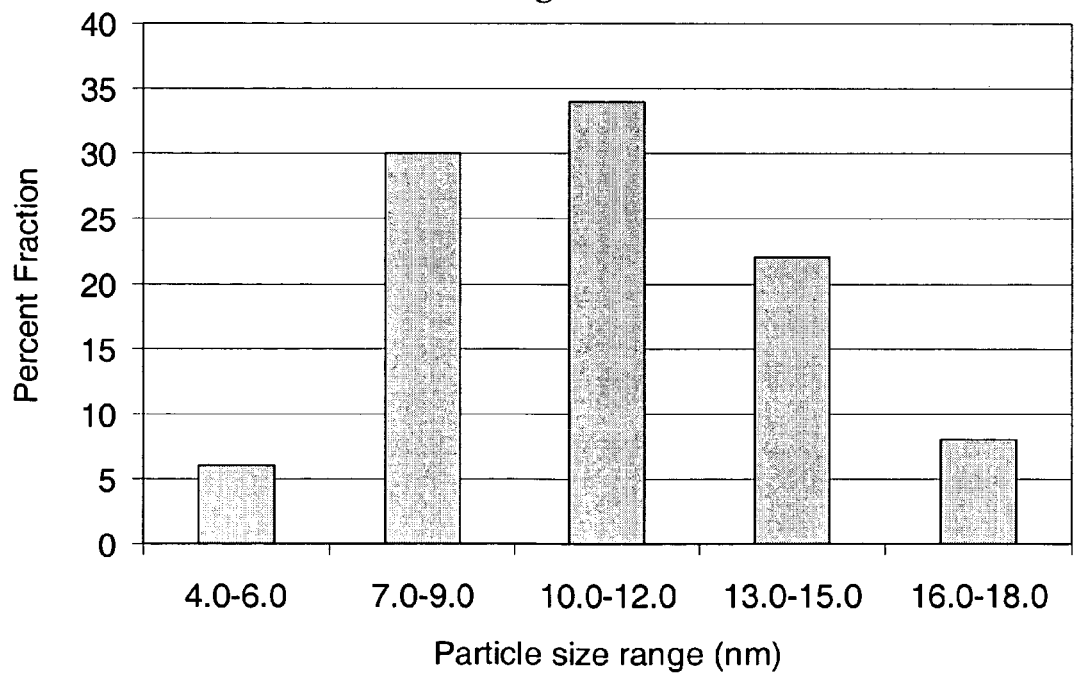
FIG. 6 shows the particle size distribution of a non-aqueous antimicrobial silver nanoparticles composition in accordance with the present invention, wherein the solvent comprises chloroform.

A TEM micrograph of silver nanoparticles is presented in FIG. 3. The majority of silver nanoparticles in the compositions of the present inventions are generally close to spherical though occasionally some flat faces may be present. The silver nanoparticles shown were prepared in aqueous medium utilizing Polysorbate 20, silver saccharinate and TEMED. By measuring the diameter of at least 100 particles in the TEM image, an estimate of size distribution of the silver nanoparticles was obtained. The corresponding particle size distribution of silver nanoparticles in aqueous medium is presented in FIG. 4 and shows an average size of ~15 nm. FIG. 5 shows TEM image of silver nanoparticles from a non-aqueous composition. The nanoparticles were first prepared in aqueous medium and then extracted into a non-aqueous solvent, chloroform. A few drops of chloroform solution comprising silver nanoparticles were dried on a standard copper grid. The majority of silver nanoparticles in the compositions of the present inventions are generally close to spherical. FIG. 6 shows the size distribution of silver nanoparticles in a non-aqueous medium with an average size approximately 11-12 nm with all particles smaller than 25 nm. The average size of silver nanoparticles in a non-aqueous composition is quite close to the average size in an aqueous medium. This fact is not surprising when it is noted that the silver nanoparticles in the non-aqueous medium were extracted from the aqueous solution.

Figure 7:
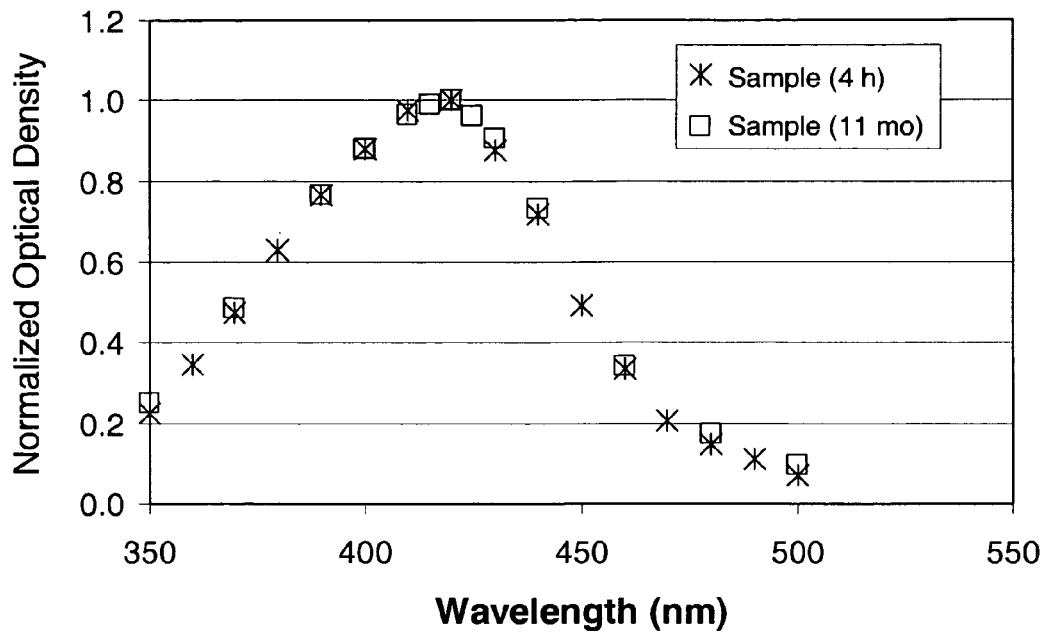
FIG. 7 shows representative spectrograms obtained by UV-Visible spectroscopic analysis of an aqueous antimicrobial silver nanoparticle composition in accordance with the present invention, wherein, as indicated in the figure, the aqueous antimicrobial silver nanoparticle composition was either prepared fresh (4 h) or analyzed at after storage at about 25° C. for about 11 months.

To be commercially feasible, the antimicrobial compositions of the present invention must exhibit reasonable shelf life. FIG. 7 compares the UV-VIS spectra of an aqueous composition made fresh and after aging the composition at ambient temperature (25° C.) for nearly a year. There is almost no difference between the two, suggesting no change in the particles size or particle size distribution. The data clearly demonstrate that the aqueous compositions of the present invention possess excellent shelf life Long term shelf life is not limited only to the aqueous compositions of the present invention but extend to non-aqueous compositions as well. The non-aqueous composition was tested in chloroform for over 3 months by UV-VIS spectroscopy and found no change in the spectrum shape or peak wavelength.

In addition to uses in rendering medical and non-medical articles antimicrobial, both the aqueous and non-aqueous silver nanoparticles compositions can be used to impart antimicrobial properties to fluid based compositions. Non-limiting examples of fluid compositions include adhesives, household sprays, disinfecting solutions or compositions such as those disclosed in U.S. Pat. No. 4,915,955 and incorporated by reference herein its entirety, coating compositions for indoor and outdoor wood products, and personal lubricants.

The compositions of the present invention may comprise a wide range of amounts of silver. Different amounts of silver in the compositions can be achieved simply by using the desired amounts of silver compounds during the production. For example, it would be logical to expect a larger amount of silver nanoparticle deposition when untreated articles are treated with compositions comprising a higher number of silver nanoparticles and vice versa. Alternately, an incremental amount of silver loading on a silver treated surface can be achieved by a secondary treatment using a silver composition having a lower amount of silver. Using composition having a particular silver amount, one can spray or dip an article multiple times to effect higher silver loading on the article. Each successive dip or spray would cause an incremental increase in silver loading until the desired level is achieved. The antimicrobial silver compositions of the present invention are generally non-viscous or have low viscosities and allow for uniform coating or contacting of surfaces, particular surfaces micron sized features and rendering them antimicrobial.

The silver nanoparticles of the present invention are formed from weakly water soluble silver compounds formed with a variety of anions both inorganic and organic. However, even highly water-soluble compounds may be used in the practice of the present invention. Silver compounds with imidic organic anions are useful, and though many examples are given with silver saccharinate, the invention comprises any silver compound that will form nanoparticles in the methods disclosed herein. Silver compounds having imidic organic anions are the subject of another co-pending patent, entitled Antimicrobial Devices and Compositions, filed Aug. 1, 2005, PCT/US2005/027260, incorporated by reference herein in its entirety, and all the compounds taught therein are included in the present invention. Silver compounds with derivatives of saccharin can be suitably employed. Other silver compounds, made by the reaction of soluble silver salts with compounds with active methylene groups e.g. acetylacetonate and derivatives may also be used.

In one embodiment of the invention, antimicrobial compounds comprise compounds of silver as represented by:

wherein, M is silver, n is 1 or more X is selected from A, B or C where $R_1$ and $R_2$ are -P or -WP; and W is a linker of branched alkyl chain of 1-27 carbon atoms, straight alkyl chain of 1-27 carbon atoms, monoethers containing 2-20 carbon atoms and polyethers containing 2-20 carbon atoms; and P is hydrogen, halogen atoms, haloalkyl, amide, sulfate, phosphate, quarternary ammonium, hydroxyl, hydroxymethyl, phosphonate, amino, carboxyl, carboxymethyl, carbonyl, acetyl, succinimidyl ester, isothiocyanate, isocyanate, iodoacetamide, maleimide, sulfonyl halide, phosphoramidite, alkylimidate, arylimidate, acide halide, substituted hydrazines, substituted hydroxylamines, carbodiimides, cyano, nitro, fluormethyl, nitrophenyl, sulfonamide, alkenyl or alkynyl; and $R_3$ and $R_4$ are hydrogen, straight alkyl with $C_1$-$C_8$ carbon atoms, optionally terminating in aryl or substituted aryl groups, branched alkyl with $C_1$-$C_8$ carbon atoms, phenyl, substituted phenyl, benzyl, substituted benzyl and fluoromethyl; and A is one of the following:

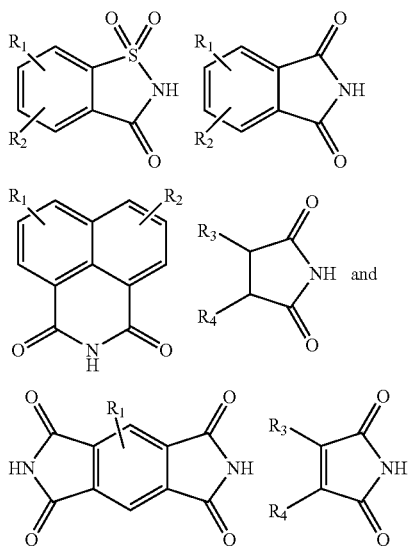

B is one of the following

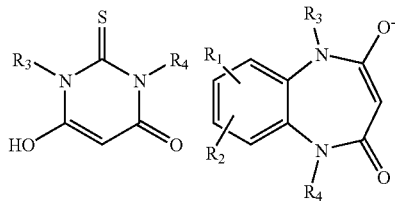

$R_1$ and $R_2$ are -P and -WP as described above, and

W is a linker as described above, and $R_3$ and $R_4$ are as described above.

C=behenate or bis(2-ethylhexyl) sulfosuccinate

Another embodiment of the invention comprises complexes of silver $$M^+[Y^-]_n$$

where M is silver, n is 1 or more; and Y is the following:

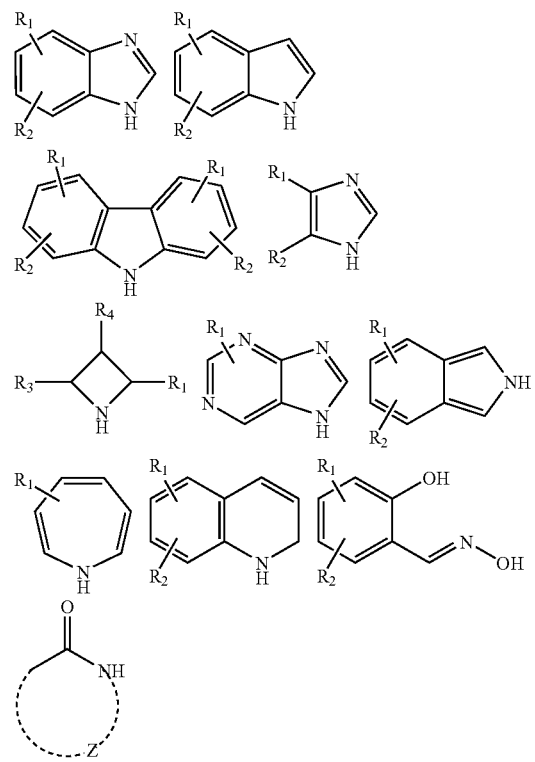

where $R_1$ and $R_2$ are selected from the group consisting of -P and -WP; as described above, and W is a linker as described above. $R_3$ and $R_4$ are described above and Z is C6 or C8 alkyl.

Another embodiment of the present invention comprises the following where $$M^+[Y'^-]n$$

where M is silver, N is 1 or more and Y'— is the following:

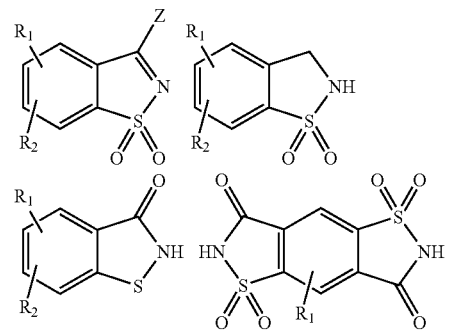

where $R_1$ and $R_2$ are selected from the group consisting of -P and -WP; as described above, and W is a linker as described above. $R_3$ and $R_4$ are described above and Z is amino, alkylamino, chloro, or HNX, wherein X in HNX comprises aryl, hydroxyl, amino, $NHC_6H_5$, or $NHCONH_2$. Other ligands that form silver compounds of the present invention comprise the following shown in Table 1:

TABLE 1

| ID | Name | Structure |
|---|---|---|
| 1.01 | 1,1-Dioxo-1,2-dihydro-1$\lambda^6$-benzo[α]isothiazol-3-one | 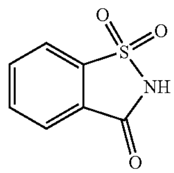 [SMILES: O=C1NS(=O)(=O)c2ccccc21] |
| 1.02 | Pyrrolo[3,4-f]isoindole-1,3,5,7-tetraone | 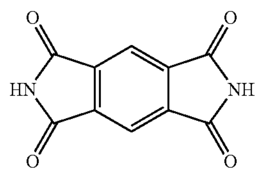 [SMILES: O=c1[nH]c(=O)c2cc3c(=O)[nH]c(=O)c3cc12] |
| 1.03 | Aziridine | 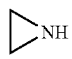 |
| 1.04 | Azetidine | 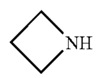 |
| 1.05 | Isoindole-1,3-dione | 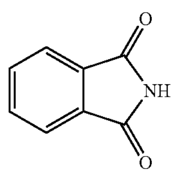 [SMILES: O=C1NC(=O)c2ccccc21] |
| 1.06 | Pyrimidine-2,4,6-trione | 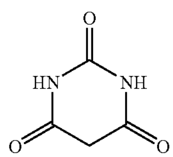 |
| 1.07 | 2-Thioxo-dihydro-pyrimidine-4,6-dione | 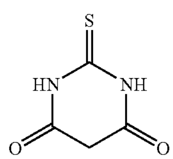 |
| 1.08 | Pyrrole-2,5-dione | 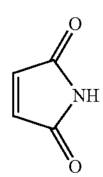 |
| 1.09 | Imidazole-2,4-dione | 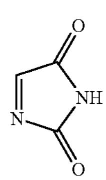 |
| 1.10 | Benzo[de]isoquinoline-1,3-dione | 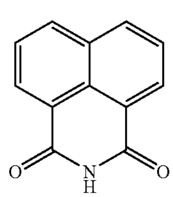 [SMILES: O=C1NC(=O)c2cccc3cccc1c23] |

The nanoparticles may be made from a single silver compound or mixtures of silver compounds. For example, a mixture might comprise silver compounds having high and low water solubilities. Further the binary mixture might comprise a range of 0 to 100% the weakly water-soluble silver compound. For example, when preparing silver nanoparticles, sodium saccharinate may be added to only 80% of the amount required to react with silver nitrate, then add TEMED and so on. Therefore in the mixture, there is silver nitrate (soluble salt) and silver saccharinate (weakly soluble salt) together. Similarly one can weigh out powder forms of silver nitrate and silver propionate in any desired proportions (0% silver nitrate to 100%).

The compositions of the present invention comprise a solvent, and the solvent may be water or a mixture of water and known miscible organic solvents, a stabilizing agent which may be a polymer and/or a surfactant, silver compound and a reducing agent. The solvent is water or a mixture. If the solvent is a mixture where the water content may range between 55% v/v and 95% v/v, the mixture may be any water miscible organic solvents including lower straight chain ($C_1$-$C_6$) or branched alcohols, acetone, tetrahydrofuran, formamide, dimethyl formamide, acetamide and other similar solvents. If the stabilizing agent used is a surfactant, surfactants including, but not limited to, polysorbates or Tweens, are useful. Any suitable surfactant may be used. The reducing agent, the agent that is thought to trigger the formation of silver nanoparticles in the solution includes, but is not limited to, tertiary, secondary and primary amines, tertiary, secondary and primary diamines, homopolymers or copolymers having primary amine, secondary amine and tertiary amine moieties. Amine compounds may be aliphatic or aromatic. Likewise, aliphatic and aromatic primary and substituted amides and polymeric amide analogs also can be used. An aromatic amide such as diethyl toluamide known as DEET also can be used. Other reducing agents are triethanolamine and N,N,N',N' tetramethyl ethylene diamine (TEMED). Polymeric compounds having TEMED moiety or other amines in the pendant chain or in the main chain may also be used as reducing agent.

The stabilizing agent may be a polymer, and a surfactant may or may not be used in addition to the polymer. The polymer may be a homopolymer or copolymer and can be synthetic or naturally derived. Non-limiting examples of polymers or copolymer suitable for use as stabilizers in the compositions include polymers formed from acrylamide and its derivatives, methacrylamide and its derivatives, polyamides, polyurethanes, polymers having no particular backbone but with urethane segments or tertiary amine groups in the side chains, other polymers predominantly polar in nature or co-polymers having a portion that is derived from polar co-monomers. Examples include, but are not limited to, acrylamide, methacrylamide, substituted acrylamides (i.e. —$CONH_2$ is replaced by $CON(R1)_2$, substituted methacrylamides, acrylic acid, methacrylic acid, hydroxyethyl methacrylate, acrylonitrile, 2-acrylamido-2-methylpropane sulfonic acid and its salts (sodium, potassium, ammonium), 2-vinyl pyrrolidone, 2-vinyl oxazoline, vinyl acetate, maleic anhydride and others. Though not wishing to be bound by any particular belief, it is believed that stability is achieved by steric hindrance due to the presence of polymer chains in such a way that the particle agglomeration and growth is suppressed.

The nanoparticle compositions of the present invention are fairly stable at low as well as high pH. The acids that can be added to antimicrobial silver compositions are organic acids including polymeric analogs such as polyacrylic acid, acetic acid, citric acid and similar acids though adding nitric acid >10% will destroy the compositions by dissolving the silver nanoparticles. Nitric acid at concentration below 10% will also destroy the compositions over time. Adding 10% v/v ammonia solution does not affect the silver nanoparticle compositions (i.e. no color change is seen).

Silver content, as nanoparticles, of the compositions can be adjusted by initially selecting the starting amount of the silver compound in making the nanoparticles or by diluting the composition after making the nanoparticles. The optical density of the silver nanoparticles compositions obtained using low concentrations of silver salt may not even reach 2.0. However, the optical density of compositions made with concentrated silver salt solutions may be extremely high requiring very high dilution (>100 fold) for absorbance readings below 2. Just as nitric acid can destroy the silver nanoparticles compositions by dissolving, adding certain water miscible solvents causes nanoparticles to agglomerate and precipitate out. The silver content can be increased by concentrating the compositions by removal of solvent by means known to those ordinarily skilled in the art. In fact one can remove most of the solvent from the compositions, re-dilute to regenerate the composition to the original state without causing significant silver nanoparticle agglomeration.

The compositions of the present invention comprise silver nanoparticles and may also comprise weakly soluble silver compounds. In the course of the preparation of nanoparticles, a silver salt may formed in situ which may not be converted to silver nanoparticles during the reaction period. Silver compositions where the silver may or may not be present as unreacted trace of a salt are still encompassed by the present invention.

Another embodiment of the antimicrobial silver compositions of the present invention is a non-aqueous antimicrobial silver composition. Those skilled in the art have recognized that it is difficult to produce stable silver nanoparticles in a non-aqueous medium (Zeiri and Efrima, J. Phys. Chem., Vol. 96, pp 5908-5917 (1992)). The non-aqueous silver nanoparticles compositions of the present invention may be prepared by extracting the nanoparticles from the aqueous compositions into a non-aqueous phase. While non-aqueous solutions containing silver have been made, the studies have not shown their antimicrobial efficacy. By non-aqueous we mean organic media that are generally immiscible with water over a large ratio between water and immiscible solvent. Preferred non-aqueous solvents used in preparing the compositions of the present invention are methylene chloride, chloroform and other aliphatic and aromatic chlorinated solvents, cyclohexane, diethyl ether, ethyl acetate and mixtures thereof. The amount of silver content in non-aqueous compositions can be adjusted by choosing the proper amount of silver in the preparation of the aqueous composition followed by extraction of the aqueous composition and by further appropriate dilution if needed.

One broad embodiment of the present invention is compositions comprising the mixtures of a surfactant, a silver compound preferably a salt (that can ionize to a silver cation and an anion in solution), TEMED and water. These compositions are precursor compositions to the antimicrobial silver compositions of the present invention. Precursor compositions are then subjected to certain treatments to transform them into antimicrobial compositions of the present invention. For example, the precursor compositions can be heated to initiate the silver nanoparticles formation which is indicated by a yellow color. Heating can be achieved by direct or indirect contact with electric heating element, by IR lamps, by microwave energy, by acoustic energy or by the use of other electromagnetic radiation. Precursor compositions also may be converted to antimicrobial silver nanoparticle compositions by exposure to intense light energy (UV lamps, strobes, mercury vapor lamps, halogen lamps, laser beams etc). Pre-cursor compositions may be employed to form silver nanoparticle compositions where the nanoparticles may take different shape and form. They may also be used in electroless plating applications in the preparation of silver coated reflective coatings on glass beads, plastic surfaces for improving the light reflectance of signs at night, and other uses. Precursor compositions which are aqueous in nature may be made and stored below ambient temperature and used subsequently without any loss of performance.

Methods of Preparation of Antimicrobial Silver Compositions

Different methods can be employed to prepare of the antimicrobial silver compositions of the present invention. A method comprising the following
(i) preparing the aqueous solutions of a surfactant (and/or polymer), of sodium saccharinate (or a suitable anion) and of soluble silver salt solution,
(ii) adding the sodium salt solution to the surfactant solution under stirring,
(iii) further adding soluble silver salt solution to cause the precipitation of weakly soluble silver salt,
(iv) adding the tertiary diamine (TEMED) and,
(v) causing a temperature increase of the resulting solution and maintaining the increase for specific time period.

In another embodiment, after the temperature increase for a specific duration in step (v), the solution temperature is returned to room temperature. If desired, the solution temperature may also be lowered to a temperature other than room temperature. The temperature can be above or below the room temperature. In the above embodiments, the weakly soluble silver salt may not immediately form a clear precipitate, but this should not be considered as limiting the practice of the invention. A variation of the above method involves reversing the order of addition of sodium salt solution and soluble silver salt solution. A further variation involves substituting the surfactant with a water soluble polymer solution in step (i) with the other steps remaining the same.

In one embodiment using polyacrylamide as the stabilizer in one composition of the present invention, the preparation is as follows.
(a) preparing the polymer solution of desired concentration,
(b) adding in succession under mixing appropriate quantities of the alkali metal solution of appropriate anion such as saccharinate, soluble silver salt solution and the reducing agent and,
(c) causing a temperature increase and maintaining the temperature increase for a specified time period.

Optionally the solution may not be heated but left at room temperature under ambient light over a period of 24 hours to 7 days to complete the formation of silver nanoparticles. The temperature increase can be caused by methods known to those ordinarily skilled in the art. Alternately, light energy sources may be employed to form silver nanoparticles.

In preparing non-aqueous silver compositions of the present invention, a method comprises
- (a) preparing the aqueous silver nanoparticles composition with desired silver content,
- (b) reducing its volume to concentrate the aqueous composition,
- (c) extracting the said concentrate with non-aqueous solvent or solvent mixture and,
- (d) recovering the non-aqueous solvent or solvent mixture comprising the extracted silver nanoparticles.

The step (b) above is optional especially if the silver content of the aqueous composition is significantly high. Likewise the step (c) optionally may be carried out multiple times, each time using a fresh portion of the non-aqueous medium. The temperature may be room temperature in the practice of this method of the present invention.

In the preparation of non-aqueous silver compositions of the present invention, one can optionally add to the non-aqueous solvent a compound that may be a liquid or a solid having at least one double bond in its molecular structure. For example one may add such a compound as an extraction aid in amounts up to 25% of the non-aqueous solvent to improve the extraction efficiency.

In an embodiment for making non-aqueous silver compositions, the double bond containing compound may also serve as a stabilizing agent in the preparation of the aqueous silver compositions. An oleate may be added instead of the surfactant. In the second case, one may form silver sorbate (in the presence of surfactant) and then convert the salt to nanoparticles using TEMED. The sorbate anion has two double bonds and the rationale is this organic anion may get readily transferred into the non-aqueous phase. Such a compound for example may be an oleate, sorbate, fumarate or cinnamate. The compounds listed by no means should be construed as limiting. The resulting aqueous silver compositions extract more readily with non-aqueous solvent transferring silver nanoparticles to the non-aqueous medium with greater efficiency and help to maintain the stability in non-aqueous environment.

A modification of the method of preparation of non-aqueous silver composition is to extract silver nanoparticles from aqueous silver compositions into a non-aqueous solution and then add a double bond compound to increase the stability of the compositions. One may add no more than 25% by weight of the non-aqueous solvent of this compound. Non-limiting examples of double bond compounds are oleic acid, sorbic acid, cinnamic acid and their derivatives. Polymeric compounds such as polyacetylenes, polyvinylenes and their derivatives can also be used that have some solubility in extracting the non-aqueous media.

Other compounds may be added to the compositions. For example, in some applications of non-aqueous compositions, long alkyl chain bearing thiols may be added to aid in the formation of metal nanoparticles layers on silicon and similar semi-conducting surfaces.

Effect of Process Conditions

Various parameters may affect the properties and performance of the compositions, such as silver compounds with different anions, the concentration effects of the silver salts, the stabilizing agent and the reducing agent. A robust process for producing silver nanoparticles can be used for nanoparticle deposition on various substrates.

Silver Salts with Different Anions

The antimicrobial silver compositions of the present invention are quite convenient to prepare. They were conveniently prepared starting from a variety of silver salts formed in-situ from corresponding sodium salts. Though one can also directly use silver salts in dry form if available without departing from the scope of the invention. The salts used may comprise organic or inorganic anions. The salts were then reduced to silver nanoparticles in the presence of a surfactant, Polysorbate 20, and TEMED by heating the resulting mixture in a microwave for a brief period. Stock solutions of Polysorbate 20 (~76 gm/L), silver nitrate (0.1M) and sodium salts (0.125M) were prepared and were used in a volume ratio of 1.2/4.0/3.0/1.2 for Tween® 20, sodium salt solution, silver nitrate solution and TEMED. UV/VIS spectra of silver nanoparticles compositions were measured on a Beckmann DU-20 spectrophotometer by diluting the composition with water (25 µl in 3 mL water) in a 1 cm path length cuvette. Deionized water was used as a reference.

Figure 8:
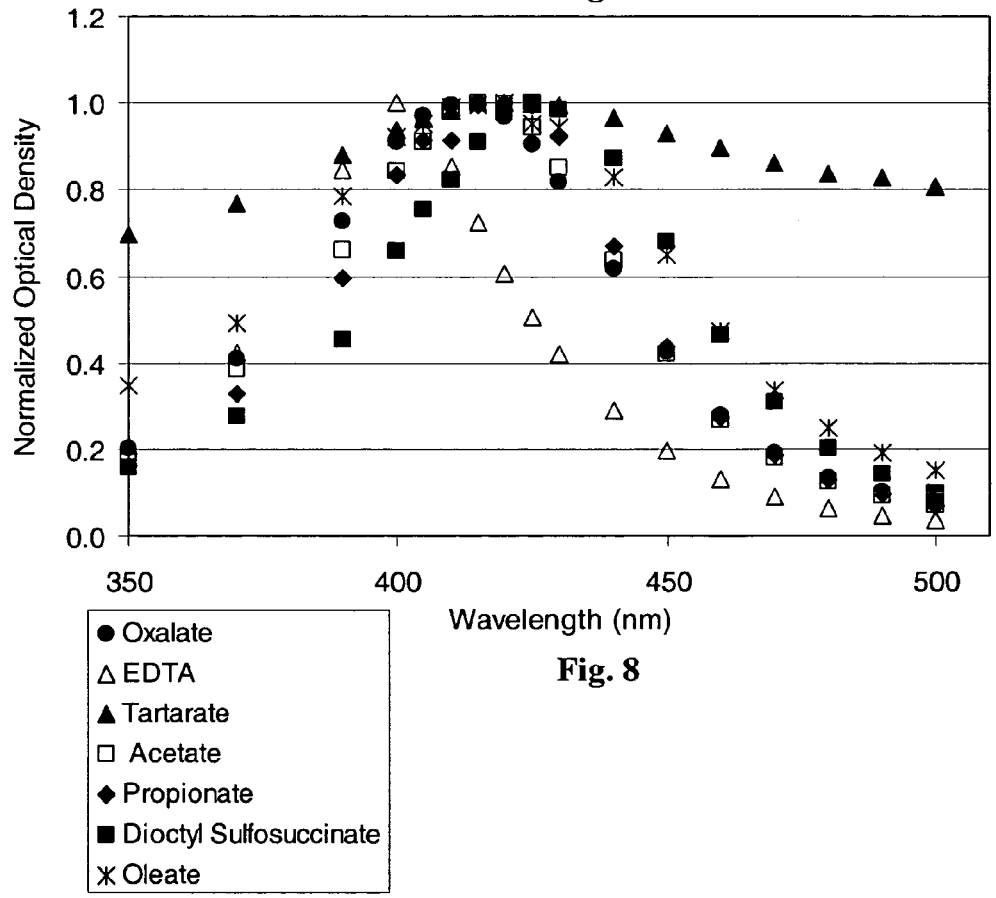
FIG. 8 shows representative spectrograms obtained by UV-Visible spectroscopic analysis of various aqueous antimicrobial silver nanoparticle compositions in accordance with the present invention which were prepared from various sodium salts.
Figure 9:
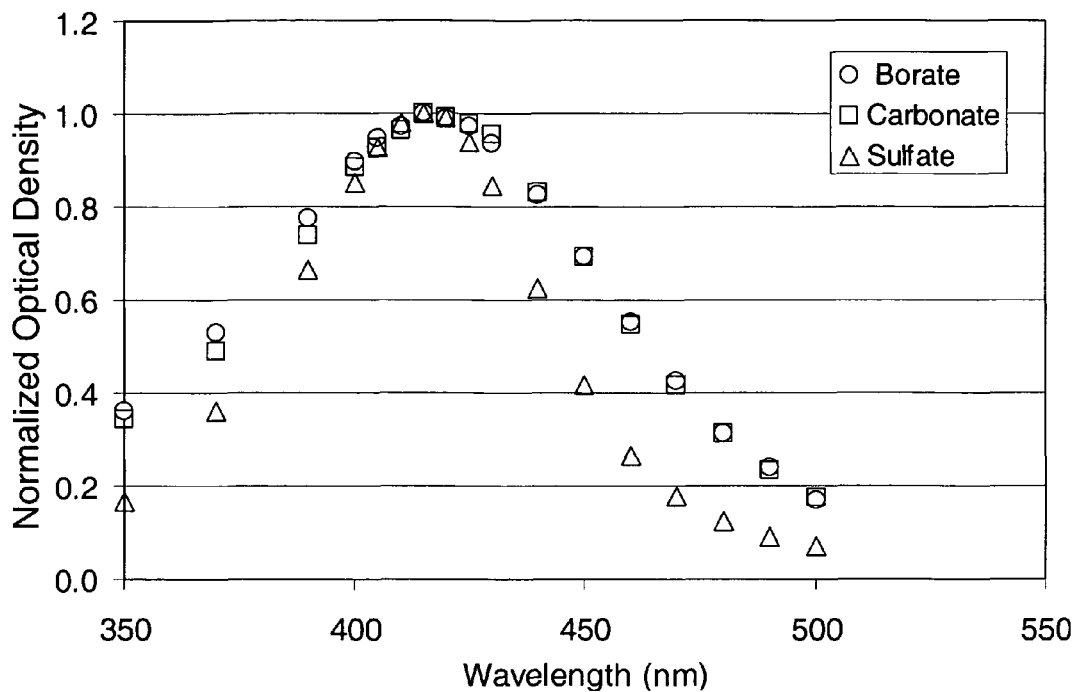
FIG. 9 shows representative spectrograms obtained by UV-Visible spectroscopic analysis of various aqueous antimicrobial silver nanoparticle compositions in accordance with the present invention which were prepared from various sodium salts, wherein the various aqueous antimicrobial silver nanoparticle compositions comprise the anion indicated.

Table 1 lists the sodium salts that were used in preparing corresponding silver salts in-situ. Of the 15 salts tested, only about half of them failed to form clear and stable yellow brown silver nanoparticles solution (FIG. 8). Silver chloride (from sodium chloride) gave a red or flesh color precipitate that immediately settled at the tube bottom. In addition, silver salts with the following anions did not yield stable nanoparticles solutions: borate, tartarate, carbonate, citrate, phosphate and lauryl sulfate though their spectra indicated a peak ~420 nm suggesting the formation of silver nanoparticles in size ~10 nm (FIG. 9). Of the silver salt yielding solutions of poor stability, half were organic anions and the other half were inorganic suggesting the inability to form stable nanoparticles solutions was not related to their organic or inorganic nature. While the use of the silver salts of anions borate, tartarate, carbonate, citrate, phosphate and lauryl sulfate may not be optimal, their use in the preparation of antimicrobial compositions is encompassed by the present invention.

TABLE 1

Sodium salts with various inorganic & organic anions used in preparing silver nanoparticles compositions

| Sodium salt type | Salt anion type | Precipitate or debris formed? | NP Solution Appearance |
| --- | --- | --- | --- |
| Chloride | Inorganic | Yes | Red, flesh color suspension, agglomeration |
| Borate | Inorganic | Yes | Dark green/grey suspension, agglomeration |
| Carbonate | Inorganic | Yes | Green/grey suspension, agglomeration |
| Sulfate | Inorganic | no, silver deposit on tube | Brown/yellow clear |
| Phosphate | Inorganic | yes | Grey clear, agglomeration |
| Acesulfame | Organic | no | Brown/yellow clear |
| Oxalate | Organic | no, silver deposit on tube | Brown/yellow clear |
| EDTA Di - salt | Organic | no | Brown clear |
| Tartarate | Organic | yes, some silver deposit | Green/grey suspension, agglomeration |
| Acetate | Organic | no, silver deposit on tube | Brown/yellow clear |
| Citrate | Organic | yes | Light green/beige suspension, agglomeration |
| Propionate | Organic | no, silver deposit on tube | Brown clear |

TABLE 1-continued

Sodium salts with various inorganic & organic anions used in preparing silver nanoparticles compositions

| Sodium salt type | Salt anion type | Precipitate or debris formed? | NP Solution Appearance |
|---|---|---|---|
| Dioctyl sulfosuccinate | Organic | no, no silver deposit on tube | Brown clear |
| Lauryl Sulfate | Organic | yes | Grey/green suspension, agglomeration |
| Oleate | Organic | no, no silver deposit on tube | Brown clear |

Note:
The precipitate or debris are filtered off or centrifuged to prevent interference during UV/VIS spectral measurements Another important observation was the in situ formed salts that readily formed silver nanoparticles did not show any precipitate or debris formation. The embodiment that yielded no precipitate or debris comprises a method comprising the following steps of, (i) preparing the aqueous solutions of the surfactant, sodium saccharinate (or a suitable anion) and silver salt solution, (ii) adding the sodium salt solution and the tertiary diamine (TEMED) to the surfactant solution under stirring, (iii) further adding soluble silver salt solution and, (iv) causing a temperature increase of the resulting solution briefly and then returning the temperature to room temperature.

Therefore, the method of adding silver nitrate as the last ingredient in solution to previous ingredients is one preferred embodiment of the present invention. Preferred volume ratios of starting reagents of 1.2/4.0/3.0/1.2 for Tween® 20, sodium salt solution, silver nitrate solution and TEMED respectively are important elements of one preferred embodiment for making nanoparticles compositions.

Visually, the nanoparticle solutions prepared using sodium oleate was the best. There was no debris or any metallic silver deposits on the tube wall. This was somewhat expected because published work have reported on the beneficial effect of oleate on silver nanoparticles (Wang et. al., Langmuir, Vol. 14, pp 602 (1998)). The oleate stabilized nanoparticles solutions tend to be very stable. Stabilizing effect of oleate has been attributed to silver's interaction with pi electrons of the oleate double bond.

FIGS. 8 and 9 show plots of absorbance (normalized to OD=1) versus wavelength for various organic and inorganic anions. The $\lambda_{max}$ for inorganic anions is 415 nm (FIG. 8 and Table 2) and their full width half maximum (FWHM) are of similar magnitude though the sulfate anion shows a tighter spectrum. Interestingly, the borate and carbonate anions project a spectrum that is similar to sulfate yet the nanoparticles solutions are not very stable. This indicates that under the conditions, the nanoparticles of small size ~10 nm and narrow distribution are formed with these two anions, but the ionic environment in those solutions is unable to prevent their agglomeration.

In comparison, silver nanoparticle solutions prepared from various organic anions more or less exhibit greater stability and the characteristic yellow brown color indicating wholesome presence of nanoparticles. Only a small difference in the spectral maximum among them is observed but with a wide variation in their spectra (FIG. 9). For example, the solution with EDTA anion shows a peak OD at 390 nm and relatively sharp spectra. On the other hand, a tartarate based solution while having a peak at 415 nm reveals a practically flat spectra. Such spectra indicate a very broad silver particle distribution.

In Table 2 we have listed wavelengths where peak OD was observed and FWHM values derived from the spectral data of solutions shown in the figures. Like inorganic anions we see $\lambda_{max}$ around 415-425 nm for organic anions. The fact that we observed the same $\lambda_{max}$ over so many different anions suggests the mechanism of silver nanoparticle formation have little to do with the type of anions present. But, the agglomeration behavior suggests that the stability of silver nanoparticles formed very much depend on the anion type. Without being bound to any theory, the inventors are hypothesizing that the interaction of anions with silver nanoparticles if thermodynamically favorable yield stable solutions.

In the same table, the FWHM is listed for each spectrum. The number is a measure of the width of the spectrum. Smaller the FWHM number indicates sharpness of the spectrum. The FWHM value of 53 nm for EDTA anion is the smallest seen so far and that includes

TABLE 2

$\lambda_{max}$ & FWHM values of UV-VIS spectra of silver nanoparticles compositions prepared by using different anions

| Salt anion | Anion type | $\lambda_{max}$ (nm) | FWHM (nm) (full width half max) |
|---|---|---|---|
| Chloride | Inorganic | ND+ | ND |
| Borate | Inorganic | 415 | 90 |
| Carbonate | Inorganic | 415 | 92 |
| Sulfate | Inorganic | 415 | 65 |
| Phosphate | Inorganic | ND | ND |
| Acesulfame | Organic | 415 | 92 |
| Oxalate | Organic | 415 | 70 |
| EDTA Di - salt | Organic | 400 | 53 |
| Tartarate | Organic | 415 | ND |
| Acetate | Organic | 415 | 67 |
| Citrate | Organic | ND | ND |
| Propionate | Organic | 420 | 72 |
| Dioctyl sulfosuccinate | Organic | 425 | 66 |
| Lauryl Sulfate | Organic | ND | ND |
| Oleate | Organic | 420 | 91 |

+=Not determined published literature that we have examined. The oleate FWHM value of 91 nm is fairly close to the value of 88 nm reported in a published paper that extensively examined oleate containing silver nanoparticle solutions prepared from silver nitrate. But one thing that distinguishes the present work is that our FWHM values are for solutions made from silver salts with concentrations 10 to 100 times higher than those previously tested. The fact that we observed similar FWHM means practically no agglomeration of nanoparticles in our solutions occur even when using such high silver concentrations. To some degree it points to the uniqueness of the surfactant and reducing agent combination that was employed.

Process Parameters

The effects of varying the stabilizer amount, reactants ratio, concentration of the reducing agent and the order of reagent addition on quality of the nanoparticle solutions were examined.

Appropriate stock solutions of sodium saccharinate, silver nitrate and Tween® 20 or Polysorbate 20 were prepared in de-ionized water. Reducing agent was used as received. We employed two methods to prepare silver nanoparticles. In Method A, a silver saccharinate suspension was first formed in the presence of surfactant by reacting silver nitrate and sodium saccharinate. To the suspension, TEMED was added and the resulting turbid mixture heated briefly in microwave oven to complete the nanoparticle formation. The Method B consisted of mixing surfactant Tween 20, sodium saccharinate and TEMED in a capped vial to form a clear solution. Silver nitrate solution was added last and the vial contents heated in microwave oven to produce nanoparticles. In all experiments, microwave heating time was 10 seconds on medium setting (Oven Make: Quasar Instant Matic Cooking, 1500 W).

Nanoparticle solutions were characterized by recording UV-VIS spectrum typically over 400 to 500 nm range on Beckman DU-20 Spectrophotometer. For the spectral scan, the nanoparticle solution was diluted with water (25 μl in 3 mL water) and transferred to a 1 cm path length plastic cuvette. De-ionized water was used as reference. The recording of the UV/VIS spectrum is a quick, convenient and easy way to establish the formation of silver nanoparticles. It takes advantage of strong absorption by silver nanoparticles (<50 nm in size) in the visible range (390 to 500 nm). Strong absorption is the result of plasmon resonance band of nanometer size silver particles. Such spectral evidence though is only indirect evidence of silver nanoparticles.

In the first part of our study, we employed Method A to investigate the effects of Tween 20 concentration, the molar ratio of silver nitrate to sodium saccharinate, silver nitrate concentration and TEMED concentration on nanoparticle formation. Tables 3 to 6 show the experimental details. The surfactant, sodium saccharinate, silver nitrate solution and TEMED volumes were in 10:10:10:1 ratio unless stated otherwise.

TABLE 3

Variation of Tween 20 Surfactant Concentration

| Exp No. | Tween 20 (g/L) | NaSac+ soln (M) | Silver nitrate soln (M) | TEMED (ml) | Precipitate or debris formed? | Solution appearance |
|---|---|---|---|---|---|---|
| 1 | 16.5 | 0.125 | 0.1 | 0.3 | Yes | Dark brown, no Ag deposit |
| 2 | 11.0 | 0.125 | 0.1 | 0.3 | Yes | Dark brown, no Ag deposit |
| 3 | 5.5 | 0.125 | 0.1 | 0.3 | Yes | Dark brown, no silver deposit |
| 4 | 0 | 0.125 | 0.1 | 0.3 | Yes | Ash green |
| 5 | 0 | 0.0625 | 0.05 | 0.3 | Yes | Ash green |
| 6 | 0 | 0.03125 | 0.025 | 0.3 | Yes | Ash green |

+ = Sodium saccharinate

TABLE 4

Variation of Sodium Saccharinate Concentration

| Exp No. | Tween 20 (g/L) | NaSac soln (M) | Silver nitrate soln (M) | TEMED (ml) | Precipitate or debris formed? | Solution appearance |
|---|---|---|---|---|---|---|
| 1 | 16.5 | 0.125 | 0.1 | 0.3 | Yes | Dark brown, no Ag deposit |
| 2 | 16.5 | 0.110 | 0.1 | 0.3 | Yes | Dark brown |
| 3 | 16.5 | 0.105 | 0.1 | 0.3 | Yes | Dark brown |
| 4 | 16.5 | 0.102 | 0.1 | 0.3 | Yes | Dark brown |
| 5 | 16.5 | 0.100 | 0.1 | 0.3 | Yes | Dark brown |
| 6 | 16.5 | 0.075 | 0.1 | 0.3 | Yes | Dark brown |
| 7 | 16.5 | 0.050 | 0.1 | 0.3 | Yes | Dark brown |
| 8 | 16.5 | 0.025 | 0.1 | 0.3 | Yes | Dark brown |

TABLE 5

Variation of Silver Nitrate Concentration

| Exp No. | Tween 20 concn (g/L) | NaSac soln (M) | Silver nitrate soln (M) | TEMED (ml) | Precipitate or debris formed? | Solution appearance |
|---|---|---|---|---|---|---|
| 1 | 16.5 | 0.1250 | 0.1 | 0.3 | Yes | Dark brown, no Ag deposit |
| 2 | 16.5 | 0.0625 | 0.05 | 0.3 | Little debris | Brown/yellow, Ag deposit |
| 3 | 16.5 | 0.03125 | 0.025 | 0.3 | No | Brown/yellow |

TABLE 6

Variation of TEMED Amount*

| Exp No. | Tween 20 concn (g/L) | NaSac soln (M) | Silver nitrate soln (M) | TEMED (ml) | Precipitate or debris formed? | Solution appearance |
| --- | --- | --- | --- | --- | --- | --- |
| 1 | 16.5 | 0.125 | 0.1 | 0.6 | Yes | Dark brown (purple tint) |
| 2 | 16.5 | 0.125 | 0.1 | 0.9 | Yes | Dark brown (purple tint) |
| 3 | 16.5 | 0.125 | 0.1 | 1.2 | Little debris | Dark brown (purple tint) |

*= The volume ratio was increased in favor of TEMED without changing volumes of other reactants Effect of Tween 20 Concentration When the Tween 20 concentration was varied between ~5.5 gm/L and 16.5 gm/L we observed little variation in the color and consistency of the nanoparticle solutions. All showed characteristic yellow brown color. The white precipitate observed in the solutions was the undissolved silver saccharinate. No debris due to nanoparticle agglomerates, which normally would be black, was seen.

Figure 10:
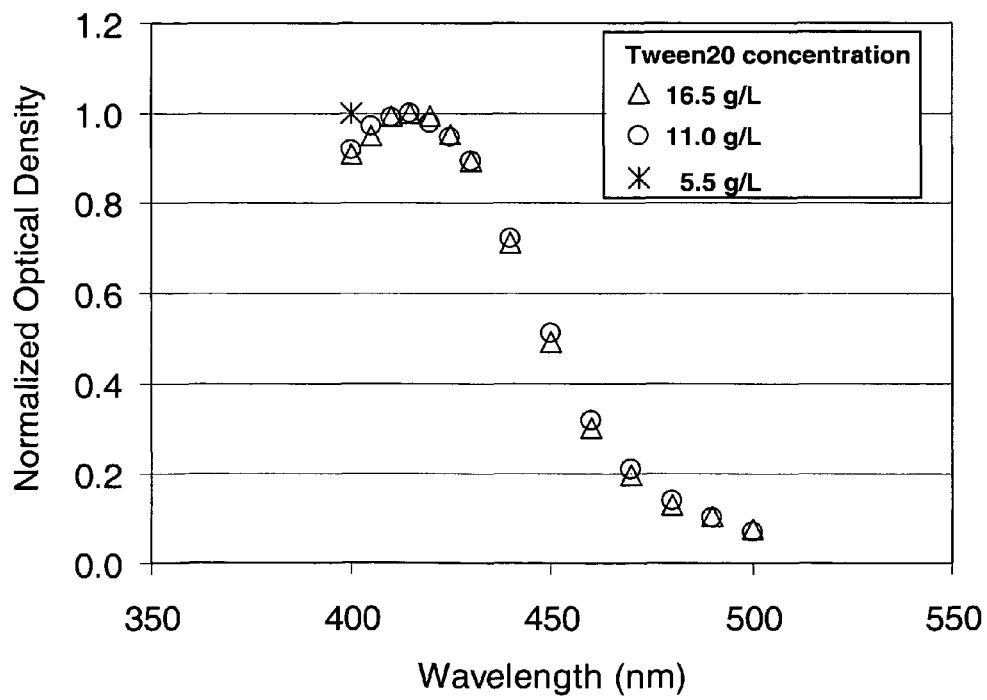
FIG. 10 shows representative spectrograms obtained by UV-Visible spectroscopic analysis of various aqueous antimicrobial silver nanoparticle compositions in accordance with the present invention which were prepared from various sodium salts, wherein the various aqueous antimicrobial silver nanoparticle compositions comprise Tween 20 (CAS No. 9005-64-5; $C_{58}H_{114}O_{26}$; known alternatively as polyoxyethylene (20) sorbitan monolaurate) at the indicated concentrations (g/L).

FIG. 10 shows the normalized UV-VIS spectra of nanoparticle solutions with different amounts of Tween 20. The spectra of solutions without Tween 20 was not measured. All spectra are almost identical indicating that all three nanoparticle solutions are practically the same. The spectral wavelength maximum falls around 415 nm. A full width at half maximum (FWHM) ~90 value can be inferred (by extrapolating the curve between 350-400 nm maintaining symmetry) and is consistent with published literature. It is worthy of note that no agglomeration of nanoparticles was observed despite employing silver salt concentrations that were 10 to 100 times higher than used in published reports. This was remarkable and yet somewhat unexpected because previous researchers have reported their inability to obtain stable nanoparticle solutions for silver concentration above 0.01M even after employing surfactants.

It is clear that stabilized silver nanoparticle solutions with a 0.1M silver concentration are achieved even with a low Tween 20 concentration of ~0.2% w/v. The data underscore the robustness of the preparation method. However, without Tween 20 in the solution, the nanoparticles agglomerated to form ash green colored precipitate. This was true regardless of the starting silver concentration. All solutions without Tween 20 failed to develop characteristic yellow brown coloration.

The Tween 20 concentration was also varied on the higher side i.e. 33 gm/L, 49.5 gm/L and 66 gm/L with matching increase in TEMED concentration. While we continued to see nanoparticle formation from the solution color and the observation of some debris that precipitated from the reaction mixture, the spectral signature of the solutions with higher Tween 20 remained essentially similar (data not shown) again verifying the process robustness. The data suggested that there was no advantage from the process point of view in raising surfactant content beyond the nominal value of 16.5 gm/L. However, higher concentrations of surfactant Tween 20 or other stabilizing agents can still b used without departing from the scope of the invention.

Effect of Sodium Saccharinate Concentration

Figure 11:
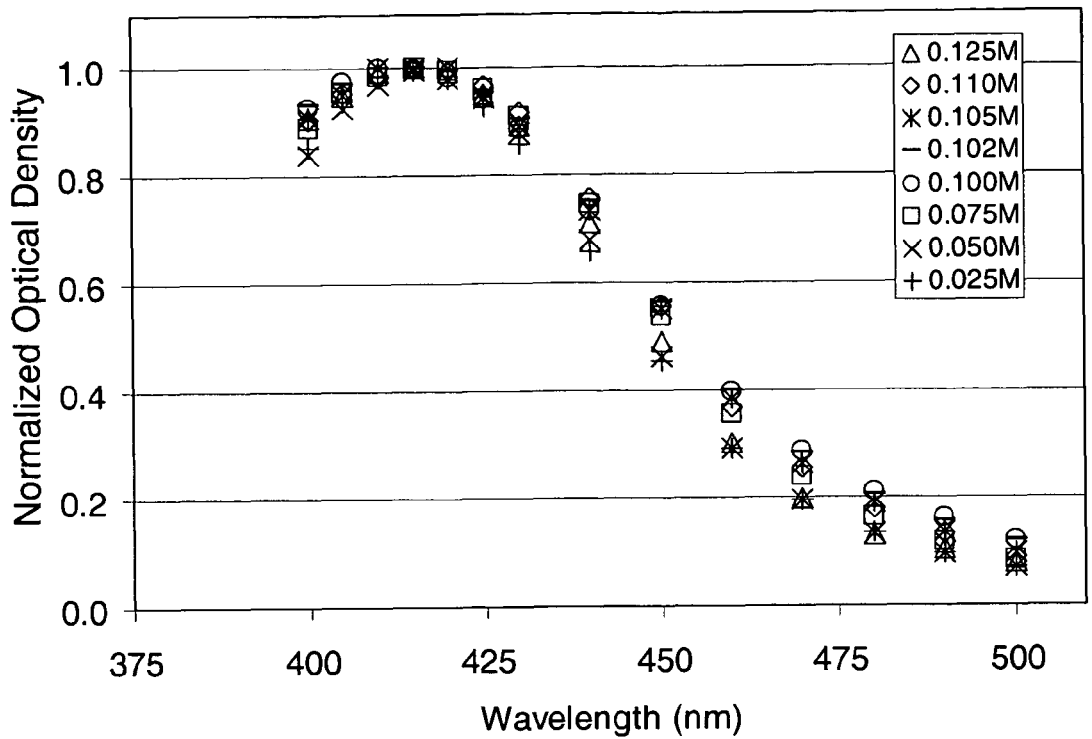
FIG. 11 shows representative spectrograms obtained by UV-Visible spectroscopic analysis of various aqueous antimicrobial silver nanoparticle compositions in accordance with the present invention, wherein the various aqueous antimicrobial silver nanoparticle compositions were prepared from solutions comprising silver nitrate at a fixed concentration of 0.1 M and sodium saccharinate at concentrations as indicated.

The silver nitrate concentration was held at 0.1M and the sodium saccharinate concentration was varied to maintain ratios of saccharinate to nitrate between 0.025M and 1.25 to test the effect of modifying the saccharinate concentration (Table 4). Though, higher non-limiting ratios of saccharinate salt or salts of other anions preferably up to 5 times the preferred concentration can be used without departing from the scope of the invention. Ratios other than specified here may also be used. In all cases, whether the ratio was >1 or <1, yellow brown colored silver nanoparticles solutions were obtained with the debris primarily consisting of undissolved silver saccharinate. The spectra were practically the same (see FIG. 11) indicating the nanoparticles sizes and distribution were with an average size of 5-10 nm.

Effect of Silver Nitrate Concentration

Figure 12:
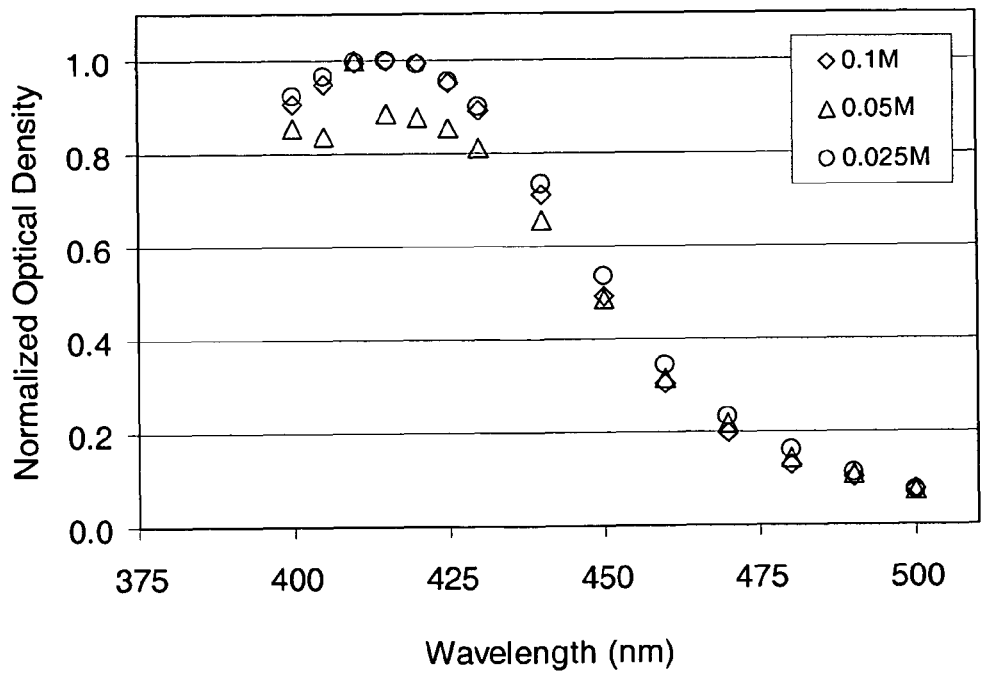
FIG. 12 shows representative spectrograms obtained by UV-Visible spectroscopic analysis of various aqueous antimicrobial silver nanoparticle compositions in accordance with the present invention, wherein the various aqueous antimicrobial silver nanoparticle compositions were prepared from solutions comprising silver nitrate at concentrations as indicated.

Keeping all other conditions including the molar ratio of saccharinate to nitrate unchanged but varying the silver nitrate concentration did not affect silver nanoparticle spectra (FIG. 12). The data once again indicated that the nanoparticle size and size distribution essentially remained unchanged. The appearance of the solution also stayed the same i.e. yellow brown with little or no debris (Table 5). These results gave the basis to use silver nitrate concentration to vary final silver nanoparticles count in the liquid composition depending on the product specification.

Effect of TEMED Concentration

In the experiments above, the TEMED to silver nitrate solution volume ratio 1:10. Here that ratio varied between 2:10 to 4:10 and looked for any changes in nanoparticle solutions formed (Table 6). Visually, the solutions remained similar but we also observed a purple tint on vial walls when we increased TEMED concentration.

Figure 13:
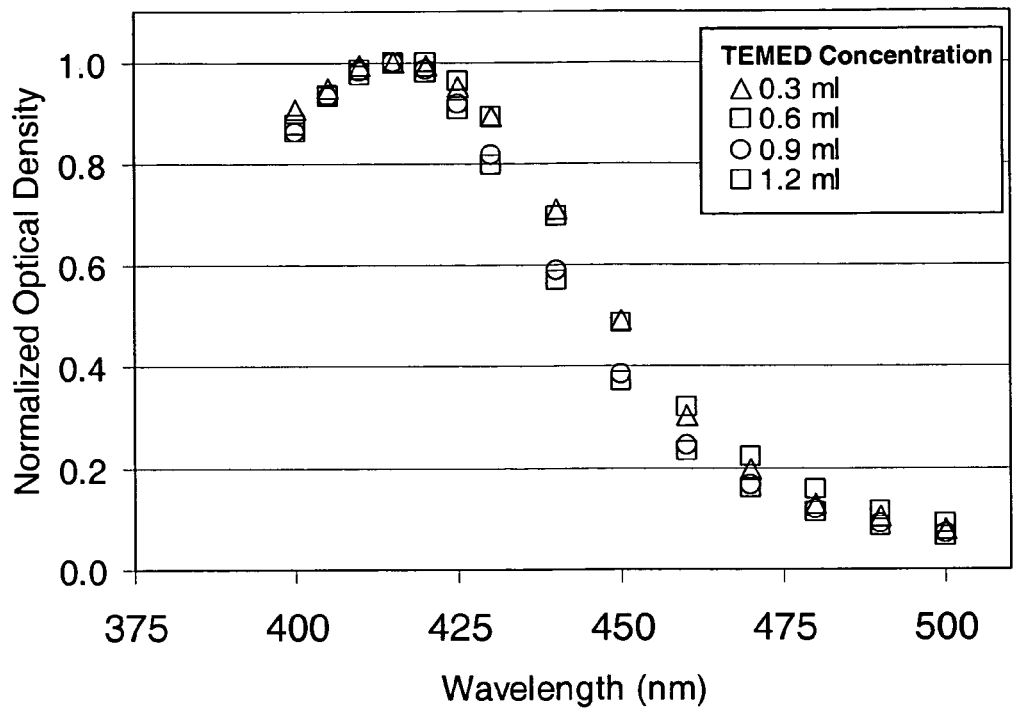
FIG. 13 shows representative spectrograms obtained by UV-Visible spectroscopic analysis of various aqueous antimicrobial silver nanoparticle compositions in accordance with the present invention, wherein the various aqueous antimicrobial silver nanoparticle compositions were prepared from solutions comprising TEMED (CAS No. 110-18-9; $C_6H_{16}N_2$; known alternatively as N,N,N',N'-Tetramethylethylenediamine) added in the volumes indicated.

The silver nanoparticles character (size and distribution) did not change as the spectra are identical (FIG. 13).

Effect of Order of Reagent Addition

From a process point of view, it is important to know if the order of reagent addition matters in the final outcome. For example, in a manufacturing setting, the addition of the most expensive ingredient in the last step is preferred. If for any reason, the previous steps in the process have to be scrapped due to equipment malfunction or operator error, one can suspend the last step. In such instances, money can be saved by not wasting expensive reagents.

In all experiments above, we adopted Method A where silver saccharinate was formed first. In Method B, we added silver nitrate last and in varying amounts. All resulting nanoparticles solutions showed little or no debris indicating no agglomeration. No undissolved saccharinate precipitate was seen. The test tube walls also had no metallic silver deposition indicating that the nanoparticles formed stayed in solution. Out of the 4 tests performed, the one where we used nitrate and saccharinate solution in 3:4 ratio (0.75 ml in FIG. 14) gave qualitatively the best solution.

Figure 14:
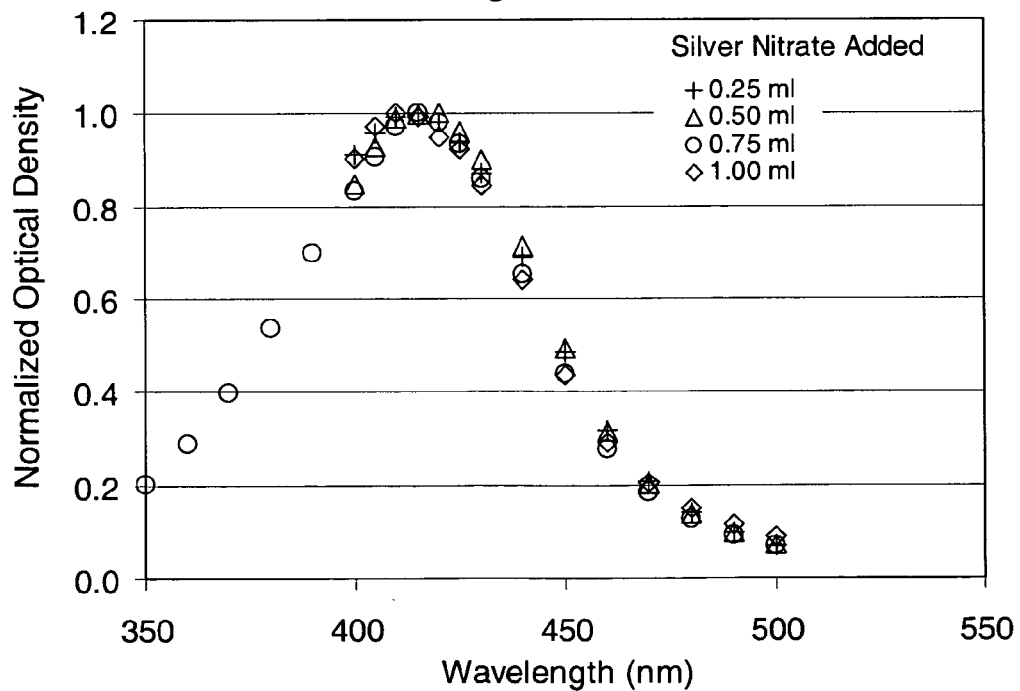
FIG. 14 shows representative spectrograms obtained by UV-Visible spectroscopic analysis of various aqueous antimicrobial silver nanoparticle compositions in accordance with the present invention, wherein the various aqueous antimicrobial silver nanoparticle compositions were prepared by reverse addition from solutions comprising addition of silver nitrate in the volumes indicated.

FIG. 14 shows spectra of four solutions prepared by reverse addition. In each case the wavelength maximum was 415 nm and the shape of the spectra over 400 to 500 nm range matched. For one solution, OD below 400 nm up to 350 nm was measured to see if there was spectral symmetry around the maximum. The graph does indicate that the spectrum is symmetrical and this observation is consistent with published reports.

In comparison to silver nanoparticle containing compositions of the prior art, the compositions of the present invention comprise silver nanoparticles in concentrations almost 4 to 15 times or in some cases even higher based on the OD values as measured by UV-VIS spectrophotometer. This higher silver concentration gives added advantage to the compositions of the present invention in its ability to impart higher silver loadings on surfaces contacting the compositions, clearly distinguishing the present invention from the prior art.

During the process parametric study, in a large number of the tests conducted there was the presence of precipitate or debris in the reaction vessel and occasionally on treated devices. However, this should not be construed as a limitation of the present invention. The precipitate present in the compositions is entirely due to the poorly soluble silver salt that is formed. By adjusting the starting concentration of soluble silver salt or by appropriate dilution, the amount of weakly soluble salt that may stay behind as precipitate can be reduced or eliminated.

Stability of Silver Nanoparticles Solutions

Figure 15:
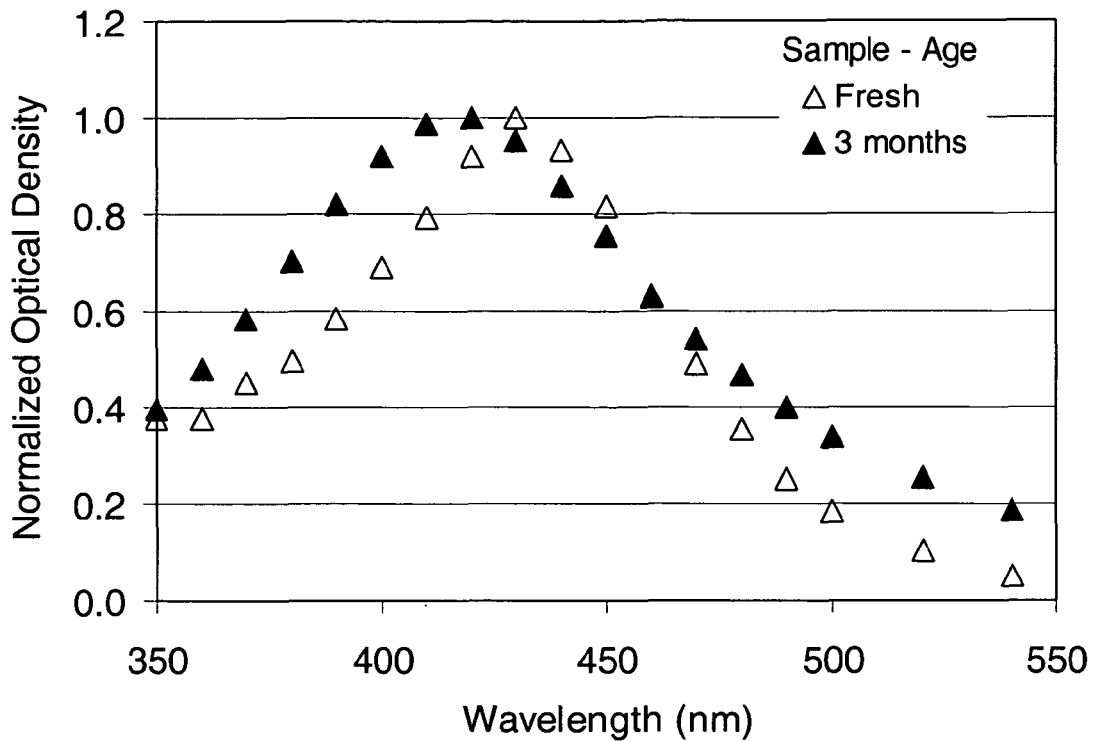
FIG. 15 shows representative spectrograms obtained by UV-Visible spectroscopic analysis of a non-aqueous antimicrobial silver nanoparticle composition in accordance with the present invention, wherein, the solvent comprised chloroform and as indicated in the figure, the non-aqueous antimicrobial silver nanoparticle composition was either prepared fresh (4 h) or analyzed at after storage at about 25° C. for about 3 months.

Another important parameter from a process point of view is the stability of silver nanoparticles solutions as a function of time. Demonstrating at least a few weeks of stability is quite important. One indirect measure of stability would be no change in UV-VIS spectrum which can be easily monitored with time. In FIG. 7 the UV/VIS spectra of saccharinate based aqueous silver nanoparticles composition made fresh and one of the same composition after 11 months period is presented. During this time, the sample vial was stored at ambient temperature (22C-25C). We observed no change in spectra between a freshly prepared solution and the stored one even after nearly a year. This data support a finding that the silver nanoparticles solutions possess excellent room temperature stability. Similarly, though there is small nominal change in the spectra, we can see fairly good stability of a chloroform based non-aqueous silver nanoparticles composition at 4C for over 3 months (FIG. 15). The overall shape of the curve does not change much indicating the particles size and distribution does not change.

Ingredients and Compositional Ranges

The antimicrobial silver compositions comprising silver nanoparticles may be derived from silver compounds formed in situ by anion exchange in an aqueous solution when a soluble silver salt such as silver nitrate and the sodium salt possessing the desired anion are mixed. For example, to form silver barbiturate, the exchange would occur between silver nitrate and sodium barbiturate. Silver compounds may be formed in situ or may be provided as final silver compounds. Silver compounds commercially available as powders or crystals can substitute the in-situ formed silver compounds in the preparation of nanoparticle compositions of the present invention. In the practice of the present invention, silver compounds as a single compound or mixtures including, but not limited to, acesulfame, alkyl carbonates, acetylacetonates, acetates, ascorbates, barbiturates, benzoates, bitartrates, bis (2ethylhexyl) sulfosuccinate borates, bromides, carbonates, chlorides, citrates, folates, fumarates, gluconates, halides, hydantoins, substituted hydantoins, iodates, iodides, lactates, laurates, oxalates, oxides, palmitates, perborates, phenolsulfonates, phosphates, propionates, saccharin and derivatives, salicylates, sorbates, stearates, succinates, sulfadiazines, sulfates, sulfides, sulfonates, and tartrates. Another feature of the method of preparation of the compositions of the present invention is that the soluble silver salt is converted to a less soluble silver salt in situ. In the formation of the less soluble silver saccharinate in the methods of preparation of the present invention, an excess of alkali metal alkaline earth metal saccharinate is maintained. The molar excess of the saccharinate ranges between ratios of 1 and 5 with the preferred ratio between 1.05 and 2.0 with most preferred ratio between 1.1 and 1.5. The anion exchanging metal salts must possess cations higher in the electronegativity scale than silver. Non-limiting examples of available metal cations are sodium, potassium, calcium, lithium with sodium and potassium most preferred. Non-limiting examples of soluble silver salts are silver nitrate, silver citrate, silver acetate with silver nitrate being most preferred. Any soluble silver salt may be employed as long as it does not create biocompatibity or toxicity problems especially in making medical products.

An important feature of the antimicrobial silver compositions of the present invention is that compositions spanning wide ranges of ingredient concentrations can be made without encountering compatibility or formulation problems. Silver content of the nanoparticles compositions can vary anywhere in the range of 0.0001% to 10%, 0.1% to 2%, 0.1 to 5%. When preparing nanoparticles compositions with high silver content such as >5%, silver may precipitate out as flakes (agglomerated state) if a sufficient amount of surfactant or stabilizer is not maintained. Its presence as such does not affect the antimicrobial property and can be removed by filtration, yielding dark amber colored silver nanoparticles compositions.

The stabilizing agents are useful in maintaining the nanoparticles compositions of the present invention and can be a surfactant or a polymer. The surfactant can be of any type-anionic, cationic, nonionic, or amphoteric. A large variety of surfactants are commercially available. Non-limiting examples of stabilizers for use in the antimicrobial silver compositions are anionic, nonionic and amphoteric surfactants. Different classes of compounds are commercially available under each type of surfactants. Among polymers, polyacrylamide and derivatives (homo- and copolymers having acrylamide moiety, acrylamide with one or two substituents on the nitrogen atom), methacrylamide polymers and derivatives (homo- and copolymers having methacrylamide moiety, methacrylamide with one or two substituents on the nitrogen atom), polyamides and derivatives, polyurethanes and derivatives, polyamines and derivatives can be used. Preferred surfactants for use as stabilizing agents are nonionic known as Polysorbates or Tween NN where NN is an integer equal to 20, 40, 60 and 80.

The surfactant or stabilizer concentration in the compositions in relation to silver content may vary between the weight ratio of 0.1 and 500 but the total stabilizer concentration should not exceed 40% of the weight of the compositions. A ratio of values of surfactant concentrations of Polysorbate type generally lies below 5% w/v in the compositions. However, when using the polymeric stabilizers the preferred values may also be higher than 5% w/v. Higher amount of stabilizer readily stabilizes silver compositions with higher amounts of silver loadings.

In most published studies on the preparation of compositions comprising silver nanoparticles a need for a reducing agent is recognized. Inorganic reducing agents have been employed but due to their strong reducing capacity, the formation of silver nanoparticles does not proceed in a controlled fashion thus yielding large size particles and often broad size distribution. Not all organic bases, when used as reducing agents, necessarily yield small and uniform size silver nanoparticles. Illustrative examples though not limiting in any way of reducing agents for use in the preparation of the antimicrobial silver compositions of the present invention are tertiary, secondary and primary amines; tertiary, secondary and primary diamines; homopolymers or copolymers having primary amine, secondary amine and tertiary amine moieties. Amine compounds may be aliphatic or aromatic. An aromatic amide such as diethyl toluamide popularly known as DEET also can be used. The preferred reducing agents are tertiary amines or diamines. Preferred reducing agents are triethanolamine and N,N,N',N' tetramethyl ethylene diamine (TEMED) with TEMED being most preferred. Polymeric compounds having a TEMED moiety in the pendant chain or in the main chain also can be employed as the reducing agent. The amount of the reducing agent in the compositions again in relation to silver can vary between the weight ratios of 0.1 and 500 with the preferred ratio between 2 and 50 and most preferred ratio between 4 and 20. The reducing agent can be added neat or in a diluted form. Both these variations are encompassed by the present invention.

Non-limiting examples of the solvent bases for the antimicrobial silver compositions are water or water based solutions where water is at least the major component. Other miscible solvents such as lower alcohols ($C_6$ or less), lower diols ($C_6$ or less), THF, DMSO, DMF etc. can be used either singly or as multi-component mixtures with water. Non-limiting examples of non-aqueous solvents or mixtures thereof are chlorform, methylene chloride, acetone, methyl ethyl ketone, cyclohexane, ethyl acetate, diethyl ether, lower alcohols ($C_4$ or less), lower diols ($C_4$ or less), THF, DMSO and DMF. A variety of solvents that are HAPS free as defined under the clean air act of 1990 can be utilized in the preparation of non-aqueous silver compositions of the present invention.

Antimicrobial Medical and Non-Medical Devices

One embodiment of the present invention comprises medical devices that are rendered antimicrobial using methods comprising contacting the surfaces of the devices with the nanoparticles compositions. Medical devices, without limitation, include catheters (venous, urinary, Foley or pain management or variations thereof), stents, abdominal plugs, cotton gauzes, fibrous wound dressings (sheet and rope made of alginates, CMC or mixtures thereof, crosslinked or uncrosslinked cellulose), collagen or protein matrices, hemostatic materials, adhesive films, contact lenses, lens cases, bandages, sutures, hernia meshes, mesh based wound coverings, ostomy and other wound products, breast implants, hydrogels, creams, lotions, gels (water based or oil based), emulsions, liposomes, ointments, adhesives, porous inorganic supports such as titania and those described in U.S. Pat. No. 4,906,466, the patent incorporated herein in its entirety by reference, chitosan or chitin powders, metal based orthopedic implants, metal screws and plates etc. Synthetic fabrics, those based on nylon or its blends with other fabric making materials (silk, rayon, wool, bamboo, polyester, acrylic, acetate) impregnated with silver nanoparticles are contemplated by the present invention. Devices, medical including dental and veterinary products and non-medical, made of silicone, polyurethanes, polyamides, acrylates, ceramics etc., and other thermoplastic materials used in medical device industry and impregnated with silver nanoparticles using liquid compositions of the present invention are encompassed by the present invention. Various coating compositions for different polymeric or metal surfaces that can be prepared from liquid compositions are also covered by the present invention. Such coating compositions can be hardened by solvent loss or cured by thermal or radiation exposure. Another aspect of the present invention are the blends of antimicrobial liquid compositions of the present invention and other antimicrobial agents such as glasses and zeolites similar to those disclosed in U.S. Pat. No. 6,248,342 and U.S. Pat. No. 5,049,139 and incorporated in their entirety herein by their reference.

Antimicrobial medical and non-medical devices of the present invention can be made by treating the devices with antimicrobial silver compositions of the present invention by different methods. One disclosed method of the present invention comprises steps of making the said compositions in liquid form, contacting the said compositions and the devices surfaces for a sufficient period of time to allow accumulation of nanoparticles and then rinsing the excess of said composition away and drying the device. A modification of the disclosed method may involve drying the surface of material first and then rinsing off the surface to remove excess. The method of contact may be dipping the device in the said compositions or spraying the compositions on the device or coating blends of polymer solution and said compositions. A variation of the disclosed method can be employed to deposit different loadings of silver on the surface of tubing. For example, initially, one level of silver loading can be applied over the entire length of the tubing. Then, if needed, a second application can be made over $\frac{2}{3}^{rd}$ length of the tubing and finally only a $\frac{1}{3}^{rd}$ portion of the tubing may be treated yielding a tubing with three levels of silver loadings. Using this approach any particular deposition pattern of silver loading can be achieved. A similar approach can also be implemented over a flat material creating different silver loadings pattern over the entire area. One embodiment of the present invention having three levels of silver loadings can be a bathroom product such as shower curtain. In such a product, the lower portion can be loaded with the highest level, the middle portion with intermediate level and the top portion with smallest level of silver. Such silver based curtain will prevent the mold and mildew formation on the curtain.

Yet another modification of the above disclosed method comprises steps of pre-treating the device surface with an agent that enhances the adhesion of silver nanoparticles to the surface or primes the surface to catalyze the silver nanoparticles formation by reduction of the silver salt amine complex that adsorbs on the surface. For example, g-aminopropyl triethoxysilane or similar type of adhesion improving agent, preferably a polar compound, can be used. In another situation, the surface can be primed by treatment with an aqueous solution of tin chloride, rinsed with water, dried and subsequently treated with the aqueous silver nanoparticles composition, washed and dried to complete the silver deposition on the surface. In place of tin chloride, other agents such as gold, platinum, palladium, copper compounds can be used.

An important feature of the method of the present invention disclosed above is to deposit very small levels of silver loading uniformly on a surface. The surface may comprise a flat area, or belong to a sphere, cylinder (solid or hollow) and can possess nanometer sized features or micron sized features. The surface silver loading levels contemplated by the invention range from 0.1 ug/cm2 to 100 ug/cm2 with 0.5 ug/cm2 to 50 ug/cm2 the preferred range and 5 ug/cm2 to 30 ug/cm2 being the most preferred range.

A method of preparing antimicrobial medical devices such as hydrophilic foams, sheet dressings, fabrics, gauzes comprises of the following steps: immersing the dressing in antimicrobial aqueous composition, draining the excess liquid or blotting it away, then re-immersing in a second non-aqueous liquid such as ethanol, isopropanol or THF for a period effective enough to destabilize the silver nanoparticles, thereby depositing them permanently on the substrate, blotting away excess liquids and finally drying the substrate device. A modification of the method may comprise adding the antimicrobial silver nanoparticle composition to the starting mixture of ingredients to prepare a device (e.g. a polyurethane based foam).

A method may comprise forming a liquid layer or film of the pre-mixed composition (composition that is not yet subject to a temperature increase) on the desired surface and then using known means to rapidly cause a temperature increase of the liquid film or layer to initiate silver nanoparticle formation in the vicinity of the surface to which the nanoparticles irreversibly adhere to yield an antimicrobial surface. The means to rapidly increase temperature may include acoustic radiation, microwave radiation and IR radiation or other electromagnetic radiation. Thermal energy can also be provided by way of an oven-like environment.

Yet another method disclosed for rendering medical devices antimicrobial particularly those that can withstand higher temperatures (without losing dimensional integrity) comprise the steps of preparing the pre-mix composition, heating the medical device to uniform temperature, spraying or dipping the device with the pre-mix composition to initiate rapid reduction of the silver compound in the liquid film adhering the devices surface to silver nanoparticles that irreversibly attach. If the device is dipped then it can be removed from the bath to dry the liquid film and the devices surfaces rinsed cleaned with water or other solvents. If the warmed device is sprayed then the liquid will be evaporated off from its surfaces. The surfaces can be rinsed with water or similar solvents. The rinse solution may be plain water or may comprise other additives such as surfactants, acids or complexing agents.

Modifications of the methods of the present invention for rendering certain hydrophobic polymers antimicrobial may be required. For example, silicone polymer surfaces may not readily becoming antimicrobial by immersion in aqueous silver compositions. One disclosed embodiment comprises a method comprising the steps of immersing the silicone polymer in a swelling solvent (that is also miscible with water) to effectively fill the pores with swelling solvent, transferring the swollen silicone polymer substrate quickly and immersing it in the aqueous silver composition of the present invention for a specified period to cause the exchange of solvent within the pores. As a result, the silver nanoparticles from the aqueous composition are drawn into the pores thus rendering the silicone polymer surface antimicrobial.

Medical devices or non-medical devices of the present invention can also be treated with non-aqueous silver compositions. Often the devices comprising alginates or CMC either as fibers or foam fibers are not suitable for treatment using aqueous compositions as they are unusable after coming in contact with water rich composition. Instead such devices can be conveniently treated with non-aqueous silver compositions by dipping method or spraying the compositions on the substrates. After removal of solvent that occurs by evaporation under normal conditions or by vacuum, the surfaces of the devices are impregnated with silver nanoparticles and becoming antimicrobial. Non-aqueous compositions can also be used to treat medical devices made from other polymers so long as the non-aqueous solvent is a non-solvent for that polymer or does not diffuse into the device and cause swelling. Non-aqueous silver nanoparticle compositions can also be used in situations where swelling is not detrimental. For instance, PTFE films can be rendered antimicrobial by briefly dipping them in a chloroform solution of silver nanoparticles. Such solution also can be sprayed to yield pale yellow colored PTFE.

Yet another distinguishing feature of the present invention is a method of forming silver nanoparticles in situ on the surface of a medical device. For instance, one disclosed embodiment comprises a method of yielding an antimicrobial surface comprising the steps of providing a surface coating comprising finely dispersed particles of the silver compound and treating the coated surfaces with a reducing agent for a specified period or until all of the silver compound is reduced to silver nanoparticles predominantly monodisperse in size. Preferred but non-limiting example of silver compound that can be used in such a method is silver saccharinate. The preferred reducing agent is TEMED especially to carry out the reduction at room temperature. Though not limiting, room temperature is preferable for this method though higher temperatures can be employed without departing from the present invention. The silver nanoparticle compositions can be formed in situ in a polymeric coating or in porous matrices such as ceramics, clay, zeolites, alumina, silica, silicates with finely divided silver compounds and saccharinate in particular by reduction with TEMED or similarly listed amine compounds.

Utilizing the methods of preparation of the present invention rendering a device surface antimicrobial can yield different amounts of silver loading depending upon the treatment conditions. However, a commercial process requires that the silver loading meet the specifications. In the instances where the silver loading may exceed the upper specification limit, the product batches may be rejected incurring significant costs. In such instances, it is desirable that the product batch be re-treated to bring the silver loading within the specification. One disclosed method of the present invention to re-treat the device surface impregnated with excess silver nanoparticles comprises the steps of, (a) preparing a solution of 0.5% to 15% nitric acid,
(b) treating the device surface with the said nitric acid solution for a specified period by immersing the surface in the solution and,
(c) thoroughly rinsing the device surface with deionized water and drying.

This method can remove the impregnated silver selectively in small portions and also can be utilized to completely strip the silver off the device surface or to clean production equipment. This method also can be used to strip silver off of a treated surface to create patterned surfaces bearing silver nanoparticles.

Another embodiment of the present invention discloses a method for altering the amber or yellow brown color of the antimicrobial medical and non-medical devices deposited with silver to improve their aesthetic appeal. Yet another feature of the present inventive method is that it can cause uniform color loss of amber color of the silver nanoparticles bearing surfaces without loss of silver. Even very hard to reach surfaces typical of some pre-formed micron sized objects can be readily treated as the peroxide solution can readily penetrate and wet most surfaces. The inventive method comprises following steps of, (i) preparing an aqueous solution of hydrogen peroxide in appropriate concentration,
(ii) treating the amber colored surfaces comprising silver nanoparticles for a specific period,
(iii) rinsing off the treating solution thoroughly with deionized water and drying the surfaces.

The hydrogen peroxide concentration in the treating solution can be varied from as low as 3% to 30% by weight. The time period of contact of surfaces with the treating solution will be dictated by the peroxide concentration in solution. For instance, the rate of color loss of amber color is slower at low peroxide concentration and vice a versa. The duration of contact also depends upon the product specification. If a product needs to be distinguishable as a silver containing product from non-silver containing product one may want to terminate the peroxide treatment to leave behind a faint yellow tint to the surface. In addition to water as the solvent for peroxide solution, small quantities of solvents miscible with water (but those non-reactive to peroxide) may be added.

One may provide hydrogen peroxide as vapors with or without an inert carrier such as nitrogen to cause contact with the surfaces to be treated without departing from the scope of the invention. The use of temperatures above and below room temperature in the peroxide treatment of silver nanoparticles comprising surfaces are also encompassed by the present invention. Other methods such as the use of ultrasonic energy to increase the color loss by peroxide treatment also can be employed. Patterning surfaces bearing silver nanoparticles by the hydrogen peroxide vapors or aqueous solutions by appropriate masking is covered by the present invention.

It can be used to create foam or porous matrix that can be simply added to non-potable water to disinfect it. Such a product may be more appealing to campers over current iodine based products as there water with trace amount of silver has no taste. In the construction industry, for the control of mold and mildew in homes the wooden structures during construction may be sprayed with antimicrobial silver compositions of the present invention.

The present invention also contemplates antimicrobial radioactive silver ($^{110m}$ Ag) compositions and their methods of preparation. In the use of these compositions, the antimicrobial property can be a concomitant property. These compositions can be used to prepare radioactive tracers comprising $^{110m}$Ag nanoparticles. One potential use of these compositions is to prepare labels with small amount of $^{110m}$Ag nanoparticles adhering to them. Such labels can be readily prepared by spitting tiny drops of the solution on the label surfaces by inkjet printing methods. Such labels can then be used where a product has shelf life equal to the half life of $^{110m}$Ag. Because the amount of radioactive $^{110m}$Ag is so small there is practically no risk of harm to consumer or to the product. They also may be used as tracers in security applications e.g. in authentication.

One embodiment comprises a method of preparation of antimicrobial radioactive $^{110m}$ Ag nanoparticles composition comprising the steps of,
(i) preparing a stabilizer solution,
(ii) successively adding to it the sodium or suitable metal saccharinate solution, $^{110m}$ Ag nitrate solution, reducing agent solution and,
(iii) causing a temperature increase to initiate reduction of in-situ formed weakly soluble silver saccharinate to form silver nanoparticles.

Optionally the temperature increase may be for a brief period or may be maintained for a specified period.

Mechanism of Silver Release from Solid Surfaces

An aspect of the nanoparticle compositions is their ability to efficiently deposit silver on solid surfaces in the form of very small nanoparticles that adhere to surfaces very strongly. Not only does the deposition of silver nanoparticles take place, simple handling will not dislodge the particles from the surface. They even cannot be readily removed by ultrasonication suggesting practically irreversible binding of silver to the surface. However, the particles dissolve if chemically treated.

Figure 16:
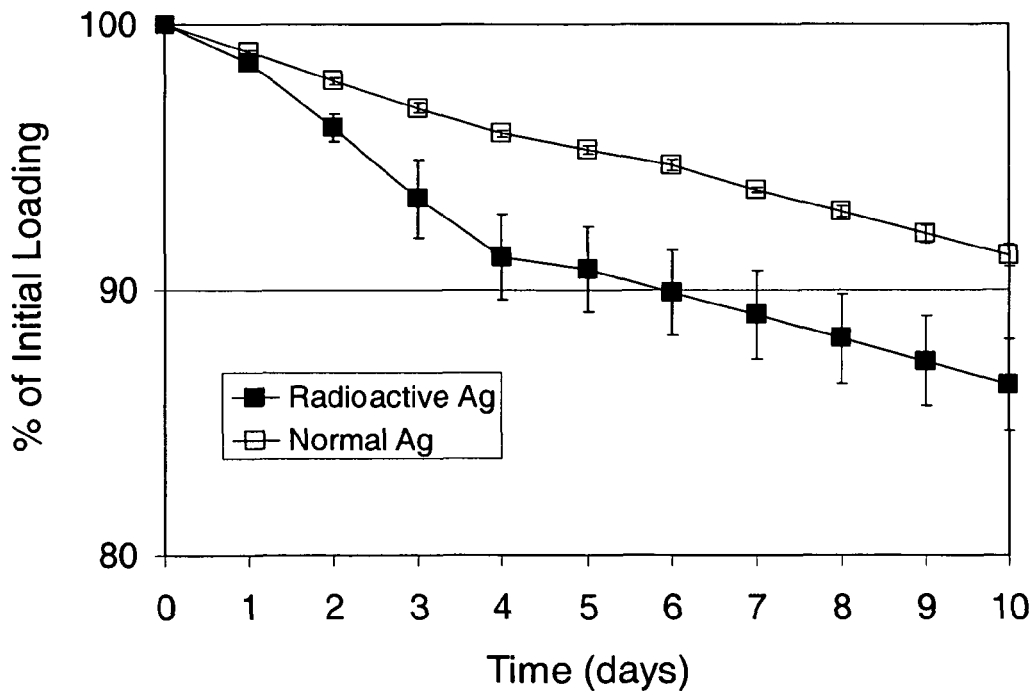
FIG. 16 shows a representative experiment measuring the release of non-radioactive ("normal") and radioactive silver from a nylon surface comprising an antimicrobial silver nanoparticles composition in accordance with the present invention.

While the presence of elemental silver on the surface would generally make that surface at least bacterio-static, it would not necessarily make it bactericidal. Even if it did, it would be extremely difficult to sustain such an action. Increasing silver loading may increase sustained release but it also increases the risk of cytotoxicity in end use. The antimicrobial silver compositions of the present invention possess the ability to impart antimicrobial characteristic to surfaces that can sustain the activity for long periods without being cytotoxic to mammalian cells. This ability is a major advance over prior art. FIG. 16 shows the amount of silver released (as ions) each day from a nylon surface treated with said antimicrobial silver composition. There is sustained prolonged antimicrobial activity because the only change taking place on the surface after treatment with the compositions is the impregnation by silver nanoparticles. As the activity is due to silver ions, it is clear that the only source of silver ions is the silver nanoparticles. The results indicate that an effective amount of silver ions is released on a continuous basis over long periods. The results were also confirmed by a test carried out using nylon tubing impregnated with radioactive silver nanoparticles. The release characteristics of radioactive silver (FIG. 16) at similar silver loading are comparable to those observed earlier.

Because it is well established that it is the silver ions ($Ag^+$) that bring about the antimicrobial action not $Ag^0$, it is believed that the source of antimicrobial silver ions are the silver nanoparticles residing on the surface. Published work has pointed to catalytic oxidation of the nanoparticles surfaces causing ionic silver to be released into the solution (Kapoor, Langmuir, Vol. 14, pp 1021-1025, 1998). Others have pointed to silver nanoclusters with positive charges forming during the reduction step (Ershov and Hengelein, J. Phys. Chem. B, Vol. 102, pp 10663-10666, 1998). Regardless of the precise mechanism, the present results show without question, sustained release of ionic silver. Theoretical estimates show that at the observed rate of egress of silver from the surface, it would take over 150 days to completely deplete the silver, which is extraordinary.

Other Applications

The antimicrobial silver compositions of the present invention can also be the starting material for producing dry silver nanopowders suitable for material science and metallurgical applications. Such compositions, aqueous or non-aqueous could be atomized in high temperature environment to produce dry silver nanopowder. The compositions of the present invention can be produced on a large scale and, because they are prepared from relatively inexpensive chemicals, a commercial process could be quite feasible and could compete with other dry processes for silver nanopowder. Another advantage of the compositions of the present invention in producing dry silver nanopowders is that the nanoparticles average size of ~10 nm is small and the size distribution is relatively tight—two factors that could offer competitive edge over silver nanopowders with broad size distribution produced by dry processes.

Other applications for silver nanoparticles comprising compositions of the present invention are in the catalysis of oxidation of olefins, separation of olefinic compounds, as polishing slurries, dissipation of static charge from surfaces, increasing thermal conductivity of liquids, increasing electrical conductivity, in the preparation of radio frequency or similar radiation shields, in analytical chemistry for surface enhanced Raman spectroscopy.

Microbiological Testing

The antimicrobial activity of device prototypes made with antimicrobial silver compositions was verified by standard zone of inhibition microbiology assay using *Staphyloccocus aureus* ATCC 6538 bacteria. Disks of ~5-7 mm size were cut from samples and placed on a Mueller Hinton Agar (MHA)

plates that were inoculated with bacteria and incubated overnight at 37C. Disk from which silver ions were released showed a clear zone around them. Untreated samples and Silvasorb served as negative and positive control respectively. The results from zone of inhibition assays are presented in Tables 7 and 8. Because the device prototypes comprise silver nanoparticles and not silver salts, ZOI assay may not be the most suitable screening assay for antimicrobial activity. Therefore, often we employed a bacterial challenge test to evaluate microbiocidal activity and sustained release characteristics. In an 8 hour bacterial challenge assay, catheter sample pieces were immersed in culture medium in tubes and inoculated with bacteria. The tubes were incubated at 37C for 8 hours after which aliquots of culture medium were diluted and spread on MHA plates and the numbers of bacterial colonies grown after 24 hour5s were counted to determine the kill rate.

Liquid compositions with slightly different compositions (see descriptive examples) were prepared quite readily and used to impregnate variety of substrates with silver nanoparticles including cotton gauze, nylon fiber and contact lenses and hydrogel sheet. All prototypes including amorphous talc powder showed zones of inhibition and sustained release antimicrobial

TABLE 7

ZOI Assay using *Staphylococcus Aureus*
(Zone of inhibition + disk dia/disk dia)

| Example | Substrate | ZOI data |
|---------|-----------|----------|
| A1 | Cotton gauze | 9.5/7.0 |
| A2 | Cotton gauze | 9.0/6.5 |
| A3 | Contact lens | 8.0/6.5 |
| A4 | Si catheter | 4.5/4.0 |
| A5 | Hydrogel | 16.0/8.5 |
| A6 | Contact lens | 9.0/6.5 |
| B1 | Hydrophilic polymer | 8.5/6.0 |
| B2 | Hyd. Poly w/copper | 10.0/5.0 |
| B4 | Talc powder | 7.5/7.0 |
| A9 | Catheter w/hyd. Poly. coating | 6.0/4.5 |
| A10 | Contact lens | 10.0/6.0 |
| A11 | Cotton gauze | 4.0/1.0 |
| A12 | Cotton gauze | 3.0/1.0 |
| A13 | Contact lens | 11.0/7.0 |
| A15 | Nylon catheter | 3.0/1.0 |
| A16 | Nylon catheter | 7.0/1.0 |
| B9 | Lubricating jelly | 6.0/5.0 |
| B10 | Alginate beads | 7.0/3.0 |
| A18 | Breast implant membrane | 8.0/6.0 |
| A7 | Nylon fiber | 4.0/1.0 |
| B15 | Polypropylene woven fabric | 9.0/7.0 | activity against *Staphylococcus aureus* (see Table 7). In silver nanoparticle containing articles, the antimicrobial activity is also sustained for 4 days as evident from the results in Table 8. In the case of some substrates such as fiber, catheter and lens, the antimicrobial activity was tested by the bacterial challenge test. In such a test, the substrates are challenged with known bacterial count while immersed in medium for 24 h. The medium was then appropriately diluted and plated on MHA plates to estimate the surviving bacterial count. The challenges were continued until the substrates are exhausted of an effective amount of silver. The bacterial challenge test results (Table 9) show that silver ions release from nanoparticles embedded in substrate surface occurring over 11 challenges i.e. 11 days. In contrast, similar commercial products (Bardex & Lubrisil I.C. catheters) lasted only 3 days.

TABLE 8

Examples of Serial Transfer Results
Against *Staphylococcus Aureus*

| Example | Substrate | Day 1 | Day 2 | Day 3 | Day 4 | Day5 |
|---------|-----------|-------|-------|-------|-------|------|
| A6 | Contact lens | 13.5/6.5 | 9.0/6.5 | 7.0/6.5 | 6.5/6.5 | — |
| B1 | Hyd. polymer | 13.5/5.5 | 8.5/6.0 | 6.0/5.5 | — | — |
| B2 | Hyd. polymer w/copper | 12.0/5.0 | 10.0/5.0 | 8.0/5.0 | 7.0/5.5 | 5.5/5.5 |

Biocompatibility of medical devices with tissues is important. The agarose overlay assay is used to quantify the inherent level of cytotoxicity present in device. The results from agarose overlay tests verified that silver nanoparticle containing substrates are non-cytotoxic as well as non-irritating. The strength of association between the silver nanoparticles and the substrate surfaces. The sonication of silver treated nylon fiber had no effect on antimicrobial activity and repeatedly washing of the gauze did not result in loss of activity. The results summarized here clearly demonstrate that liquid compositions containing silver nanoparticles are stable, can be made very easily and cheaply and can be used to make a host of devices' surfaces antimicrobial. In general, the present invention comprises compositions comprising nanoparticles. Nanoparticle compositions comprise a solvent, a silver nanoparticle, and a stabilizing agent. After formation of the nanoparticles, there may be residual or unreacted reducing agent remaining in the composition. It is understood that a large number of nanoparticles form in the composition. The solution may aqueous or non-aqueous. Aqueous solvents include water, and non-aqueous solvents include methylene chloride, chloroform other aliphatic and aromatic chlorinated solvents, cyclohexane, diethyl ether, ethyl acetate and mixtures thereof, stabilizing agents, stabilizers, or other similar terms, which are used interchangeably include a polymer, a surfactant or both. Polymers include a homopolymer copolymer, synthetic or naturally derived, polymers of acrylamide and its derivatives, methacrylamide and its derivatives, polyamides, polyurethanes, polymers having no particular backbone but with urethane segments or tertiary amine groups in the side chains, other polymers predominantly polar in nature or copolymers having a portion that is derived from polar co-monomers, methaacrylamide, substituted acrylamides, substituted methaacrylamides, acrylic acid, methacrylic acid, hydroxyethyl methacrylate, acrylonitrile, 2-acrylamido-2-methylpropane sulfonic acid and its salts (sodium, potassium, ammonium), 2-vinyl pyrrolidone, 2-vinyl oxazoline, vinyl acetate, maleic anhydride. Surfactants may be anionic, nonionic, or amphoteric surfactants.

Methods of making silver nanoparticles comprise a) adding in no particular order, an aqueous solution of a stabilizing agent solution, an anionic donating solution and a soluble silver salt solution, and b) adding a tertiary diamine solution, and further c) heating the final solution to increase the reaction. The method further comprises forming the nanoparticles in situ on the surface of an article. The articles may be a woven or nonwoven fiber article article. The article may be a medical device, polymer, a fiber, a metal, glass, ceramic, fabric or combination thereof.

The nanoparticles may be extracted into a non-aqueous solution. The invention also comprises methods of treating a surface with silver nanoparticles, comprising, a) contacting a surface with a solution comprising silver nanoparticles for a time sufficient for an effective amount of nanoparticles to bind to the surface, and b) rinsing the solution from the surface. The steps of contacting and rinsing may be repeated multiple times to increase the number of nanoparticles adhering to the surface. The surface contacted may be a medical device or any of the other articles or surfaces taught herein. The method further comprises, contacting the surface with nanoparticles adhered thereto with an aqueous solution of hydrogen peroxide for a sufficient period of time, and, rinsing the hydrogen peroxide solution from the surface, wherein the surface contacted may be a medical device, polymer, a fiber, a metal, glass, ceramic, fabric or combination thereof.

It must be noted that, as used in this specification and the appended claims, the singular forms "a", "an", and "the" include plural referents unless the context clearly dictates otherwise.

All patents, patent applications and references included herein are specifically incorporated by reference in their entireties.

It should be understood, of course, that the foregoing relates only to exemplary embodiments of the present invention and that numerous modifications or alterations may be made therein without departing from the spirit and the scope of the invention as set forth in this disclosure.

Although the exemplary embodiments of the present invention are provided herein, the present invention is not limited to these embodiments. There are numerous modifications or alterations that may suggest themselves to those skilled in the art.

The present invention is further illustrated by way of the examples contained herein, which are provided for clarity of understanding. The exemplary embodiments should not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

EXAMPLES

Antimicrobial Device Examples A1-A37

Example A1

Cotton Gauze

Dimethyl formamide (5 ml) was heated in beaker to ~60C under stirring. After the stir bar was removed a 2"×2" cotton gauze (Curity brand, The Kendall Company, Mansfield, Mass.) was placed in DMF to soak up all solvent. Silver nitrate solution (0.3 ml, 0.1 M) was pipetted over the gauze. Within a minute the gauze turned yellow. After 5 minutes, the beaker was removed from the hot plate and cooled to room temperature. The pale yellow colored gauze was thoroughly rinsed with de-ionized water, blotted and dried in oven at 40C.

TABLE 9

Examples of Sustained Release of Silver from Bacterial Challenge Test Against *Pseudomonas Aeruginosa* ATCC 9027(Each challenge is 24 h)
Table 3: % Kill Rate of *Pseudomonas Aeruginosa*

| Challenge No. | Inoculation size (cfu/ml) | Example A15 | Example A16 | Example A14 | Example A13 |
|---|---|---|---|---|---|
| 1 | 6300 | 100 | 100 | 100 | 100 |
| 2 | 4600 | 100 | 100 | 100 | 100 |
| 3 | 8700 | 100 | 100 | 100 | 100 |
| 4 | 3000 | 66.67 | 100 | 100 | 100 |
| 5 | 7000 | 100 | 0 | 100 | 97.14 |
| 6 | 8000 | 100 | 0 | 100 | 100 |
| 7 | 4000 | 100 | Stopped | 100 | 100 |
| 8 | 7000 | 100 | | 94.14 | 57.14 |
| 9 | 5000 | 100 | | 100 | 100 |
| 10 | 9000 | 100 | | 100 | 100 |
| 11 | 4000 | 100 | | 100 | 100 |
| 12 | 8000 | 54.88 | | 0 | 0 |
| 13 | 6000 | 0 | | 0 | 0 |

Bio-Film Inhibition Test

For in-dwelling medical devices such as urinary or venous catheters, having antimicrobial surface characteristics is very helpful for minimizing infections. But, even more important is the ability of such devices to prevent bio-film formation. Once bacteria have formed bio-films, they use it as shield making it difficult to get rid of them. Antibiotics or other drugs are not effective. One important distinguishing feature of the antimicrobial devices of the present invention is their ability to inhibit bio-film formation. To examine the bio-film inhibition characteristics of the antimicrobial nylon tubing, a method based on following principles was employed.

Bio-film formation can be evaluated by immersing the test article in test medium that has been inoculated with the challenge organism. After appropriate incubation, bio-film formation is assessed by determining the amount of carbohydrate specific dye that is bound on the surface of the device. There is a quantitative relationship between the extent of bio-film formation and residual carbohydrate on the surface. This can be quantified by first extracting the dye in a suitable solvent and then measuring the OD on a spectrophotometer.

Figure 17:
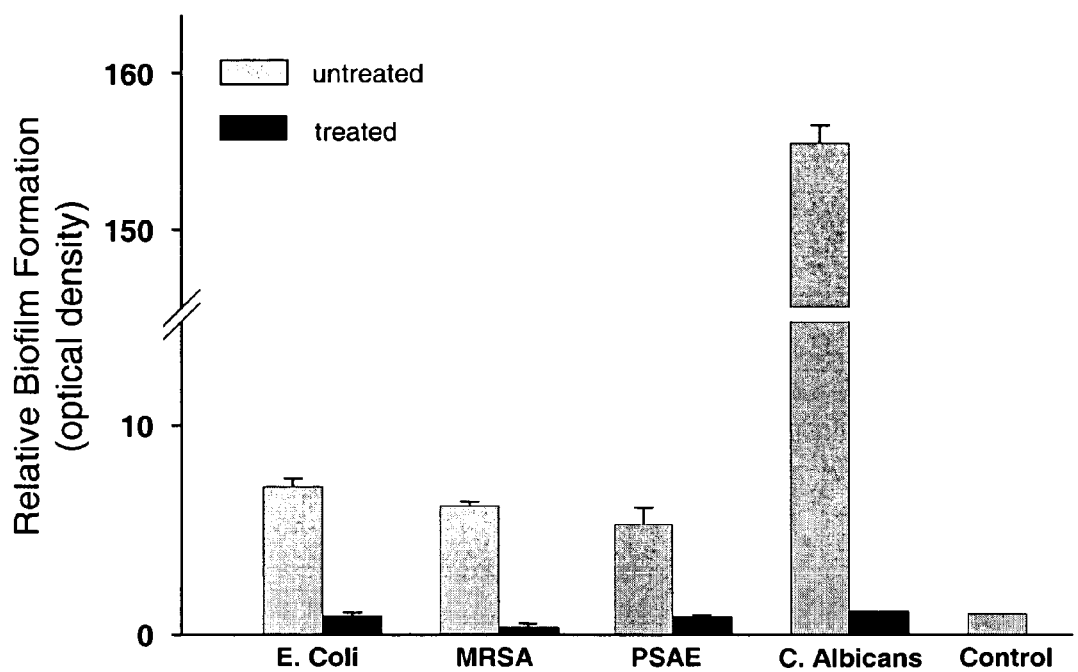
FIG. 17 shows representative results obtained for testing relative biofilm formation on nylon tubing samples comprising an antimicrobial silver nanoparticles composition in accordance with the present invention.

FIG. 17 summarizes the results of bio-film testing on nylon tubing samples with silver loading (in the form of nanoparticles) of ~600 ppm (based on the tubing weight). The silver treated samples strongly inhibit bio-film formation against, *E. Coli*, methicillin resistant *staphylococcus aureus, pseudomonas aeruginosa* and *candida albicans*. In comparison, untreated device samples show no inhibition (high OD values). The results unequivocally show the resistance of the device of the present invention to bio-film formation.

Example A2

Cotton Gauze

Gauze was treated exactly as in example A1 except the silver nitrate solution concentration was 1.0M.

Example A3

Contact Lens

Contact lens (SEE3, CibaVision Corporation, Duluth, Ga.) was rinsed clean off the preservative solution and immersed in hot DMF solution as in example A1. Under gentle stirring, silver nitrate (0.3 ml, 1.0M) was added drop-wise to the hot DMF. After 5-7 minutes, the beaker contents were cooled, lens removed and rinsed thoroughly with de-ionized water, blotted over tissue paper and dried in oven at 40C. The lens imparted pale yellow tint.

Example A4

Catheter Segment

DMF solvent (10 ml) was heated to ~100C in a beaker under stirring. Silver nitrate solution (0.25 ml, 0.02 M) was added to the hot solvent to yield silver nanoparticles as indicated by yellow color (due to plasmon resonance band). A pre-cleaned silicone catheter (14 Fr, Degania Silicone Ltd, Israel) segment ~1" long was immersed in the yellow solution for 15 minutes. The catheter segment was removed, rinsed with de-ionized water and dried. A small level of discoloration of the catheter segment was seen.

Example A5

Hydrogel Sheet—Method 1

To de-ionized water (13.3 ml) in a cup, acrylamide (1.482 g), bisacrylamide (0.018 g) and glycerol (1.5 g) were added under stirring. Separately, in hot (~60C) de-ionized water (10 ml), isopropanol and guar gum (0.165 g) were dissolved and the solution was allowed to cool to room temperature. The guar gum and acrylamide monomer solutions were mixed. To the mixture, silver nitrate (1 ml, 1.0M) and sodium saccharinate (1 ml, 0.125M) were added. With the help of a spatula, the viscous mass was mixed. Upon precipitation of silver saccharinate, the viscous mass turned whitish opaque.

To the silver salt containing mass, ammonium persulfate (0.05 g dissolved in 1 ml of water) was added followed by TEMED (0.063 ml in 1 ml of water). After TEMED addition, the mass began to slowly turn brown colored with no immediate polymerization. After 8 days, the viscous mass had converted into a brown colored hydrogel sheet.

Example A6

Contact Lens

Contact lens (SEE3 brand, CibaVision Corporation, Duluth, Ga.) was rinsed with de-ionized water to rinse off the preservative solution and then it was soaked with the silver nitrate solution (0.15 ml, 0.1M) for 10 minutes. Excess solution was drained off and sodium saccharinate (0.15 ml, 0.125M) was added to re-immerse the lens. Lens turned opaque due to the in-situ formation of silver saccharinate. Excess liquid and any loose solids were pipetted off and the lens rinsed once again with de-ionized water. TEMED (0.1 ml) mixed with water (0.2 ml) were added to soak the lens and initiate reduction. After 5 minutes, the liquid turned pale yellow. At that point, all liquid was discarded and the lens rinsed several times with water and dried overnight under ambient conditions.

Example A7

Nylon Fiber

Several strands of fibers (~1 mm dia) made of nylon (polyamide) were immersed in silver nanoparticles composition made in example B6 (total liquid volume 10 ml) for 72 hours at room temperature. The immersed fibers were rinsed thoroughly with 70% aqueous IPA and water. The fibers were also gently wiped with tissue soaked in IPA and dried for 15 minutes at 45C. The soaked portion of the fibers was colored light yellow to brown.

Example A8

Silicone Catheter Segment

4" long 14 Fr silicone catheter segment (Degania Ltd, Israel) was cleaned with IPA and dried. The segment was dipped in 5 ml THF solution of saccharin (0.5 gm) for 1 h. The shaft was removed and rinsed quickly with acetone once and immersed in silver nitrate solution (0.5 g silver nitrate, 5 ml 90% acetone/water) for 0.5 h. The shaft segment was removed and thoroughly rinsed with water and finally dipped in 30% TEMED solution in IPA. The solution was warmed to induce reduction and set aside overnight. The segment had turned yellow indicating reduction reaction had progressed. The shaft was rinsed with water and dried in oven at 125C to remove all traces of TEMED.

Example A9

Catheter with Hydrophilic Polymer Coating

A small catheter segment ~3" long with hydrophilic polymer coating (2.7% GRAFT-COAT, STS Biopolymers, Henrietta, N.Y.) was immersed in silver nanoparticles solution prepared in a manner of example B4 for 2 h. The segment was removed and washed with water and dried at 45C. Barely any color was seen initially but after several days a uniform brown color developed in the coating.

Example A10

Contact Lens

Single lens (SEE3, CibaVision Corporation) was soaked in 7 ml of the stock solution prepared in example B7 at room temperature for 12-16 h. The lens was rinsed with water and dried at room temperature. The lens was covered with a uniform shiny transparent silver coating.

Example A11

Cotton Gauze

Cotton gauze (Curity brand, The Kendall Company, Mansfield, Mass.) about 3"×3" in size was successively soaked in silver nitrate (0.1M) and sodium saccharinate (0.125M) with blotting after each soak and dried at 110C for 10 minutes. The dried gauze with silver salt was re-soaked in 30% TEMED solution in IPA for 72 h, rinsed thoroughly with water, left to soak for 24 h in water to remove solvent traces and dried. The gauze turned yellow after about 3 h soak in TEMED. The color did not leach during the rinsing and water soak steps.

Example A12

Cotton Gauze

Cotton gauze identical to the one in example 15 was soaked in PAA-silver nanoparticles solution (5 ml) prepared in a manner of example B3 for 72 h. The gauze was rinsed with water and left to soak in water for 24 h and dried. The gauze imparted orange yellow shade and did not leach any color during rinsing and water soak steps.

Example A13

Contact Lens

Clear contact lens with embedded silver nanoparticles was prepared as follows. Silver nanoparticles containing composition was prepared by dissolving Tween 20 in water (1 ml), followed by the addition of sodium saccharinate (1 ml, 0.125 M), silver nitrate (1 ml, 0.1M) and TEMED (0.1 ml). The solution (0.5 ml) after aging for a week was diluted to 2 ml with water and a pre washed contact lens was immersed in it overnight. The lens was washed with water, gently blotted and dried in oven at 75C for 0.5 h.

Example A14

Silicone Catheter

16 Fr Silicone catheter segment (~6" long) was washed with isopropyl alcohol (IPA) and dried. It was soaked in THF for 1 h to cause swelling of its walls and then dipped overnight in 1 week old silver nanoparticles solution prepared as follows. Tween 20 (0.025 g) was dissolved in sodium saccharinate solution (5 ml, 0.125M) and silver nitrate (5 ml, 0.1M) and 0.5 ml TEMED added to it. The resulting liquid was briefly heated (10 s) in microwave oven causing the solution to become yellow brown. After overnight soak, the catheter was rinsed with water, IPA and water again and dried in oven.

Example A15

Catheter—Method 1

Nylon catheter piece ~1 mm dia, 15" long (IFLOW Corporation, Lake Forest, Calif.) was cleaned with IPA and wiped dry. Catheter was soaked overnight in silver nanoparticles stock solution (90 ml) prepared according to the procedure of example B7, washed with water, IPA and wiped dry and further dried in oven at 45C. After treatment, the catheter imparted a shade of yellow.

Example A16

Nylon Catheter—Method 2

Nylon catheter segment ~4" long but otherwise similar to example A15 was briefly (1 minute) dipped in THF solution of □-aminopropyl triethoxy silane (0.1 ml silane/5 ml THF), removed and dried in air for few minutes. The silane coated sample was soaked in freshly prepared silver nanoparticles stock solution (example B7) overnight. The catheter segment was washed with water, IPA and wiped dry. The sample imparted more uniform and intense yellow color than sample of example A15.

Example A17

Silicone Catheter—Bard

Catheter segment ~3" long (Lubrisil brand, BARD Inc. Covington, Ga.) was wiped with IPA and soaked overnight in silver nanoparticles stock solution prepared by method of example A14. The segment was rinsed with water, IPA and dried in oven at 45C. It imparted pale yellow brown color.

Example A18

Silicone Breast Implant Membrane 3 pieces (~1"×1") of breast implant membrane (~0.5 to 1 mm thick) made of silicone were impregnated with silver nanoparticles by first swelling it according to the step in example A14 and soaking it overnight in silver nanoparticles solution made by the method of example B7. The pieces were washed washed with water, IPA and dried in oven at 75C for few hours. Each piece after treatment imparted pale yellow shade.

Example A19

Cyotoxicity of Nylon Fiber Strands

A silver nanoparticles solution was first prepared by mixing 0.2 gm Tween 20 in 4 ml water, adding 4 ml sodium saccharinate (0.125M), then 4 ml silver nitrate (0.1M) followed by 0.4 ml TEMED and heating in microwave oven (1500 W power) for 10 seconds and then cooling to room temperature. Four nylon fiber strands (~1 mm dia & 9" long) were immersed in the solution overnight. The strands were rinsed with water several times and dried in air. After silver nanoparticles impregnation, the fiber surface impart yellow brown color.

Using agarose overlay no cytoxicity to L929 fibroblast cells was observed. The silver content of the fiber was ~800 ppm.

Example A20

Cyotoxicity of Silicone Catheter of Example A14

Using agarose overlay no cytoxicity to L929 fibroblast cells due to the silver treated catheter was observed. The silver content of the catheter was estimated to be greater than 800 ppm.

Example A21

Effect of Sterilization Methods on Substrates with Silver Nanoparticles

Silicone catheters of Example A14 and nylon fiber strands of Example A19 were subjected to ethylene oxide (ETO) sterilization at a local facility in the Portland area. The samples saw ETO dose typical of high volume products such as medical tubings and kits.

After sterilization there was a small visually detectable change after sterilization. Both samples turned slightly darker than the original shade.

Examples A22

Attempt to "Bleach" Yellow Color of Silver Gauze Comprising Silver Nanoparticles Several pieces (3"×3") of Curity (Kendall) cotton gauze were dripped with 2 ml each of a solution comprising silver nanoparticles prepared according to the following manner: 10 ml each of stock solutions of Tween 20 (concn: 50 gm/L), sodium saccharinate (0.125M) and silver nitrate (0.1M) were mixed on vortex mixer and TEMED (1 mL) was added. The resulting solution was heated in a microwave oven for 30 seconds to yield a yellow brown solution that was cooled to room temperature.

The gauze pieces were blotted and dried in oven at 45C overnight. Upon drying some gauze color changed to light brown. The gauzes were soaked in 10% hydrogen peroxide solution (25 mL). Not color change was observed in first few minutes though after more than an hour the brown color much lighter. After 24 h soak, the gauze pieces had turned white. They were blotted and dried in oven at 45C for 1 hour and left under lab light for continuous exposure for 36 h. Except slight discoloration in few spots, the gauzes looked unchanged giving us another method of preparing silver anrimicrobial gauze material.

Examples A23

Impregnation of Silicone Catheter by Treatment with Non-aqueous Silver Nanoparticles Composition An aqueous composition similar to the one in example B13 was made and left undisturbed for over a week in a capped vial. The composition was diluted with 25 mL deionized water and extracted with ~15 mL chloroform. A portion of silver nanoparticles were extracted into the chloroform layer. A clean catheter stem made of silicone (14 Fr, Degania Ltd, Israel) was dipped into chloroform layer for 0.5 h. Immersed portion of catheter swelled due to solvent absorption. The catheter was then removed and without rinsing dried in oven at 45C for 15-20 minutes. Following treatment, it imparted faint yellow color that after 24 h turned to orange red. The color change indicated the presence of silver nanoparticles in the catheter walls. It was found to antimicrobial in 24 h bacterial challenge test.

Example A24

Silver Treated PTFE 10 ml each of stock solutions of Tween 20 (concn: 16.7 gm/L), sodium saccharinate (0.125M) and silver nitrate (0.1M) were mixed on vortex mixer and TEMED (1 mL) was added. The resulting solution was heated in a microwave oven for 60 seconds to yield a yellow brown solution. PTFE thread seal tape 4" long was wrapped around a test tube and then this tube and placed inside a large test tube and the silver nanoparticle solution was poured in both tubes to submerge the tape for 24 h and maintained at 55C. The tape was rinsed thoroughly with water several times and dried for 0.5 h at 55C.

After silver nanoparticles impregnation the tape imparted pale yellow color. It was found to be antimicrobial in a 24 h bacterial challenge test.

Example A25

Silver Treated PP 10 ml each of stock solutions of Tween 20 (concn: 16.7 gm/L), sodium saccharinate (0.125M) and silver nitrate (0.1M) were mixed on vortex mixer and TEMED (1 mL) was added. The resulting solution was heated in a microwave oven for 60 seconds to yield a yellow brown solution.

PP strip were surface treated to improve aqueous wettability as follows: 4 polypropylene strips (3"×¼) were soaked in a 80 mL 9M sulfuric acid under stirring for 40 h. Thereafter, the strips were rinsed with water several times and patted dry on paper and then air dried. Next, the strip were placed in a THF solution of g-aminopropyl triethoxysilane made by adding the silane (0.2 mL), 0.1 mL water and 0.1 mL boron trifluoride etherate to 10 mL THF. After soaking for 5 minutes, the strips were removed and air dried briefly and then at 55C for 0.5 h.

The silane treated strips were then immersed in silver nanoparticles solution made above for 4 h, rinsed, blotted on paper and air dried. Each strip imparted pale yellow color indicating impregnation of silver nanoparticles.

Example A26

Effect of <1 Ratio of Sac/Ag on Deposition of Ag on Nylon Fibers

Tween 20 solution (3 mL, 16.7 g/L), sodium saccharinate (3 mL, 0.025M) and silver nitrate (3 mL, 0.1M) were vortexed together. TEMED (0.1 mL) was added and vortexed again. TEMED addition turned the mixture pale yellow. The solution was briefly heated in microwave to ~55C and 4 clean nylon fiber strands were immersed in the hot solution for 4 h. The immersed portion of the fibers had turned blue black. The fibers were cleaned thoroughly and dried. The fibers were found to be antimicrobial in ZOI assay.

Example A27

Silver Treated Polysulfone

Tween 20 solution (2 mL, 16.7 g/L), sodium saccharinate (2 mL, 0.125M) and silver nitrate (2 mL, 0.1M) were vortexed together. TEMED (0.2 mL) was added and vortexed again. The solution was briefly heated in microwave to ~70-75C cooled to 55C and then seven 6" pieces of hollow polysulfone tubes (<0.5 mm dia) were immersed in the hot solution for 4 h. The tubes were rinsed with water and centrifuged with the tubes immersed in water to clean them from the inside. The white polysulfone tubes had become yellow colored and in ZOI assay were found to be antimicrobial.

Example A28 (Prophetic)

Method of Depositing Silver on Fabrics by Treatment with Fumarate Based Composition of Example B33 and Acetic Acid Several cotton gauze pieces (2"×2" from Bulkee II gauze roll) are treated with the silver nanoparticles composition made in example B33 by soaking in the composition for few minutes, followed by blotting and then re-soaking them in dilute acetic acid (5 ml glacial acetic acid in 100 mL water) for few minutes to precipitate out the silver nanoparticles stabilized with fumarate. After blotting on paper and drying in oven at 55C for 0.5 h, gauzes with silver are obtained as light yellow colored material. The gauzes are expected to be antimicrobial.

Example A29

Effect of Ammonia on Catheters made from PEBEX® Nylon Tubing Stock

Silver nanoparticles impregnated catheters tubing pieces (2 pieces 2" long, 1 mm outer diameter and 0.6 mm inside diameter, made from tubing stock of PEBEX® grade polyamide polymer) were soaked in dilute ammonia solution (2 mL 28% ammonia in 8 mL water) in a test tube to examine if the silver nanoparticles can be dissolved away. No change was observed in color after 16 h suggesting no effect of ~7% ammonia on silver nanoparticles impregnated on a surface.

Example A30

Silver Treated PVC Drain

Polyvinyl chloride (PVC) tubing several feet long having ¼" OD was soaked overnight in silver nanoparticles solution prepared from Tween 20 solution (160 mL, 16.7 g/L), sodium saccharinate (160 mL, 0.125M) and silver nitrate (160 mL, 0.1M) after mixing in succession and stirring together for 15 minutes. TEMED (16 mL) was added and stirred. The solution was heated in microwave to ~70-75C cooled to 55C. The tubing was removed and quenched in de-ionized water, rinsed in running water and air dried. The tubing colorless before treatment yellow and was uniform in color. It was found to be antimicrobial in bacterial challenge test.

Example A31

Silver Treated PEBEX® Grade Nylon Tubing Catheters—Conditions Versus ppm

This example describes a study carried out to examine the effects of time, starting concentration of silver nitrate and temperature on the amount of silver deposited on small dia nylon tubing material made of PEBEX® type of nylon grade. The tubing simulates a type of material used in catheters. The tubing was comprised of ~1 mm OD and 0.6 mm ID and came 27" in length.

Tween 20 solution (160 mL, 16.7 g/L), sodium saccharinate (160 mL, 0.125M) and silver nitrate (160 mL, 0.1M) were mixed in succession and stirred together for 15 minutes. TEMED (16 mL) was added and stirred. The solution was heated in microwave to ~70-75C cooled to 40-45C. A dozen or so catheter pieces were placed in a pyrex dish and weighed down (to prevent them from floating). The cooled silver nanoparticles solution was poured over the catheters in the dish and one catheter was removed at a given time point, thoroughly cleaned and air dried. The nylon tubing imparted yellow color of increasing intensity with time. The tubing samples were analyzed for silver content by AAS.

The test was repeated at 55-60C by cooling the solution to that temperature before pouring it on the catheters The silver content (as average of 3 portions—top, middle and bottom) of the catheter as function of the time of treatment at two temperatures are tabulated in Table 10.

TABLE 10

Silver Content of Nylon Tubing in ppm

| Treatment time (h) | T~40–45 C. | T~55–60 C. |
|---|---|---|
| 0.25 | 51 | 110 |
| 1 | 122 | 230 |
| 2 | 130 | 440 |
| 4 | 179 | 1017 |
| 8 | 290 | 1897 |

Example A32

Effect of Silver Concentration on Loading on the Nylon Tubing Material

To study the effect of concentration, the starting concentration of silver nitrate in preparing the treating solution was varied. For this experiment we employed radioactive silver and used counts to determine the silver content instead of AAS assay technique.

Briefly, Tween 20 solution (13.3 mL, 16.7 g/L), sodium saccharinate (1.3 mL, 0.125M) and 1.3 mL $^{110m}$Ag silver nitrate (in different concentrations), water (24 mL) were mixed in succession and stirred together for 15 minutes. TEMED (0.13 mL) was added and stirred. The solution was heated in microwave to ~70-75C cooled to 52C. To the solution were added 33 pieces of tubing material 2 cm in length and centrifuged briefly to remove air bubbles and incubated at 52C for 16 hours. The catheters were thoroughly rinsed clean and air dried.

From the counts measured and specific activity, the amount of silver deposited on the tubing was determined. The results are presented below in Table 11.

TABLE 11

$^{110m}$Ag loading in nylon tubing samples

| Sample No. | AgNO3 in treatment solution (g/L) | Ag content in tubing (ppm) (n = 5) |
|---|---|---|
| 1 | 0.755 | 1422 |
| 2 | 0.670 | 1330 |
| 3 | 0.548 | 1235 |
| 4 | 0.426 | 1019 |
| 5 | 0.296 | 876 |

Example A33

Silver Treated Nylon Tubing—Effect of Nitric Acid

A catheter nylon tubing (1 mm OD) made of PEBEX having silver loading of ~920 ppm was prepared by following procedure of Example A31. The amber colored catheter piece 1" long was immersed in 5 ml dilute nitric acid (prepared from 0.5 mL tech grade nitric acid and 4.5 mL water) overnight. The piece was washed with de-ionized water twice, then with isopropanol and dried by blowing nitrogen gas. After acid treatment, the piece was bleached to faint yellow. Silver analysis by AAS showed a loading of 350 ppm indicating a reduction of ~62% from the original loading.

This example affords a method of altering the silver loading of silver nanoparticles impregnated articles by treatment with nitric acid if the actual loading exceeds a proposed target.

During the test, we also observed the discoloration (indicating loss of silver) of the substrate due to exposure to nitric acid vapors. This result affords us a method to pattern a silver nanoparticles bearing surface by exposing them to nitric acid vapors or of other acids possessing similar characteristics.

Example A34

Silver Treated Nylon Tubing—Effect of $H_2O_2$

The nylon tubing samples deposited with $^{110m}$Ag after the egress experiment of example A32 were in this example for studying the effect of $H_2O_2$ to eliminate the amber color from the tubing surface. Just before soaking the sample tubings in $H_2O_2$, the silver loading in ppm was determined by measuring the radioactivity. The samples in separate tubes were then soaked in 2 mL 30% $H_2O_2$ solution for 24 hr at ambient temperature. Bubble formation due to oxygen was observed at the tubing surfaces often floating the tubing pieces. The next day, all samples had changed in color from amber to colorless. The radioactivity of the samples was again measured and from the specific activity, the silver loading was calculated. The results given below (Table 12) indicate the silver loss due to peroxide treatment is equivalent to the loss during 24 h saline soak. So practically, the amber color silver nanoparticle comprising surfaces become colorless without any loss of silver (or antimicrobial activity).

TABLE 12

$^{110m}$Ag content of nylon tubing samples before and after $H_2O_2$ treatment

| Sample No. | $AgNO_3$ in original treatment solution (g/L) | Ag content in tubing (ppm) (n = 5) before $H_2O_2$ treatment | Ag content in tubing (ppm) (n = 5) after $H_2O_2$ treatment |
|---|---|---|---|
| 1 | 0.755 | 1181 ± 9 | 1173 ± 10 |
| 2 | 0.670 | 1095 ± 3 | 1088 ± 4 |
| 3 | 0.548 | 1015 ± 3 | 1009 ± 4 |
| 4 | 0.426 | 800 ± 6 | 795 ± 7 |
| 5 | 0.296 | 700 ± 5 | 696 ± 5 |

Example A35

Antimicrobial Metal Implants 10 mL each of Tween 20 surfactant solution (16.7 g/L), sodium saccharinate (0.125M), silver nitrate and 20 mL de-ionized water were mixed under stirring in a beaker to yield a suspension with white particles. To the suspension, TEMED (1.5 mL) was added and briefly mixed. The content was heated for a minute in a microwave oven and the hot solution was poured on three metal implant parts placed in a glass petri-dish. The dish was covered and heated to 70C for 4 hours. Metal parts were removed from the solution, rinsed with de-ionized water several times, placed in a beaker with water and ultrasonicated for 15 minutes to remove loose particles.
The metal parts were then dried in air. The implant with silver nanoparticle impregnated surface showed antimicrobial activity against pseudomonas that sustained for 3 days. In contrast, untreated control metal part showed uncontrolled bacterial growth.

Example A36

Antimicrobial Polyurethane Foams

Antimicrobial silver nanoparticle composition was prepared by mixing 25.5 mL each of Tween 20 solution (5.2 g/L), sodium saccahrinate (0.0125M) and silver nitrate (0.01M) followed by TEMED (0.255 mL) addition and heating the mixture at 48C for 16 h. The cooled solution was used in the preparation of foams. 1" squares of Supersoft S00-T foam from Lindell Manufacturing from Michigan and Medical grade (Type 562-6) from Rynel Corporation of Maine were soaked in the silver nanoparticle compositions and blotted lightly and dried in oven at 45C for 0.5 h. The foams were found to be antimicrobial in a ZOI assay against *Staphylococcus aureus* and *Pseudomonas aeruginosa*.

Example A37

Antimicrobial Silicone Catheter Stems—Effect of Different Sterilization Processes Several stems of isopropyl alcohol cleaned silicone catheter (14 Fr, Degania Silicone Ltd., Israel) were soaked in THF for a period of 15-30 minutes. Separately an antimicrobial silver nanoparticle composition was prepared by mixing equal volumes of Tween 20 (50 g/L), sodium saccharinate (0.125M) and silver nitrate (0.1M) and then adding TEMED ($1/10^{th}$ the individual stock solution volume). The resulting mixture was briefly heated in microwave oven for 30 to 45 seconds until the solution turned yellow. The solution was cooled to room temperature and then catheter stems swollen in THF were placed in the silver nanoparticle solution overnight to deposit the particles on the silicone catheter surface. The stems were thoroughly rinsed with water and dried in air. After silver impregnation the color changed to yellow brown to grey brown. Thereafter few stems with silver nanoparticles each were sterilized by steam sterilization at 122C for 15 minutes, e-beam process (approx 30 kGy) and commercial standard ETO process. Sterilized catheter stems with silver were found to be equally antimicrobial over 7 bacterial challenges (24 h) of *Pseudomonas aeruginosa* strains with inoculation dose ~5e3 cfu/mL with 100% kill rate. None of the sterilization processes studied had adverse effect on the antimicrobial property of the catheters.

Antimcrobial Silver Compositions Examples B1-B34

Example B1

Hydrophilic Cross-Linked Polymer

To de-ionized water (13.3 ml) in a cup, acrylamide (1.482 g), bisacrylamide (0.018 g) and glycerol (1.5 g) were added under stirring. To the mixture, silver nitrate (1 ml, 0.1M) and sodium saccharinate (1 ml, 0.125M) were added. Upon precipitation of silver saccharinate, the resulting liquid turned whitish opaque.
To the silver salt containing mass, ammonium persulfate (0.05 g dissolved in 1 ml of water) was added followed by TEMED (0.113 ml in 1 ml of water). After TEMED addition, the mass began to slowly turn brown and was set aside overnight to polymerize to yield red brown colored brittle solid polymer.

Example B2

Copper Modified Hydrophilic Cross-Linked Polymer

A portion of solid polymer (~0.1 g) from Example B1 and cupric chloride solution (1 ml, 0.1M) were placed in a capped vial and set aside several days. The brown color of the polymer had changed to blue due to hydration by cupric chloride solution and the conversion of the nanoparticles to silver chloride.

Example B3

Hydrogel Sheet—Method 2

A silver nanoparticles containing polymer solution was prepared as follows. Acrylamide (0.5 gm) was dissolved in de-ionized water (5 ml). To the solution under mixing, ammonium persulfate (16 mg) and TEMED (0.02 ml) were added to form polyacrylamide (PAA) polymer solution. In the PAA solution diluted first with 5 ml water, silver saccharinate was precipitated by successively adding sodium saccharinate (1 ml, 0.125M) and silver nitrate (1 ml, 0.1M). Silver nanoparticle formation by reduction was initiated by adding TEMED (0.05 ml) to the PAA solution (indicated by the solution turning red brown). If needed, the solution was warmed to initiate reduction reaction. The solution was set aside for at least 1 day to complete the reduction.

To the PAA-silver nanoparticles solution prepared above, acrylamide (1.482 g), bisacrylamide (0.018 g) and glycerol (1.5 g) were added under stirring. Separately, to hot (~60C) de-ionized water (10 ml), isopropanol and guar gum (0.165 g) were added to form solution that was cooled to room temperature. The guar gum and the PAA-silver nanoparticles monomer solution were mixed. To the mixture, hydrogen peroxide solution (2 ml, 10%) was added causing the solution to pale from its original red brown color. Soon after adding the initiator, ammonium persulfate (0.05 g), the monomer solution with silver nanoparticles formed a red brown gel. The gel was transferred to a petri-dish and left to dry overnight.

Example B4

Talc Powder

A silver nanoparticles containing composition was prepared as follows. Surfactant Tween 20 (0.05 g) was dissolved in water (2.5 ml). To the surfactant solution, sodium saccharinate (0.25 ml, 0.125M), silver nitrate (0.25 ml, 0.1M) and TEMED (0.1 ml) were added one after another. The mixture was heated briefly in microwave oven to initiate silver salt reduction and then cooled to room temperature.

Separately, talc powder (0.5 g), IPA (1 ml) and water (4 ml) were mixed in a cup to get a uniform suspension. To the suspension 0.5 ml of the silver nanoparticles composition prepared above was added and mixed on a vortex mixer. The cream colored solids were recovered by centrifugation and drying in the oven at 45C for few hours.

Example B5

Aqueous Silver Nanoparticles Containing Composition

Sodium saccharinate (0.25 ml, 0.125M) and silver nitrate (0.25 ml, 0.1M) were added to water (1 ml) in a test tube. Tween 20 surfactant (0.05 g) was added to the resulting suspension followed by TEMED (0.05 ml) to start the reduction reaction. Within few minutes, yellow color appeared that intensified overnight. Absorbance of a diluted solution in water (dilution 1 to 5) was measured over 400 nm-550 nm range. The maximum OD was observed at 415 nm.

Example B6

Aqueous Silver Nanoparticles Containing Composition

A composition with silver nanoparticles was prepared exactly as in example 8 except the volume of sodium saccharinate, silver nitrate and TEMED was doubled. The resulting solution showed a OD maximum at ~415 nm.

Example B7

Aqueous Silver Nanoparticles Containing Stock Solution

In a cup, Tween 20 (0.5 g) was dissolved in water (10 ml). To this sodium saccharinate (10 ml, 0.125M), silver nitrate (10 ml, 0.1M) and TEMED (1 ml) were successively added. The liquid mixture was heated (30 seconds) briefly in microwave oven (Instamatic Cooking brand by Quasar) on MEDIUM setting. It turned yellow after heating due to the formation of silver nanoparticles.

Example B8

Polymer Stabilized Silver Nanoparticles Composition

Acrylamide (2.96 g) was dissolved in 25 ml of water. To the solution, ammonium persulfate (0.1 g) and TEMED (0.125 ml) were added, mixed to start polymerization. After 10 minutes, sodium saccharinate (1.25 ml, 1M) and silver nitrate (1 ml, 1M) were added to the viscous polymer solution. The solution color changed to orange red within minutes. The solution was warmed for 30 seconds in microwave oven if needed to speed up the reduction reaction. OD value peaked at a wavelength of 440 nm.

Example B9

Lubricating Jelly

Lubricating jelly (BARD Inc., Covington, Ga.) with silver nanoparticles was prepared as follows. First, the nanoparticles solution was prepared and then blended with the jelly. CMC sodium salt (0.05 g, high viscosity grade, Sigma) was dissolved in water (10 mL). To the CMC solution (1 ml), sodium saccharinate (1 ml, 0.125M), silver nitrate (1 ml, 0.1M) and TEMED (0.1 ml) were added in succession. The solution became yellow and imparted weak green fluorescence.

To the lubricating jelly (8 g) in a cup, CMC-AgNP solution (0.2 ml) made above was added and mixed to uniformity with a glass rod. The jelly with silver nanoparticles imparted pale orange tint.

Example B10

Alginate Beads

PAA-silver nanoparticles solution was prepared according to the method of example B3. The solution was added to sodium alginate solution (1 g/50 ml water). The resulting solution was added dropwise to a stirred 2% calcium chloride solution (400 ml) to form alginate beads embedded with silver nanoparticles. The beads were filtered and once washed with de-ionized water and stored wet. The beads imparted yellow color with trace green fluorescence.

Examples B11

Nail Polish Composition

A polymer used in nail polish application, Avalure 120 (1 ml) was mixed with silver nanoparticles solution (1 ml) leftover from a preparation similar to Example A19 and spread over a clean glass slide and dried at 45C. The dried film on the glass did not change color from initial yellow even after more than two months indicating that there is no agglomeration of silver nanoparticles in dried films by diffusion mechanism.

Examples B12

Silver Nanoparticles Composition from Potassium Acesulfame

A composition comprising silver nanoparticles was prepared in a dram vial by mixing Tween 20 (0.3 ml, 65 g/L), potassium acesulfame solution (1 ml, 0.125 M), TEMED (0.3 mL) and lastly adding silver nitrate solution (0.75 mL, 0.1 M), vortexing after adding each ingredient. The resulting mixture was heated in microwave oven for 10 seconds, cooled and OD measured over 400 to 500 nm. The wave length maximum was found to be 415 nm.

Examples B13

Preparation of Composition Comprising Silver Nanoparticles from Barbituric Acid

Barbituric acid (0.368 g) was weighed and added to 10 mL deionized water. Sodium carbonate (0.105 g) was added to water to convert the acid to its sodium salt as the solution became clear.

Silver nitrate (1 mL, 1M) solution was added to precipitate out silver barbiturate as fine suspension. To 1 mL silver salt suspension, 0.3 mL Tween 20 (65 g/L) and 0.3 mL TEMED were added and the mixture was heated for 10 seconds in microwave oven. A reddish orange color appeared indicating formation of silver nanoparticles. The wave length maximum was measured at 415 nm.

Examples B14

Silver Nanoparticles Composition from Sodium Saccharinate

A composition comprising silver nanoparticles was prepared in a beaker by mixing Tween 20 (1 g) in 20 mL deionized water, then adding sodium saccharinate solution (20 ml, 0.125 mL), silver nitrate solution (20 mL, 0.1M) and finally TEMED (2.0 mL). The resulting mixture was heated in on a hot plate under stirring to 60-70C over 15 min. Around 45C, the color change to yellow and continued to become darker. Some white precipitate was seen at the beaker bottom. The OD versus 1 curve measured over 400 to 500 nm was similar to a similarly made but microwaved solution. The wave length maximum was found to be 415 nm. The mode of heating did not alter the OD curve.

Examples B15

Non-Aqueous Silver Nanoparticles Composition from Sodium Oleate

An aqueous composition comprising silver nanoparticles was prepared in a test tube by mixing Tween 20 (0.3 mL, 65 g/L), sodium oleate (1 mL, 0.125M), TEMED (0.3 mL) and finally adding silver nitrate solution (0.75 mL, 0.1M) and heating it microwave oven briefly until the solution turned yellow. The OD maximum was observed at 415 nm. To the aqueous composition was added, toluene (2 to 3 mL) and vortexed to homogenize the contents that were left undisturbed for 2-3 weeks when all toluene had evaporated.

To the aqueous composition in the test tube, chloroform (3 mL) was added and shaken to extract the silver nanoparticles into non-aqueous chloroform layer. The chloroform layer turned amber brown as it gained copious amount of silver nanoparticles. The OD of the chloroform layer after dilution was measured over 300 to 550 nm. The maximum was seen at 420 nm and the shape of the curve was identical to the curve of the aqueous composition (see FIG. 1). The aqueous liquid still rich with silver nanoparticles was re-extracted with a second portion of the chloroform (3 mL) to harvest more silver nanoparticles. A 1"×1" piece of a fabric woven from polypropylene having satin like finish was dipped in the $2^{nd}$ chloroform layer and quickly removed and left to dry in air for few minutes. The fabric color changed from white to faint yellow/orange. In ZOI assay against *Staphylococcus aureus* it was found to be antimicrobial.

Examples B16

Silver Nanoparticles Composition from Hydantoin

A composition comprising silver nanoparticles was prepared from hydantoin as follows: Silver hydantoinate was first prepared according to a method disclosed in example 2 of US Patent Application No. 2003/0186955. Next, silver hydantoinate (0.05 g), deionized water (6.7 mL), Tween 20 solution (3 mL, 16.7 g/L) were mixed in a test tube and TEMED (0.3 mL) were added and contents vortexed and heated in microwave oven for 30 seconds to yield a yellow brown mixture. OD maximum of the mixture at 420 nm confirmed the presence of silver nanoparticles.

Examples B17

Non-Aqueous Silver Nanoparticles Composition

A non aqueous composition comprising silver nanoparticles was prepared as follows: Sodium oleate (3.3 mL, 4 g/L) was used as stabilizer in place of Tween 20. It was mixed with sodium saccharinate (0.3 mL, 0.125M) in a test tube. To this mixture, silver nitrate (0.3 mL, 0.1M) was added followed by water (6 mL). Finally TEMED (0.17 mL) was added. The resulting mixture was microwaved for 20 seconds to warm it and initiate nanoparticles formation. Only faint color was observed. The contents now in a beaker were heated on a hot plate to evaporate all of the water. After most of the water was evaporated the beaker was cooled and 25 mL of chloroform added to extract silver nanoparticles. The chloroform imparted yellow color indicating the presence of silver nanoparticles. OD max was observed at ~430 nm.

Examples B18

Non-Aqueous Silver Nanoparticles Composition

A non aqueous composition comprising silver nanoparticles was prepared as follows. First an aqueous composition comprising silver nanoparticles made in proportions similar to in Example B7 and allowed to evaporate to a viscous brown mass. To this mass chloroform (2-3 mL) was added to extract silver nanoparticles. At once the chloroform layer became yellow brown. OD max was 415 nm and in shape the OD vs wavelength curve was similar to that in example B15. Few drops of chloroform layer obtained were spread on a glass slide. Upon drying the film gave shiny appearance and imparted turquoise color.

Example B19

Aqueous Silver Nanoparticles Compositions with CMC as Stabilizing Agent

CMC Na salt solution was prepared by dissolving 0.05 g polymer in water (10 mL). In a test tube, CMC solution above (1 mL), sodium saccharinate (1 mL, 0.125M) and silver nitrate (1 mL, 0.1M) were mixed. Finally, TEMED (0.1 mL) was added and mixture vortexed. Yellow color change to the solution was observed within few minutes indicating nanoparticles formation. The solution color intensity increased with time. The solution also imparted green fluorescence. OD max was observed at 438 nm.

Example B20

Aqueous Silver Nanoparticles Compositions with CMC as Stabilizing Agent

In the example B19 above, the sodium saccharinate was replaced with potassium acesulfame salt solution and preparation repeated. Again yellow brown color due to silver nanoparticles in solution was observed. OD was not recorded. The preparation was repeated with potassium acesulfame salt instead of sodium saccharinate. The solution obtained once again imparted yellow brown color indicating the presence of silver nanoparticles.

Example B21

Aqueous Silver Nanoparticles Compositions with Propylene Glycol Alginate as Stabilizing Agent In the example B19 above, the CMC Na salt was replaced by propylene glycol alginate and preparation repeated. OD maximum was found to be 440 nm. The solution also imparted green fluorescence but less in intensity that in Example B 19.

Example B22

Aqueous Silver Nanoparticles Compositions using Various Surfactants as Stabilizing Agents Surfactant stock solutions were made at ~65 g/L using Tween 20, Tween 80 and Polyoxyethylene stearate.

Figure 18:
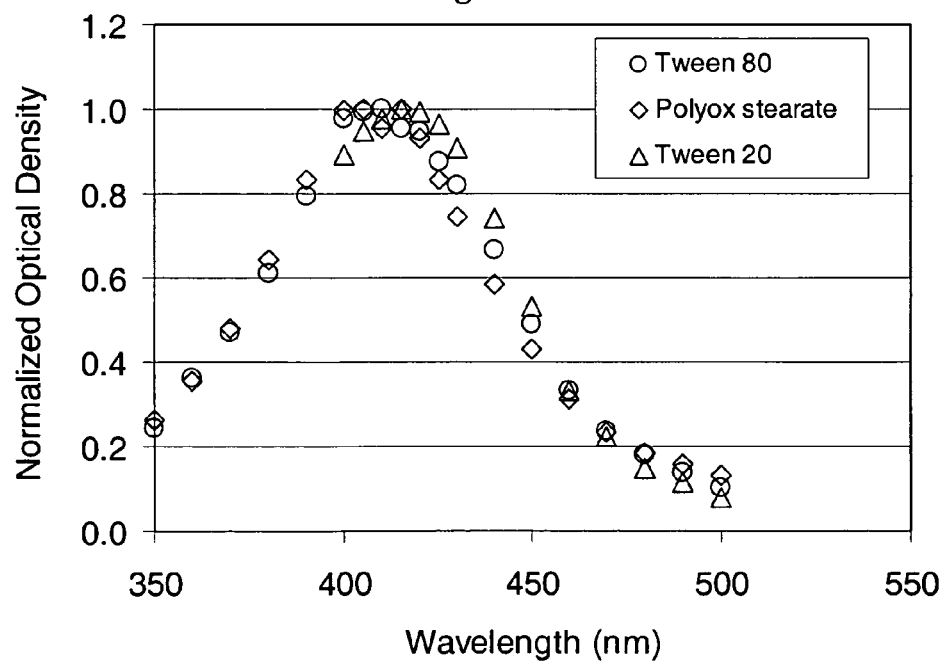
FIG. 18 shows representative spectrograms obtained by UV-Visible spectroscopic analysis of an aqueous antimicrobial silver nanoparticle composition in accordance with the present invention, wherein various aqueous antimicrobial silver nanoparticles compositions were prepared from solutions comprising various surfactants as indicated.

To prepare silver nanoparticles comprising solutions, a given surfactant solution (0.3 mL), acesulfame potassium salt solution (1 mL, 0.125M), silver nitrate solution (0.75 mL, 0.1M) were mixed and then TEMED (0.3 mL) were added. The solutions were heated in microwave oven briefly until the solution became yellow. OD versus wavelength data was recorded for each surfactant (FIG. 18). Though small different in the maxima was seen all were in 415-425 nm range indicating consistent nanoparticles size.

Example B23

Silver Nanoparticles Compositions Prepared using Triethanolamine

Silver saccharinate powder was prepared from equimolar mixtures of silver nitrate and sodium saccharinate solutions. Silver saccharinate powder (30-35 mg) was added to Tween 20 solution (1 mL, 16.7 g/L) and then water (4 mL) was added. To this mixture, triethanolamine (0.225 g) was added and it was briefly heated in microwave until the content became yellow.

Various articles with antimicrobial property were prepared using this above composition. Nylon fibers were made by dipping for 2 hours at 55C and rinsing them. Cotton gauze and satin pieces (2"×2") were prepared by dipping them in the above composition for a minute, then blotting them and soaking them in ethanol (10 mL) for 5 minutes, re-blotting them and drying at 55C for 15 minutes.

Example B24

Silver Nanoparticles Compositions Prepared using Poly Vinyl Alcohol (PVA)

PVA solution was prepared in de-ionized water (0.02-00.03 g/10 mL). PVA solution (1 mL), sodium saccharinate (1 mL, 0.125M) and silver nitrate (1 mL, 0.1M) were vortex together. TEMED (0.1 mL) was added and vortexed again. The contents were briefly heated in microwave oven. The solution turned grey brown though the OD max of the solution was 455 nm.

Example B25

Silver Nanoparticles Compositions using Polyacrylamide (PAA) as Stabilizer

An identical test to Example B24 was carried out but instead of PVA, poly acrylamide was used. PAA was made as a concentrate and 0.05 g concentrate was added to 1 mL water. The OD maximum of the composition was 450 nm and its color was brown.

Example B26

Silver Nanoparticles Compositions using Polyvinyl Pyrrolidone (PVP) as Stabilizer In Example B24, PVP was replaced with PVP solution (0.25 g/10 mL water) and the test repeated. The resulting composition after heating turned green instead of yellow. The OD max was seen at 435 nm with the spectrum being less sharp than in the case of use of Tween 20 indicating a broad particle distribution.

Example B27

Silver Nanoparticles Compositions using Potassium Sorbate as Stabilizer

A solution of potassium sorbate (0.1 M) was prepared. The sorbate solution (1 mL) was mixed with Tween 20 (1 mL, 16.7 g/L), and silver nitrate (1 mL, 0.1M) were vortex together. TEMED (0.05 mL) was further added and vortexed again. The contents in a test tube were briefly heated when solution color changed to orange yellow. The composition OD maximum was 410 nm somewhat less than the number for saccharinate based composition. This example shows that one can use a double bond containing molecule (silver sorbate) as the source of silver.

Example B28

Silver Nanoparticles Composition using Sodium Oleate w/o Tween 20

Sodium oleate (4-5 mg) was dissolved in 1 ml water in a test tube. To which were added sodium saccharinate (1 mL, 0.105M) and silver nitrate (1 mL, 0.1M) to give a chunky white precipitate. To the test tube TEMED (0.2 mL) was added and briefly microwaved to heat the contents. Upon heating a color change to yellow took place indicating formation of silver nanoparticles. OD of the maximum was not recorded.

Example B29

Silver Composition Comprising Silver—TEMED Complex

Tween 20 solution (1 mL, 16.7 g/L) and silver nitrate (1 mL, 0.01M) were mixed in a test tube. Then TEMED (0.1 mL) was added to briefly heat in microwave oven to deposit silver as metallic film on tube walls. The area of the glass surface coated with purplish metallic film became poorly water wetting as indicated by the flat water-air interface instead of a curved interface.

Example B30

Silver Composition Comprising Sorbate—Effect of Ethanol on Stability

Solutions of silver nanoparticles composition of Example B27 were prepared by diluting with water and 66% water-33% ethanol mixture (1:100 dilution factor). The UV/VIS scans were recorded of either solution fresh and of the water-ethanol based solution after 5 days. No change in the spectra was observed indicating tolerance of silver nanoparticles to ethanol.

Example B31

Use of Different Amines as Reducing Agents in the Preparation of Silver Nanoparticles Compositions Tween 20 solution (1 mL, 16.7 g/L), sodium saccharinate (1 mL, 0.125M) and silver nitrate (1 mL, 0.1M) were vortexed together. Different amines (0.1 mL) was added and vortexed again. If needed, the contents were briefly heated in microwave oven. The OD maxima of the solutions were recorded.

Following amines were tested: N,N, N'N' tetramethyl butylenediamine, ethanolamine, cyccohexylamine, dipropylamine, triethanolamine.
Of these dipropylamine and triethanolamine successfully gave yellow colored solution indicating the presence of silver nanoparticles with identical solutions OD maxima at 415 nm and practically identical spectral shapes of the curves.

Example B32

Silver Composition using Powder Form of Silver Saccharinate

Silver saccharinate powder (15-20 mg) was added to Tween 20 solution (1 mL, 16.7 g/L) and then water (2 mL) was added. To this mixture, triethanolamine (0.1 g) was added and it was briefly heated in microwave until the content became yellow. The OD max of the solution was 420 nm and the shape of UV-VIS spectrum was identical to a composition made by in-situ formation of silver saccharinate.

Nylon fibers were made by dipping in silver nanoparticles composition above for 2 hours at 55C and rinsing them. Cotton gauze and satin pieces (2"×2") were prepared by dipping them in the above composition for a minute, then blotting them and soaking them in ethanol (10 mL) for 5 minutes, re-blotting them and drying at 55C for 15 minutes. The fibers exhibited antimicrobial activity.

Example B33

Silver Composition Comprising Fumarate

Sodium fumarate was made as follows: 0.116 g of fumaric acid was added to 10 ml water in a test tube. Further, 2 molar equivalents of sodium carbonate were added to form sodium fumarate. Without isolating sodium fumarate, 1 ml of the sodium fumarate solution above, Tween 20 solution (1 mL, 16.7 g/L) and silver nitrate (1 mL, 0.1M) were mixed in succession and then TEMED (0.1 mL) was added. The tube contents were heated briefly in microwave to yield a yellow colored solution with OD max of 420 nm. Without Tween 20, the solution color is purple indicating silver nanoparticles of different size may be forming.

Example B34

Silver Nanoparticles Comprising Gel

In a cup, glycerol (5.0 g) was weighed, carboxymethyl cellulose (0.5 g) was added and hand mixed to coat cellulose particles uniformly with glycerol. Warm de-ionized water (40 mL) was added to the cup and the resulting mass mixed to yield smooth gel. Silver nanoparticle composition made from triethanolamine (0.1 g) from example B23 was added and mixed to uniformity to give a yellow colored gel.

To a portion of the gel (10 g), 1 g each of citric acid and water were added to provide an antimicrobial gel that could be used in the treatment of onychomycosis.

What is claimed is:

1. A method of making elemental silver nanoparticles comprising, a) admixing in no particular order, an aqueous solution of a stabilizing agent, and an aqueous solution of a silver salt, and b) adding a reducing agent to trigger the formation of elemental silver nanoparticles, wherein the reducing agent consists of a tertiary diamine.

2. The method of claim 1, further comprising, c) heating the final solution.

3. The method of claim 1, wherein the stabilizing agent solution comprises a surfactant, a polymer or both.

4. The method of claim 3, wherein the polymer is a homopolymer or copolymer of acrylamide, methacrylamide, polyamide, polyurethane, acrylic acid, methacrylic acid, hydroxyethyl methacrylate, acrylonitrile, 2-acrylamido-2-methylpropane sulfonic acid or its sodium, potassium, or ammonium salt, 2-vinyl pyrrolidone, 2-vinyl oxazoline, vinyl acetate, or maleic anhydride, or combinations thereof.

5. The method of claim 1, further comprising, forming the nanoparticles in situ on the surface of an article.

6. The method of claim 5, wherein the article is a woven or nonwoven fiber article.

7. The method of claim 5, wherein the article is a medical device, polymer, a fiber, a metal, glass, ceramic, fabric or combination thereof.

8. The method of claim 1, wherein the silver salt solution results from an ionic exchange reaction between an anion originally associated with the silver cation and a second cation-anion pair.

* * * * *

UNITED STATES PATENT AND TRADEMARK OFFICE
CERTIFICATE OF CORRECTION

PATENT NO. : 8,900,624 B2
APPLICATION NO. : 11/194951
DATED : December 2, 2014
INVENTOR(S) : Bhalchandra M. Karandikar, Bruce L. Gibbins and Ken A. Cornell Page 1 of 1

It is certified that error appears in the above-identified patent and that said Letters Patent is hereby corrected as shown below:

On the Title Page

Item (57) in the Abstract (last sentence):

"...The present invention further comprises treatment of humans and animals wacr6ith the antimicrobial devices described herein." should read --...The present invention further comprises treatment of humans and animals with the antimicrobial devices described herein.--

Signed and Sealed this
Thirtieth Day of June, 2015

Michelle K. Lee
*Director of the United States Patent and Trademark Office*